United States Patent
Albertsen et al.

(10) Patent No.: US 11,015,209 B2
(45) Date of Patent: *May 25, 2021

(54) WHEAT MS1 POLYNUCLEOTIDES, POLYPEPTIDES, AND METHODS OF USE

(71) Applicant: PIONEER HI-BRED INTERNATIONAL, INC., Johnston, IA (US)

(72) Inventors: Marc C Albertsen, Grimes, IA (US); Ute Baumann, Glen Osmond (AU); Andrew Mark Cigan, De Forest, WI (US); Manjit Singh, Johnston, IA (US); Elise Tucker, Clapham (AU); Ryan Whitford, Eastwood (AU)

(73) Assignee: PIONEER HI-BRED INTERNATIONAL, INC.

( * ) Notice: Subject to any disclaimer, the term of this patent is extended or adjusted under 35 U.S.C. 154(b) by 401 days.

This patent is subject to a terminal disclaimer.

(21) Appl. No.: 15/514,195

(22) PCT Filed: Sep. 21, 2015

(86) PCT No.: PCT/US2015/051214
§ 371 (c)(1),
(2) Date: Mar. 24, 2017

(87) PCT Pub. No.: WO2016/048891
PCT Pub. Date: Mar. 31, 2016

(65) Prior Publication Data
US 2017/0298383 A1    Oct. 19, 2017

Related U.S. Application Data

(60) Provisional application No. 62/187,591, filed on Jul. 1, 2015, provisional application No. 62/056,365, filed on Sep. 26, 2014.

(51) Int. Cl.
| | |
|---|---|
| *C12N 15/82* | (2006.01) |
| *A01H 5/10* | (2018.01) |
| *C07K 14/415* | (2006.01) |
| *C12Q 1/6895* | (2018.01) |
| *A01H 1/02* | (2006.01) |

(52) U.S. Cl.
CPC ..... *C12N 15/8289* (2013.01); *C12N 15/8213* (2013.01); *C12N 15/8231* (2013.01); *C12N 15/8287* (2013.01); *A01H 1/02* (2013.01); *A01H 5/10* (2013.01); *C07K 14/415* (2013.01); *C12Q 1/6895* (2013.01); *C12Q 2600/13* (2013.01)

(58) Field of Classification Search
CPC .............................................. C12N 15/8289
See application file for complete search history.

(56) References Cited

U.S. PATENT DOCUMENTS

| | | |
|---|---|---|
| 5,689,049 A | 11/1997 | Cigan et al. |
| 5,792,853 A | 8/1998 | Cigan et al. |
| 6,013,859 A | 1/2000 | Fabijanski et al. |
| 6,162,964 A | 12/2000 | Fabijanski et al. |
| 6,191,343 B1 | 2/2001 | Fabijanski et al. |
| 6,407,311 B1 | 6/2002 | Feldman et al. |
| 6,743,968 B2 | 6/2004 | Dellaporta et al. |
| 7,696,405 B2 | 4/2010 | Cigan et al. |
| 7,875,764 B2 | 1/2011 | Wu et al. |
| 8,013,218 B2 | 9/2011 | Wu et al. |
| 8,614,367 B2 | 12/2013 | Wu et al. |
| 8,933,296 B2 | 1/2015 | Fox et al. |
| 9,803,215 B2 | 10/2017 | Albertsen et al. |
| 10,519,464 B2 * | 12/2019 | Albertsen .......... C12N 15/8287 |
| 2011/0247101 A1 * | 10/2011 | Alexandrov ......... C07K 14/415 800/298 |

FOREIGN PATENT DOCUMENTS

| | | | |
|---|---|---|---|
| WO | 2014/039815 A2 | 3/2014 | |
| WO | WO 2016/048891 | * 3/2016 | .......... C12N 15/8289 |

OTHER PUBLICATIONS

Klindworth, D. et al., Crop Science 2002; vol. 42, No. 5; pp. 1447-1450.*
Zhou, K. et al., Crop Science, 2006; vol. 46, No. 1; pp. 250-255.*
Klindworth, D.L. et al., 2002 Crop Science; vol. 42, No. 5, pp. 1447-1450.*
Tucker, E. et al. Nature Communications, Oct. 2017, vol. 8, No. 869, pp. 1-10.*
Fernandez, J., and Wilson, Z., Plant Biotechnology Journal; EPub Mar. 29, 2014, vol. 12, pp. 765-777.*
Klindworth, D.L. et al. 2002 Crop Science; vol. 42, No. 5. 1447-1450. (Year: 2002).*
Tucker, E. et al. Nature Communications, Oct. 2017, vol. 8, No. 869, pp. 1-10. (Year: 2017).*

(Continued)

*Primary Examiner* — Russell Kallis

(57) ABSTRACT

Compositions and methods are capable of modulating male fertility in a plant. Compositions comprise polynucleotides and polypeptides, and fragments and variants thereof, which modulate male fertility. Expression cassettes comprise a male-fertility polynucleotide, or fragment or variant thereof, operably linked to a promoter, wherein expression of the polynucleotide modulates the male fertility of a plant. The level and/or activity of a polynucleotide that influences male fertility is modulated in a plant or plant part. Regulatory sequences drive expression in a male-tissue-preferred manner and may be targets to downregulate an operably linked gene. Methods to track mutations that induce nuclear recessive male sterility in subsequent selfing and crossing of wheat lines containing the mutations are also provided. Male-sterile plants may be maintained by pollinating with a maintainer plant.

10 Claims, 4 Drawing Sheets

Specification includes a Sequence Listing.

(56) References Cited

OTHER PUBLICATIONS

International Search Report and Written Opinion of the International Searching Authority for PCT/US2015/051214 dated Mar. 7, 2016.
International Search Report PCT/US2015/051214 dated Mar. 7, 2016.
Keller et al: "Map-based isolation of disease resistance genes from bread wheat:", Genetical Research, Cambridge University Press, Cambridge, GB, vol. 85, No. 2, Apr. 1, 2005, pp. 93-100.
Krattinger S et al: "Map-based cloning of genes in triticeae", Jan. 1, 2009, Plant Genetics/Genomics vol. 7; Genetics and Genomics of the Triticeae, pp. 337-357.
Daryl L Klindworth et al: "Chromosomal Location of Genetic Male Sterility Genes in Four Mutants of Hexaploid Wheat", Crop Science: A Journal Serving the International Community of Crop Scientists, Crop Science Society of America, US, vol. 42, No. 5, Jan. 1, 2002, pp. 1447-1450.
R. Whitford et al: "Hybrid breeding in wheat: technologies to improve hybrid wheat seed production", Journal of Experimental Botany, vol. 64, No. 18, Oct. 31, 2013, pp. 5411-5428.
Uniprot accession No. Q75GY0 Jul. 5, 2004, XP002751259.
UniParc accession No. UPI000234E968 Nov. 16, 2011, XP002751258.
UniProt accession No. F2E958 May 31, 2011, XP002751257.
Geneseq accession No. AZN49541 Nov. 24, 2011, XP002751256.
Written Opinion of the International Searching Authority PCT/US2015/051214 dated Mar. 7, 2016.
Zhou, Kuanji et al. "The 4E-ms System of Producing Hybrid Wheat", Crop Science, Jan. 24, 2006. vol. 46(1). pp. 250-255.
Wilson, Z.A. et al. "The *Arabidopsis* Male Sterility1 (MS1) gene is a transcriptional regulator of male gametogenesis, with homology to the PHD-finger family of transcription factors" The Plant Journal. (2001) 28(1):27-39.

\* cited by examiner

Fig. 1

```
             1                                                                                                  100
BARLEY       MERSRRLLLVAGLLAALLPAAAATFGIQQGAQCDPTFLATQAALFCAPDMPTAQCCEPVVAAFDLGGGVPCLCRVAAEPQLVMAGLNATHLFALYTSCGG
WHEAT Ms1    MERSRGLLLVAGLLAALLPAAAA------QPGAPCEPALLATQVALFCAPDMPTAQCCEPVVAAVDLGGGVPCLCRVAAEPQLVMAGLNATHLLTLYSSCGG 101                                                                                                200
BARLEY       IRPGGAHLAAACQGPAPPAAVVSSPPPPSP---APRRKQAAHDAPPPPP-SSEKPS-PPP-QEHDGAA-HAKSAPALAAPTPLAP-AAATAPPPEAPHSA
WHEAT Ms1    LRPGGAHLAAACEGPAPPAAVVSSPPPPPPPPSAAPRRKQPAHDAPPPPPPSSEKPSSPPPSQDHDGAAPRAKAAPAQAATSTLAPAAAATAPPQAPHSA 201        224
BARLEY       ASSSDS---AFIFIAAAMLAIYIVL
WHEAT Ms1    APTAPSKAAFFFVATAMLGLYIIL
```

Fig. 2

|  | *ms1d/ms1d* | *ms1e/ms1e* | *ms1f/ms1f* |
|---|---|---|---|
| Wild-type | 1847 CCTGCGAAGGTACGTTGT 1864 | 2954 AGCCCCCCGCCCCCGC 2969 | 1672 GCCCAGTGCTGCGAGCCCGT 1691 |
| *ms1d/ms1d* | CCTGCGAAGATACGTTGT | AGCCCCCCGCCCCCGC | GCCCAGTGCTGCGAGCCCGT |
| *ms1e/ms1e* | CCTGCGAAGGTACGTTGT | AGCCCCCCA_CCCCGC | GCCCAGTGCTGCGAGCCCGT |
| *ms1f/ms1f* | CCTGCGAAGGTACGTTGT | AGCCCCCCGCCCCCGC | GCCCAGTGCTACGAGCCCGT |
|  | G → A | G → A & deletion | G → A |

Fig. 4

```
                 1.........11.........21.........31.........41.........51.........60
3   Hordeum      MERSRRLLLLVAGLLA--ALLPAAAATF-----GLQQGAQCDPTFLATQAALFCAPDMPT
5   Triticum     MERSRGLLLLVAGLLA--ALLPAAAA-------QPGAFCEPALLATQVALFCAPDMPT
39  Brachypodium MERSHHLLLLVIGLLA--ALLPAAAATFGTT---QPEPGAPCEPTLLATQVSLFCAPDMPT
40  Oryza        MERS-HLAVLLGLLAFAAGVPAAAAATAVEGAQAATAEASCEPSILATQVSLFCAPDMPT
                 ****  * *:*:***   .*:****     *           *     ***.:.********

61........71........81........91........101........111........120
3   Hordeum      AQCCEPVVAAFDLGGGVPCLCRVAAEPQLVMAGLNATHLFALYTSCGGIRPGGAHLAAAC
5   Triticum     AQCCEPVVAAVDLGGGVPCLCRVAAEPQLVMAGLNATHLLTLYSSCGGLRPGGAHLAAAC
39  Brachypodium AQCCEPVVASVDLGGGVPCLCRVAAEPQLVMAGLNATHLLTLYTSCGGLRPGGAHLAAAC
40  Oryza        AQCCEPVVASVDLGGGVPCLCRVAAEPQLIISGLNATHLLTLYAACGGLRPGGARLAAAC
                 ********:.:.*******:*********::.:*******:.**::.***:****:*****

121.......131.......141.......151.......161.......171.......180
3   Hordeum      QGPAPPAAVVSSPPPPSP---APRRKQAAHDAPPPP--SSEKPSPPP--QEHDGAA-HAK
5   Triticum     EGPAPPAAVVSSPPFPPPSAAPRRKQPAHDAPPPPPPSSEKPSSPPPSQDHDGAAPRAK
39  Brachypodium EGPAPPAAVVSAPPPSAA----PRRKQPAHEAPPPPP-STEKPSPPP---QQDNVTAHGK
40  Oryza        EGPAPPASIVTAPPPPVA----FRRKPPAREAPPPPP-AAEKLSPPP--QQHDDSDHNKR
                 :*******::.::*.***.   ****:.:.:.****** :.* *.***     . : .

181.......191.......201.......211.......221.......231.......240
3   Hordeum      SAPALAAPTPLAP-AAAT--APPPEAPHSAASSSDS--AFIFIAAAMLAIYIVL------
5   Triticum     AAPAQAATSTLAPAAAAT--APPPQAPHSAAPTAPSKAAFFFVATAMLGLYIIL------
39  Brachypodium AIPTHAATSPLAPAASMIHMSPPPACNPCSGSAASSAEGPLLIAALLVITAIIVGTLDD
40  Oryza        VGPLPRGSP--PPYAQSVPVGPAAAPPPPPRSGASSSLQAPLAATTTIVAITLIAAAQY--
                 . * . .         .       *      :.::      :    :   . :  :

241
3   Hordeum      --
5   Triticum     --
39  Brachypodium K-
40  Oryza        --
```

WHEAT MS1 POLYNUCLEOTIDES, POLYPEPTIDES, AND METHODS OF USE

FIELD OF THE INVENTION

The present invention relates to the field of plant molecular biology, more particularly to influencing male fertility.

REFERENCE TO ELECTRONICALLY-SUBMITTED SEQUENCE LISTING

The official copy of the sequence listing is submitted electronically via EFS-Web as an ASCII formatted sequence listing file named RTS20250D-PCT_ST25.txt, last modified on Sep. 21, 2015, having a size of 79 KB, and is filed concurrently with the specification. The sequence listing contained in this ASCII formatted document is part of the specification and is herein incorporated by reference in its entirety.

BACKGROUND OF THE INVENTION

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinated if pollen from one flower is transferred to the same or another flower of the same plant or a genetically identical plant. A plant is cross-pollinated if the pollen comes from a flower on a genetically different plant.

In certain species, such as *Brassica campestris*, the plant is normally self-sterile and can only be cross-pollinated. In predominantly self-pollinating species, such as soybeans, wheat, and cotton, the male and female plants are anatomically juxtaposed such that during natural pollination, the male reproductive organs of a given flower pollinate the female reproductive organs of the same flower.

Bread wheat (*Triticum aestivum*) is a hexaploid plant having three pairs of homologous chromosomes defining genomes A, B and D. The endosperm of wheat grain comprises two haploid complements from a maternal cell and one from a paternal cell. The embryo of wheat grain comprises one haploid complement from each of the maternal and paternal cells. Hexaploidy has been considered a significant obstacle in researching and developing useful variants of wheat. In fact, very little is known regarding how homologous genes of wheat interact, how their expression is regulated, and how the different proteins produced by homologous genes function separately or in concert. Strategies for manipulation of expression of male-fertility polynucleotides in wheat will require consideration of the ploidy level of the individual wheat variety. *Triticum aestivum* is a hexaploid containing three genomes designated A, B, and D (N=21); each genome comprises seven pairs of nonhomologous chromosomes. Einkorn wheat varieties are diploids (N=7) and emmer wheat varieties are tetraploids (N=14).

An essential aspect of much of the work underway with genetic male sterility systems is the identification of genes influencing male fertility. Such a gene can be used in a variety of systems to control male fertility including those described herein.

BRIEF SUMMARY OF THE INVENTION

Compositions and methods for modulating male fertility in a plant are provided. Compositions comprise expression cassettes comprising one or more male-fertility polynucleotides, or fragments or variants thereof, operably linked to a promoter, wherein expression of the polynucleotide modulates the male fertility of a plant. Various methods are provided wherein the level and/or activity of a polynucleotide or polypeptide that influences male fertility is modulated in a plant or plant part. Methods for identifying and/or selecting wheat plants that are homozygous or heterozygous for a mutation that induces nuclear recessive male sterility are also provided.

DESCRIPTION OF THE FIGURES

FIG. 1 shows an alignment of barley (SEQ ID NO: 3) and wheat (SEQ ID NO: 5) MS1 amino acid sequences.

FIG. 2 shows allele series sequence traces for ms1d, ms1e, and ms1f. Coordinate numbers correspond to positions in SEQ ID NO: 7.

FIG. 4 is an alignment of MS1 homologues of *Hordeum vulgare* (SEQ ID NO: 3), *Triticum aestivum* (SEQ ID NO: 5), *Brachypodium distachyon* (SEQ ID NO: 39), and *Oryza sativa* (SEQ ID NO: 40).

DETAILED DESCRIPTION

Figure 3:
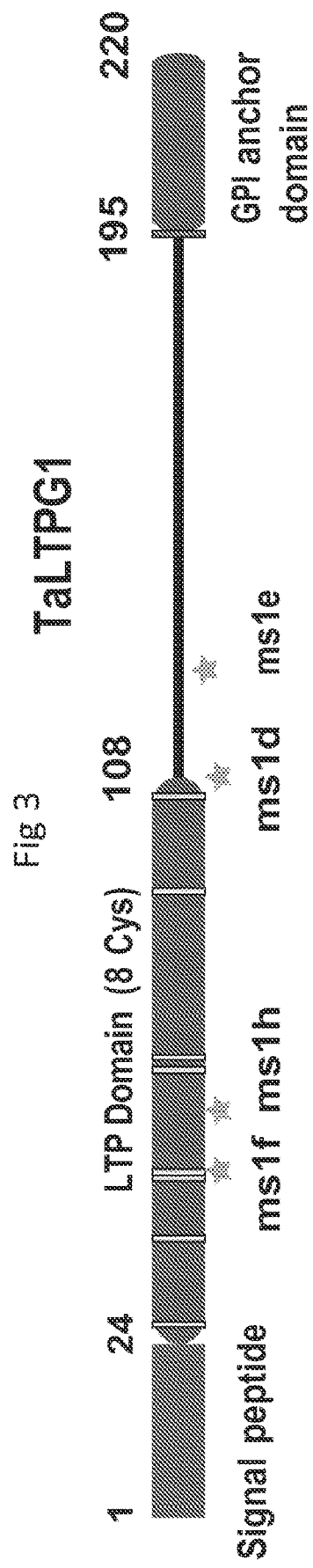
FIG. 3 is a graphic representation of the structure of wheat MS1 (also referred to as TaLTPG1).

The present inventions now will be described more fully hereinafter; some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Male-Fertility Polynucleotides

Compositions disclosed herein include polynucleotides and polypeptides that influence male fertility. In particular, isolated polynucleotides are provided comprising nucleotide sequences encoding an amino acid sequence set forth in SEQ ID NO: 3, 5, 39, or 40 or active fragments or variants thereof. Further provided are polypeptides having an amino acid sequence encoded by a polynucleotide described herein, for example those set forth in SEQ ID NO: 3, 5, 39, or 40 or active fragments or variants thereof.

Sexually reproducing plants develop specialized tissues for the production of male and female gametes. Successful production of male gametes relies on proper formation of the male reproductive tissues. The stamen, which embodies the male reproductive organ of plants, contains various cell types, including for example, the filament, anther, tapetum, and pollen. As used herein, "male tissue" refers to the specialized tissue in a sexually reproducing plant that is responsible for production of the male gamete. Male tissues include, but are not limited to, the stamen, filament, anther, tapetum, and pollen.

The process of mature pollen grain formation begins with microsporogenesis, wherein meiocytes are formed in the sporogenous tissue of the anther. Microgametogenesis follows, wherein microspore nuclei undergo an asymmetric mitotic division to develop the microgametophyte, or pollen grain. The condition of "male fertility" or "male fertile" refers to those plants producing a mature pollen grain capable of fertilizing a female gamete to produce a subsequent generation of offspring. The term "influences male fertility" or "modulates male fertility", as used herein, refers to any increase or decrease in the ability of a plant to produce a mature pollen grain when compared to an appropriate control. A "mature pollen grain" or "mature pollen" refers to any pollen grain capable of fertilizing a female gamete to produce a subsequent generation of offspring. Likewise, the term "male-fertility polynucleotide" or "male-fertility polypeptide" refers to a polynucleotide or polypeptide that modulates male fertility. A male-fertility polynucleotide may, for example, encode a polypeptide that participates in the process of microsporogenesis or microgametogenesis.

Certain male sterility genes such as MAC1, EMS1 or GNE2 (Sorensen et al. (2002) *Plant J.* 29:581-594) prevent cell growth in the quartet stage. Mutations in the SPOROCYTELESS/NOZZLE gene act early in development, but impact both anther and ovule formation such that plants are male and female sterile. The SPOROCYTELESS gene of Arabidopsis is required for initiation of sporogenesis and encodes a novel nuclear protein (*Genes Dev.* 1999 Aug. 15; 13(16):2108-17).

Male-fertility polynucleotides disclosed herein include homologs and orthologs of polynucleotides shown to influence male fertility. For example, male-fertility polynucleotides, and active fragments and variants thereof, disclosed herein include homologs and orthologs of Ms1. Plants lacking a functional Ms1 exhibit physiological changes in reproductive-tissue development and are male-sterile. Phenotyping of ms1 mutants uses techniques known in the art. For example, screening for a male-sterility phenotype in Gladius wheat is performed as follows: To prevent open-pollinated seeds from forming, spikes are covered before anthesis with paper bags fastened with a paper clip. At least three spikes per plant are covered and used for quantitative fertility scoring. To determine the quantitative fertility score, the number of florets per spike and the number of seed per spike are counted and expressed as the number of seeds per floret formed.

As disclosed elsewhere herein, SEQ ID NO: 4 provides a wheat Ms1 coding sequence. SEQ ID NO: 7 provides a native wheat Ms1 genomic sequence. SEQ ID NO: 9 provides a variant Ms1 genomic sequence. SEQ ID NO: 39 provides an MS1 homologue from *Brachypodium*. SEQ ID NO: 40 provides an MS1 homologue from rice.

Mutants of the *Triticum aestivum* L. ms1 locus on chromosome arm 4BS include:
Pugsley's (ms1a); see
Pugsley, A. T. and R. N. Oram (1959) Genic male sterility in wheat. Aust. Pl. Breed. Genet. Newsl. No. 14:10-11;
Suneson, C. A. (1962) Use of Pugsley's sterile wheat in cross breeding. Crop Sci. 2:534-535; and
Waninge, J. and Zeven, A. C. (1968) Chromosome numbers in Pugley's (sic) male sterile wheat. Euphytica 17:378-380.
Probus (ms1b); see Fossati, A. and M. Ingold (1970) A male sterile mutant in *Triticum aestivum*. Wheat Information Service (Kyoto) 30:3-10.
Cornerstone (ms1c); see Driscoll, C. J. and K. K. Barlow (1976) Male sterility in plants: Induction, isolation and utilization. pp. 123-131 in Induced Mutation in Cross-Breeding, IAEA, Vienna, Austria.

The mutations in Probus and Cornerstone were radiation-induced and are presumed to result from a terminal deletion of chromosome arm 4BS. The Pugsley's mutant was isolated as a spontaneous mutant. The location of the ms1 gene has been physically mapped to a region comprising the distal 16% of the 4BS chromosome arm (Endo et al. (1991) *The Japanese Journal of Genetics* 66(3):291-295; Klindworth et al. (2002) *Crop Sci.* 42:1447-1450; Cenci et al. (2003) *Theor. Appl. Genet* 107(5):931-9.

The causal variations of the Ms1 mutations ms1d, ms1e, ms1f, and ms1h are provided herein, as are markers tightly linked to the Ms1 gene on chromosome 4BS. Markers include ET0487, ET0488, ET0489, ET0490, ET0491, ET0495, 007-0033.1, and 007-0046.1; see SEQ ID NOS: 24-29 and 32-33. Such markers may be used to track ms1d, ms1e, ms1f, or ms1h in subsequent selfing and crossing of wheat lines containing the ms1d, ms1e, ms1f, or ms1h mutations, ensuring that the male sterility trait is advantageously inherited in a wheat breeding program.

The Ms1 mutations ms1d, ms1e, and ms1f are recessive mutations of the Ms1 gene that were induced in the Chris wheat variety using ethyl methanesulfonate (Klindworth et al. 2002. *Crop Sci.* 42:1447-1450). The ms1h mutation in exon 1 was created by TILLING (Targeting Induced Local Lesions IN Genomes; McCallum et al. (2000) *Nat. Biotechnol.* 18:455-457).

A plant breeder can advantageously use molecular markers to identify individuals containing an Ms1 mutation by identifying marker alleles that show a statistically significant probability of co-segregation with male sterility, manifested as linkage disequilibrium. This is referred to as marker assisted selection (MAS). Thus, methods for the selection of mutant wheat plants that are homozygous or heterozygous for a mutation in the Ms1 gene, such as but not limited to ms1d, ms1e, and ms1f, are also provided.

To perform MAS, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, DNA sequencing of a PCR amplification product, or the like. For any of the marker sequences described herein, one of ordinary skill in the art would understand how to obtain the allele at a marker locus in a particular wheat line or variety using known DNA amplification and sequencing techniques. For the purposes described herein, the lines or varieties that were used were publicly available. Hence, DNA could be obtained, and one of ordinary skill in the art could either use the provided primers or develop primers from the provided reference sequence to amplify and obtain the sequence at each marker locus from each line or variety.

After the presence (or absence) of a particular marker allele in the biological sample is verified, the plant is selected and is crossed to a second plant, optionally a wheat plant from an elite line. The progeny plants produced by the cross can be evaluated for that specific marker allele, and only those progeny plants that have the desired marker allele will be chosen.

Through marker assisted selection, a plant breeder can follow the presence of the male sterility trait through controlled crosses to obtain, when desired, a new plant containing an Ms1 mutation in either the homozygous or heterozygous state, thus maintaining the Ms1 mutations. In addition, marker assisted selection can be used to produce mutant male sterile seed parents that would be used as female, i.e. plants that need pollination by a pollen donor plant, to produce seeds of commercial interest. Alternatively, marker assisted selection could be used to produce F1 hybrids containing an Ms1 mutation in the heterozygous state.

Any of the markers provided herein, as well as any marker linked to and associated with any of those markers, can be used for marker assisted selection of the male sterility trait.

The term "linkage" is used to describe the degree with which one marker locus is "associated with" another marker locus or some other locus (for example, a male sterility locus). A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time).

Linkage can be expressed as a desired limit or range. For example, in some embodiments, any marker is linked (genetically and physically) to any other marker (or locus such as Ms1) when the markers are separated by less than 50, 40, 30, 25, 20, or 15 map units (or cM). Further linkage can be described by separations of 14, 13, 12, 11, 10, 9, 8, 7, 6, 5, 4, 3, 2, 1 map units (or cM). In some aspects, it is advantageous to define a bracketed range of linkage, for example, between 10 and 20 cM, between 10 and 30 cM, or between 10 and 40 cM.

The more closely a marker is linked to a second locus, the better an indicator for the second locus that marker becomes. Thus, "closely linked loci" such as a marker locus and a second locus display an inter-locus recombination frequency of 10% or less, or about 9% or less, or about 8% or less, or about 7% or less, or about 6% or less, or about 5% or less, or about 4% or less, or about 3% or less, and or about 2% or less. In other embodiments, the relevant loci display a recombination frequency of about 1% or less, e.g., about 0.75% or less, or about 0.5% or less, or about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two genetic markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5, 0.25, 0.1, 0.075, 0.05, 0.025, or 0.01 cM or less from each other.

Although particular marker alleles can show co-segregation with the male sterility phenotype, it is important to note that the markers are not necessarily part of the locus responsible for expression of male sterility. For example, it is not a requirement that the marker polynucleotide sequence be part of the Ms1 gene. The association between a specific marker allele and the male sterility phenotype is due to the original "coupling" linkage phase between the marker allele and the Ms1 mutation in the wheat line in which the Ms1 mutation originated. Because ms1d, ms1e, and ms1f originated in variety Chris, the marker alleles in Chris within the Ms1 region can be used to track the ms1d, ms1e, and ms1f mutations in subsequent generations.

Isolated or substantially purified nucleic acid molecules or protein compositions are disclosed herein. An "isolated" or "purified" nucleic acid molecule, polynucleotide, polypeptide, or protein, or biologically active portion thereof, is substantially or essentially free from components that normally accompany or interact with the polynucleotide or protein as found in its naturally occurring environment. Thus, an isolated or purified polynucleotide or polypeptide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the polypeptides disclosed herein or biologically active portion thereof is recombinantly produced, optimally culture medium represents less than about 30%, 20%, 10%, 5%, or 1% (by dry weight) of chemical precursors or non-protein-of-interest chemicals.

A "subject plant" or "subject plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or plant cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

Fragments and variants of the disclosed polynucleotides and proteins encoded thereby are also provided. By "fragment" is intended a portion of the polynucleotide or a portion of the amino acid sequence and hence protein encoded thereby. Fragments of a polynucleotide may encode protein fragments that retain the biological activity of the native protein and hence influence male fertility; these fragments may be referred to herein as "active fragments." Alternatively, fragments of a polynucleotide that are useful as hybridization probes or which are useful in constructs and strategies for down-regulation or targeted sequence modification generally do not encode protein fragments retaining biological activity, but may still influence male fertility. Thus, fragments of a nucleotide sequence may range from at least about 20 nucleotides, about 50 nucleotides, about 100 nucleotides, up to the full-length polynucleotide encoding a polypeptide disclosed herein.

A fragment of a polynucleotide that encodes a biologically active portion of a polypeptide that influences male fertility will encode at least 15, 25, 30, 50, 100, 150, or 200 contiguous amino acids, or up to the total number of amino acids present in a full-length polypeptide that influences male fertility (for example, SEQ ID NO: 3, 5, 39, or 40). Fragments of a male-fertility polynucleotide that are useful as hybridization probes or PCR primers, or in a down-regulation construct or targeted-modification method generally need not encode a biologically active portion of a polypeptide but may influence male fertility.

Thus, a fragment of a male-fertility polynucleotide as disclosed herein may encode a biologically active portion of a male-fertility polypeptide, or it may be a fragment that can be used as a hybridization probe or PCR primer or in a downregulation construct or targeted-modification method using methods known in the art or disclosed below. A biologically active portion of a male-fertility polypeptide can be prepared by isolating a portion of one of the male-fertility polynucleotides disclosed herein, expressing the encoded portion of the male-fertility protein (e.g., by recombinant expression in vitro), and assessing the activity of the encoded portion of the male-fertility polypeptide. Polynucleotides that are fragments of a male-fertility polynucleotide comprise at least 16, 20, 50, 75, 100, 150, 200, 250, 300, 350, 400, 450, 500, 550, 600, 650, 700, 800, 900, 1000, 1200, 1400, 1600, 1800, 2000, 2200, 2400, 2600, 2800, 3000, 3200, 3400, 3600, 3800, or 4000 nucleotides, or up to the number of nucleotides present in a full-length male-fertility polynucleotide disclosed herein (e.g. SEQ ID NO: 1, 2, 4, 7, 42, 43, 44, or 45 or a polynucleotide that encodes SEQ ID NO: 39 or 40).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of a male-fertility polypeptide disclosed herein. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis, and which may encode a male-fertility polypeptide. Generally, variants of a particular polynucleotide disclosed herein will have at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to that particular polynucleotide (e.g., SEQ ID NO: 1, 2, 4, 7, 42, 43, 44, or 45) as determined by sequence alignment programs and parameters described elsewhere herein or known in the art.

Variants of a particular polynucleotide disclosed herein (i.e., a reference polynucleotide) can also be evaluated by comparison of the percent sequence identity between the polypeptide encoded by a variant polynucleotide and the polypeptide encoded by the reference polynucleotide. Thus, for example, an isolated polynucleotide may encode a polypeptide with a given percent sequence identity to the polypeptide of SEQ ID NO: 3, 5, 39, or 40. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins disclosed herein are biologically active, that is they continue to possess biological activity of the native protein, that is, male fertility activity as described herein. Such variants may result from, for example, genetic polymorphism or human manipulation. Biologically active variants of a male-fertility protein disclosed herein will have at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to the amino acid sequence for the native protein (e.g. SEQ ID NO: 3, 5, 39, or 40) as determined by sequence alignment programs and parameters described elsewhere herein or known in the art. A biologically active variant of a protein disclosed herein may differ from that protein by as few as 1-15 amino acid residues, as few as 1-10, such as 6-10, as few as 5, as few as 4, 3, 2, or even 1 amino acid residue.

The proteins disclosed herein may be altered in various ways including amino acid substitutions, deletions, truncations, and insertions. Methods for such manipulations are generally known in the art. For example, amino acid sequence variants and fragments of the male-fertility polypeptides can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides disclosed herein include both the naturally occurring sequences as well as DNA sequence variants. Likewise, the male-fertility polypeptides and proteins encompass both naturally occurring polypeptides as well as variations and modified forms thereof. Such polynucleotide and polypeptide variants may continue to possess the desired male-fertility activity, in which case the mutations that will be made in the DNA encoding the variant must not place the sequence out of reading frame and optimally will not create complementary regions that could produce secondary mRNA structure. See, EP Patent Application Publication No. 75,444.

Certain deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for male fertility activity.

Increases or decreases in male fertility can be assayed in a variety of ways. One of ordinary skill in the art can readily assess activity of the variant or fragment by introducing the polynucleotide into a plant homozygous for a stable male-sterile allele of the polynucleotide, and observing male tissue development in the plant. For example, to assay for male fertility activity conferred by fragments or variants of SEQ ID NO: 1, 2, 4, 7, 42, 43, 44, or 45, one of skill in the art can begin by identifying a plant expressing the ms1 phenotype or by constructing a plant homozygous for a mutation in the native Ms1 gene, resulting in male sterility. Subsequently, one could complement the mutation by providing the Ms1 polynucleotide, or fragment or variant thereof, and observing whether the male tissues of the plant develop normally and are able to produce mature pollen.

Variant functional polynucleotides and proteins also encompass sequences and proteins derived from a mutagenic and recombinogenic procedure such as DNA shuffling. With such a procedure, one or more different male fertility sequences can be manipulated to create a new male-fertility polypeptide possessing desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the male-fertility polynucleotides disclosed herein and other known male-fertility polynucleotides to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

II. Sequence Analysis

As used herein, "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The use of the term "polynucleotide" is not intended to limit the present disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides disclosed herein also encompass all forms of sequences including, but not limited to, single-stranded forms, double-stranded forms, hairpins, stem-and-loop structures, and the like.

III. Expression Cassettes

A male-fertility polynucleotide disclosed herein can be provided in an expression cassette for expression in an organism of interest. The cassette can include 5' and 3' regulatory sequences operably linked to a male-fertility polynucleotide as disclosed herein. "Operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

The expression cassettes disclosed herein may include in the 5'-3' direction of transcription, a transcriptional and translational initiation region (i.e., a promoter), a polynucleotide of interest, and a transcriptional and translational termination region (i.e., termination region) functional in the host cell (e.g., a plant cell). Expression cassettes are also provided with a plurality of restriction sites and/or recombination sites for insertion of the male-fertility polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, "heterologous" in reference to a polynucleotide or polypeptide sequence is a sequence that originates from a foreign species, or, if from the same species, is substantially modified from its native form in its composition and/or its genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, unless otherwise specified, a chimeric polynucleotide comprises a coding sequence operably linked to a transcription initiation region that is heterologous to the coding sequence.

In certain embodiments the polynucleotides disclosed herein can be stacked with any combination of polynucleotide sequences of interest or expression cassettes as disclosed elsewhere herein or known in the art. For example, the male-fertility polynucleotides disclosed herein may be stacked with any other polynucleotides encoding male-gamete-disruptive polynucleotides or polypeptides, cytotoxins, markers, or other male fertility sequences as disclosed elsewhere herein or known in the art. The stacked polynucleotides may be operably linked to the same promoter as the male-fertility polynucleotide, or may be operably linked to a separate promoter polynucleotide.

As described elsewhere herein, expression cassettes may comprise a promoter operably linked to a polynucleotide of interest, along with a corresponding termination region. The termination region may be native to the transcriptional initiation region, may be native to the operably linked male-fertility polynucleotide of interest or to the male-fertility promoter sequences, may be native to the plant host, or may be derived from another source (i.e., foreign or heterologous). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides of interest may be optimized for increased expression in the transformed plant. That is, the polynucleotides can be synthesized or altered to use plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In particular embodiments, the expression cassettes disclosed herein comprise a promoter operably linked to a male-fertility polynucleotide, or fragment or variant thereof, as disclosed herein. In certain embodiments, a male-fertility promoter is operably linked to a male-fertility polynucleotide disclosed herein, such as the male-fertility polynucleotide set forth in SEQ ID NO: 1, 2, 4, 7, 42, 43, 44, or 45, or an active fragment or variant thereof.

In certain embodiments, plant promoters can preferentially initiate transcription in certain tissues, such as stamen, anther, filament, and pollen, or developmental growth stages, such as sporogenous tissue, microspores, and microgametophyte. Such plant promoters are referred to as "tissue-preferred," "cell-type-preferred," or "growth-stage preferred." Promoters which initiate transcription only in certain tissue are referred to as "tissue-specific." Likewise, promoters which initiate transcription only at certain growth stages are referred to as "growth-stage-specific." A "cell-type-specific" promoter drives expression only in certain cell types in one or more organs, for example, stamen cells, or individual cell types within the stamen such as anther, filament, or pollen cells.

A "male-fertility promoter" may initiate transcription exclusively or preferentially in a cell or tissue involved in the process of microsporogenesis or microgametogenesis. Male-fertility polynucleotides disclosed herein, and active fragments and variants thereof, can be operably linked to male-tissue-specific or male-tissue-preferred promoters including, for example, stamen-specific or stamen-preferred promoters, anther-specific or anther-preferred promoters, pollen-specific or pollen-preferred promoters, tapetum-specific promoters or tapetum-preferred promoters, and the like. Promoters can be selected based on the desired outcome. For example, the polynucleotides of interest can be operably linked to constitutive, tissue-preferred, growth stage-preferred, or other promoters for expression in plants.

In one embodiment, the promoters may be those which express an operably-linked polynucleotide of interest exclusively or preferentially in the male tissues of the plant. No particular male-fertility tissue-preferred or tissue-specific promoter must be used in the process; and any of the many such promoters known to one skilled in the art may be employed. One such promoter is the 5126 promoter, which preferentially directs expression of the polynucleotide to which it is linked to male tissue of the plants, as described in U.S. Pat. Nos. 5,837,851 and 5,689,051. Other examples include the maize Ms45 promoter described at U.S. Pat. No. 6,037,523; SF3 promoter described at U.S. Pat. No. 6,452,069; the BS92-7 promoter described at WO 02/063021; an SGB6 regulatory element described at U.S. Pat. No. 5,470,359; the TA29 promoter (Koltunow, et al., (1990) Plant Cell 2:1201-1224; Nature 347:737 (1990); Goldberg, et al., (1993) Plant Cell 5:1217-1229 and U.S. Pat. No. 6,399,856); an SB200 gene promoter (WO 2002/26789), a PG47 gene promoter (U.S. Pat. Nos. 5,412,085; 5,545,546; Plant J 3(2):261-271 (1993)), a G9 gene promoter (U.S. Pat. Nos. 5,837,850; 5,589,610); the type 2 metallothionein-like gene promoter (Charbonnel-Campaa, et al., Gene (2000) 254: 199-208); the *Brassica* Bca9 promoter (Lee, et al., (2003) Plant Cell Rep. 22:268-273); the ZM13 promoter (Hamilton, et al., (1998) Plant Mol. Biol. 38:663-669); actin depolymerizing factor promoters (such as Zmabp1, Zmabp2; see, for example Lopez, et al., (1996) Proc. Natl. Acad. Sci. USA 93:7415-7420); the promoter of the maize pectin methylesterase-like gene, ZmC5 (Wakeley, et al., (1998) Plant Mol. Biol. 37:187-192); the profilin gene promoter Zmprol (Kovar, et al., (2000) The Plant Cell 12:583-598); the sulphated pentapeptide phytosulphokine gene ZmPSK1 (Lorbiecke, et al., (2005) Journal of Experimental Botany 56(417):1805-1819); the promoter of the calmodulin binding protein Mpcbp (Reddy, et al., (2000) J. Biol. Chem. 275(45):35457-70).

As disclosed herein, constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

"Seed-preferred" promoters include both those promoters active during seed development, such as promoters of seed storage proteins, as well as those promoters active during seed germination. See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also WO 00/12733, where seed-preferred promoters from end1 and end2 genes are disclosed. Additional embryo specific promoters are disclosed in Sato et al. (1996) Proc. Natl. Acad. Sci. 93:8117-8122; Nakase et al. (1997) Plant J 12:235-46; and Postma-Haarsma et al. (1999) Plant Mol. Biol. 39:257-71. Additional endosperm specific promoters are disclosed in Albani et al. (1984) EMBO 3:1405-15; Albani et al. (1999) Theor. Appl. Gen. 98:1253-62; Albani et al. (1993) Plant J. 4:343-55; Mena et al. (1998) The Plant Journal 116:53-62, and Wu et al. (1998) Plant Cell Physiology 39:885-889.

Dividing cell or meristematic tissue-preferred promoters have been disclosed in Ito et al. (1994) Plant Mol. Biol. 24:863-878; Reyad et al. (1995) Mo. Gen. Genet. 248:703-711; Shaul et al. (1996) Proc. Natl. Acad. Sci. 93:4868-4872; Ito et al. (1997) Plant J. 11:983-992; and Trehin et al. (1997) Plant Mol. Biol. 35:667-672.

Stress inducible promoters include salt/water stress-inducible promoters such as PSCS (Zang et al. (1997) Plant Sciences 129:81-89); cold-inducible promoters, such as, cor15a (Hajela et al. (1990) Plant Physiol. 93:1246-1252), cor15b (Wlihelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), ci21A (Schneider et al. (1997) Plant Physiol. 113:335-45); drought-inducible promoters, such as, Trg-31 (Chaudhary et al (1996) Plant Mol. Biol. 30:1247-57), rd29 (Kasuga et al. (1999) Nature Biotechnology 18:287-291); osmotic inducible promoters, such as, Rab 17 (Vilardell et al. (1991) Plant Mol. Biol. 17:985-93) and osmotin (Raghothama et al. (1993) Plant Mol Biol 23:1117-28); and, heat inducible promoters, such as, heat shock proteins (Barros et al. (1992) Plant Mol. 19:665-75; Marrs et al. (1993) Dev. Genet. 14:27-41), and smHSP (Waters et al. (1996) J. Experimental Botany 47:325-338). Other stress-inducible promoters include rip2 (U.S. Pat. No. 5,332,808 and U.S. Publication No. 2003/0217393) and rd29A (Yamaguchi-Shinozaki et al. (1993) Mol. Gen. Genetics 236:331-340).

As discussed elsewhere herein, the expression cassettes comprising male-fertility polynucleotides may be stacked with other polynucleotides of interest. Any polynucleotide of interest may be stacked with the male-fertility polynucleotide, including for example, male-gamete-disruptive polynucleotides and marker polynucleotides.

Male-fertility polynucleotides disclosed herein may be stacked in or with expression cassettes comprising a promoter operably linked to a polynucleotide which is male-gamete-disruptive; that is, a polynucleotide which interferes with the function, formation, or dispersal of male gametes. A male-gamete-disruptive polynucleotide can operate to prevent function, formation, or dispersal of male gametes by any of a variety of methods. By way of example but not limitation, this can include use of polynucleotides which encode a gene product such as DAM-methylase or barnase (See, for example, U.S. Pat. No. 5,792,853 or 5,689,049;

PCT/EP89/00495); encode a gene product which interferes with the accumulation of starch, degrades starch, or affects osmotic balance in pollen, such as alpha-amylase (See, for example, U.S. Pat. Nos. 7,875,764; 8,013,218; 7,696,405, 8,614,367); inhibit formation of a gene product important to male gamete function, formation, or dispersal (See, for example, U.S. Pat. Nos. 5,859,341; 6,297,426); encode a gene product which combines with another gene product to prevent male gamete formation or function (See, for example, U.S. Pat. Nos. 6,162,964; 6,013,859; 6,281,348; 6,399,856; 6,248,935; 6,750,868; 5,792,853); are antisense to, or cause co-suppression of, a gene critical to male gamete function, formation, or dispersal (See, for example, U.S. Pat. Nos. 6,184,439; 5,728,926; 6,191,343; 5,728,558; 5,741,684); interfere with expression of a male-fertility polynucleotide through use of hairpin formations (See, for example, Smith et al. (2000) Nature 407:319-320; WO 99/53050 and WO 98/53083) or the like.

Male-gamete-disruptive polynucleotides include dominant negative genes such as methylase genes and growth-inhibiting genes. See, U.S. Pat. No. 6,399,856. Dominant negative genes include diphtheria toxin A-chain gene (Czako and An (1991) Plant Physiol. 95 687-692; Greenfield et al. (1983) PNAS 80:6853); cell cycle division mutants such as CDC in maize (Colasanti et al. (1991) PNAS 88: 3377-3381); the WT gene (Farmer et al. (1994) Mol. Genet. 3:723-728); and P68 (Chen et al. (1991) PNAS 88:315-319).

Further examples of male-gamete-disruptive polynucleotides include, but are not limited to, pectate lyase gene pelE from *Erwinia chrysanthermi* (Kenn et al (1986) J. Bacteriol. 168:595); CytA toxin gene from *Bacillus thuringiensis* Israeliensis (McLean et al (1987) J. Bacteriol. 169:1017 (1987), U.S. Pat. No. 4,918,006); DNAses, RNAses, proteases, or polynucleotides expressing anti-sense RNA. A male-gamete-disruptive polynucleotide may encode a protein involved in inhibiting pollen-stigma interactions, pollen tube growth, fertilization, or a combination thereof.

Male-fertility polynucleotides disclosed herein may be stacked with expression cassettes disclosed herein comprising a promoter operably linked to a polynucleotide of interest encoding a reporter or marker product. Examples of suitable reporter polynucleotides known in the art can be found in, for example, Jefferson et al. (1991) in Plant Molecular Biology Manual, ed. Gelvin et al. (Kluwer Academic Publishers), pp. 1-33; DeWet et al. Mol. Cell. Biol. 7:725-737 (1987); Goff et al. EMBO J. 9:2517-2522 (1990); Kain et al. BioTechniques 19:650-655 (1995); and Chiu et al. Current Biology 6:325-330 (1996). In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate, and phosphinothricin.

In some embodiments, the expression cassettes disclosed herein comprise a polynucleotide of interest encoding scorable or screenable markers, where presence of the polynucleotide produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase, and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments, such as the maize C1 and C2, the B gene, the p1 gene, and the bronze locus genes, among others. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP), and DsRed2 (Clontech Laboratories, Inc., Mountain View, Calif.), where plant cells transformed with the marker gene fluoresce red in color, and thus are visually selectable. Additional examples include a p-lactamase gene encoding an enzyme for which various chromogenic substrates are known (e.g., PADAC, a chromogenic cephalosporin), a xylE gene encoding a catechol dioxygenase that can convert chromogenic catechols, and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the compositions and methods disclosed herein.

In some embodiments, the expression cassettes disclosed herein comprise a first polynucleotide of interest encoding a male-fertility polynucleotide operably linked to a first promoter polynucleotide, stacked with a second polynucleotide of interest encoding a male-gamete-disruptive gene product operably linked to a male-tissue-preferred promoter polynucleotide. In certain embodiments, the expression cassettes described herein may also be stacked with a third polynucleotide of interest encoding a marker polynucleotide operably linked to a promoter polynucleotide.

In specific embodiments, the expression cassettes disclosed herein comprise a first polynucleotide of interest encoding a male fertility gene disclosed herein, such as wheat or barley Ms1 operably linked to a constitutive promoter, such as the cauliflower mosaic virus (CaMV) 35S promoter. The expression cassettes may further comprise a second polynucleotide of interest encoding a male-gamete-disruptive gene product operably linked to a male-tissue-preferred promoter. In certain embodiments, the expression cassettes disclosed herein may further comprise a third polynucleotide of interest encoding a marker gene, such as the phosphinothricin acetyltransferase (PAT) gene from Streptomyces viridochomagenes operably linked to a constitutive promoter, such as the cauliflower mosaic virus (CaMV) 35S promoter.

IV. Plants

A. Plants Having Altered Levels/Activity of Male-Fertility Polypeptide

Further provided are plants having altered levels and/or activities of a male-fertility polypeptide and/or altered levels of male fertility. In some embodiments, the plants disclosed herein have stably incorporated into their genomes a heterologous male-fertility polynucleotide, or an active fragment or variant thereof, as disclosed herein. Thus, plants, plant cells, plant parts, and seeds are provided which comprise at least one heterologous male-fertility polynucleotide as set forth in any one of SEQ ID NO: 1, 2, 4, 7, 42, 43, 44, or 45 or any active fragments or variants thereof.

Plants are further provided comprising the expression cassettes disclosed herein comprising a male-fertility polynucleotide operably linked to a promoter that is active in the plant. In some embodiments, expression of the male-fertility polynucleotide modulates male fertility of the plant. In certain embodiments, expression of the male-fertility polynucleotide increases male fertility of the plant. For example, plants are provided comprising an expression cassette comprising an Ms1 polynucleotide as set forth in SEQ ID NO: 1, 2, 4, 7, 42, 43, 44, or 45, or an active fragment or variant thereof, operably linked to a constitutive promoter, such as the CaMV 35S promoter. Upon expression of the Ms1 polynucleotide, male fertility of the plant is increased.

In certain embodiments, expression cassettes comprising a heterologous male-fertility polynucleotide as disclosed herein, or an active fragment or variant thereof, operably linked to a promoter active in a plant, are provided to a male-sterile plant. Upon expression of the heterologous male-fertility polynucleotide, male fertility is conferred; this may be referred to as restoring the male fertility of the plant. In specific embodiments, the plants disclosed herein comprise an expression cassette comprising a heterologous male-fertility polynucleotide as disclosed herein, or an active fragment or variant thereof, operably linked to a promoter, stacked with one or more expression cassettes comprising a polynucleotide of interest operably linked to a promoter active in the plant. For example, the stacked polynucleotide of interest can comprise a male-gamete-disruptive polynucleotide and/or a marker polynucleotide.

Plants disclosed herein may also comprise stacked expression cassettes described herein comprising at least two polynucleotides such that the at least two polynucleotides are inherited together in more than 50% of meioses, i.e., not randomly. Accordingly, when a plant or plant cell comprising stacked expression cassettes with two polynucleotides undergoes meiosis, the two polynucleotides segregate into the same progeny (daughter) cell. In this manner, stacked polynucleotides will likely be expressed together in any cell for which they are present. For example, a plant may comprise an expression cassette comprising a male-fertility polynucleotide stacked with an expression cassette comprising a male-gamete-disruptive polynucleotide such that the male-fertility polynucleotide and the male-gamete-disruptive polynucleotide are inherited together. Specifically, a male sterile plant could comprise an expression cassette comprising a male-fertility polynucleotide disclosed herein operably linked to a constitutive promoter, stacked with an expression cassette comprising a male-gamete-disruptive polynucleotide operably linked to a male-tissue-preferred promoter, such that the plant produces mature pollen grains. However, in such a plant, development of pollen comprising the male-fertility polynucleotide will be inhibited by expression of the male-gamete-disruptive polynucleotide.

B. Plants and Methods of Introduction

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, by "grain" is intended the mature seed produced by commercial growers for purposes other than growing or reproducing the species. Progeny, variants, and mutants of the regenerated plants are also included within the scope of the disclosure, provided that these parts comprise the introduced nucleic acid sequences.

The methods disclosed herein comprise introducing a polypeptide or polynucleotide into a plant cell. "Introducing" is intended to mean presenting to the plant the polynucleotide or polypeptide in such a manner that the sequence gains access to the interior of a cell. The methods disclosed herein do not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide or polypeptide is introduced into the host (i.e., a plant) and expressed temporally.

Transformation protocols as well as protocols for introducing polypeptides or polynucleotide sequences into plants may vary depending on the type of plant or plant cell, e.g., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agro-*

*bacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium* tumefaciens); all of which are herein incorporated by reference.

In specific embodiments, the male-fertility polynucleotides or expression cassettes disclosed herein can be provided to a plant using a variety of transient transformation methods. Such transient transformation methods include, but are not limited to, the introduction of the male-fertility polypeptide or variants and fragments thereof directly into the plant or the introduction of a male fertility transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the male-fertility polynucleotide or expression cassettes disclosed herein can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the male-fertility polynucleotides or expression cassettes disclosed herein may be introduced into plants by contacting plants with a virus or viral nucleic acids. Generally, such methods involve incorporating a nucleotide construct disclosed herein within a viral DNA or RNA molecule. It is recognized that a male fertility sequence disclosed herein may be initially synthesized as part of a viral polyprotein, which later may be processed by proteolysis in vivo or in vitro to produce the desired recombinant protein. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, a polynucleotide disclosed herein can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be pollinated with either the same transformed strain or a different strain, and the resulting progeny having desired expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a male-fertility polynucleotide disclosed herein, for example, an expression cassette disclosed herein, stably incorporated into their genome.

The terms "target site", "target sequence", "target DNA", "target locus", "genomic target site", "genomic target sequence", and "genomic target locus" are used interchangeably herein and refer to a polynucleotide sequence in the genome (including chloroplast and mitochondrial DNA) of a cell at which a double-strand break is induced in the cell genome. The target site can be an endogenous site in the genome of a cell or organism, or alternatively, the target site can be heterologous to the cell or organism and thereby not be naturally occurring in the genome, or the target site can be found in a heterologous genomic location compared to where it occurs in nature. As used herein, terms "endogenous target sequence" and "native target sequence" are used interchangeably herein to refer to a target sequence that is endogenous or native to the genome of a cell or organism and is at the endogenous or native position of that target sequence in the genome of a cell or organism. Cells include plant cells as well as plants and seeds produced by the methods described herein.

In one embodiments, the target site, in association with the particular gene editing system that is being used, can be similar to a DNA recognition site or target site that is specifically recognized and/or bound by a double-strand-break-inducing agent, such as but not limited to a Zinc Finger endonuclease, a meganuclease, a TALEN endonuclease, a CRISPR-Cas guideRNA or other polynucleotide guided double strand break reagent.

The terms "artificial target site" and "artificial target sequence" are used interchangeably herein and refer to a target sequence that has been introduced into the genome of a cell or organism. Such an artificial target sequence can be identical in sequence to an endogenous or native target sequence in the genome of a cell but be located in a different position (i.e., a non-endogenous or non-native position) in the genome of a cell or organism.

The terms "altered target site", "altered target sequence", "modified target site", and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii). For example, the point mutations of ms1d, ms1e, ms1f, or ms1h have been shown to result in male sterility; similar mutations could be directed within the exons of Ms1 to provide alternative alleles resulting in male sterility. Also, multiple mutations could be used in combination.

Certain embodiments comprise polynucleotides disclosed herein which are modified using endonucleases. Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Endonucleases also include meganucleases, also known as homing endonucleases (HEases). Like restriction endonucleases, HEases bind and cut at a specific recognition site. However, the recognition sites for meganucleases are typically longer, about 18 bp or more. (See patent publication WO2012/129373 filed on Mar. 22, 2012). Meganucleases have been classified into four families based on conserved sequence motifs (Belfort M, and Perlman P S J. Biol. Chem. 1995; 270:30237-30240). These motifs participate in the coordination of metal ions and hydrolysis of phosphodiester bonds. HEases are notable for their long recognition sites, and for tolerating some sequence polymorphisms in their DNA substrates.

The naming convention for meganucleases is similar to the convention for other restriction endonuclease. Meganucleases are also characterized by prefix F—, I—, or PI— for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr. Op. Biotechnol. 5:521-7; and Sadowski (1993) FASEB 7:760-7. In some examples the recombinase is from the Integrase or Resolvase families.

TAL effector nucleases are a class of sequence-specific nucleases that can be used to make double-strand breaks at specific target sequences in the genome of a plant or other organism. (Miller et al. (2011) Nature Biotechnology 29:143-148). Zinc finger nucleases (ZFNs) are engineered double-strand-break-inducing agents comprised of a zinc finger DNA binding domain and a double-strand-break-inducing agent domain. Recognition site specificity is conferred by the zinc finger domain, which typically comprises two, three, or four zinc fingers, for example having a C2H2 structure; however other zinc finger structures are known and have been engineered. Zinc finger domains are amenable for designing polypeptides which specifically bind a selected polynucleotide recognition sequence. ZFNs include engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognizes a sequence of 9 contiguous nucleotides; with a dimerization requirement of the nuclease, two sets of zinc finger triplets are used to bind an 18-nucleotide recognition sequence.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR—repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in E. coli (Ishino et al. (1987) J. Bacteriol. 169:5429-5433; Nakata et al. (1989) J. Bacteriol. 171:3553-3556). Similar interspersed short sequence repeats have been identified in Haloferax mediterranei, Streptococcus pyogenes, Anabaena, and Mycobacterium tuberculosis (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene relates to a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. Provisional Application No. 62/023,239, filed Jul. 11, 2014). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

The Cas endonuclease gene can be Cas9 endonuclease, or a functional fragment thereof, such as but not limited to, Cas9 genes listed in SEQ ID NOs: 462, 474, 489, 494, 499, 505, and 518 of WO2007/025097 published Mar. 1, 2007. The Cas endonuclease gene can be a plant, maize or soybean optimized Cas9 endonuclease, such as but not limited to a plant codon optimized *Streptococcus pyogenes* Cas9 gene that can recognize any genomic sequence of the form N(12-30)NGG. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. Provisional Application No. 62/023,239, filed Jul. 11, 2014). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA- combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9,10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In certain embodiments the nucleotide sequence to be modified can be a regulatory sequence such as a promoter, wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers; see e.g. U.S. Pat. No. 5,837,850 issued Nov. 17, 1998), a mutation of DNA binding elements and/or deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or SulphonylUrea (Su) repressor/operator/inducer elements. The dehydration-responsive element (DRE) was first identified as a cis-acting promoter element in the promoter of the droughtresponsive gene rd29A, which contains a 9 bp conserved core sequence, TACCGACAT (Yamaguchi-Shinozaki, K., and Shinozaki, K. (1994) *Plant Cell* 6, 251 264). Insertion of DRE into an endogenous promoter may confer a drought inducible expression of the downstream gene. Another example is ABA-responsive elements (ABREs) which contain a (C/T)ACGTGGC consensus sequence found to be present in numerous ABA and/or stress-regulated genes (Busk P. K., Pages M. (1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

The male-fertility polynucleotides and expression cassettes disclosed herein may be used for transformation of any plant species, including, but not limited to, monocots and dicots. Examples of plant species of interest include, but are not limited to, corn/maize (*Zea mays*), Brassica sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (for species, see below), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, grasses and conifers.

In particular embodiments, wheat plants are used in the methods and compositions disclosed herein. As used herein, the term "wheat" refers to any species of the genus Triticum, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. mocha, T. compactum, T. sphaerococcum, T. vavilovii*, and interspecies cross thereof. Tetraploid wheat includes *T. durum* (also referred to as durum wheat or *Triticum turgidum* ssp. durum), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present disclosure may belong to, but is not limited to, any of the above-listed species. Also encompassed are plants that are produced by conventional techniques using *Triticum* sp. as a parent in a sexual cross with a non-Triticum species, such as rye (*Secale cereale*), including but not limited to Triticale. In some embodiments, the wheat plant is suitable for commercial production of grain, such as commercial varieties of hexaploid wheat or durum wheat, having suitable agronomic characteristics which are known to those skilled in the art.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present methods and compositions include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants disclosed herein are crop plants (for example, corn, alfalfa, sunflower, *Brassica*, soybean, cotton, safflower, peanut, sorghum, wheat, millet, tobacco, etc.). Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of the methods and compositions disclosed herein to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the *beta* lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein disclosed herein are available using *Bacillus* sp. and *Salmonella* (Palva et al. (1983) *Gene* 22:229-235); Mosbach et al. (1983) *Nature* 302:543-545).

In some embodiments, the expression cassette or male-fertility polynucleotides disclosed herein are maintained in a hemizygous state in a plant. Hemizygosity is a genetic condition existing when there is only one copy of a gene (or set of genes) with no allelic counterpart. In certain embodiments, an expression cassette disclosed herein comprises a first promoter operably linked to a male-fertility polynucleotide which is stacked with a male-gamete-disruptive polynucleotide operably linked to a male-tissue-preferred promoter, and such expression cassette is introduced into a male-sterile plant in a hemizygous condition. When the male-fertility polynucleotide is expressed, the plant is able to successfully produce mature pollen grains because the male-fertility polynucleotide restores the plant to a fertile condition. Given the hemizygous condition of the expression cassette, only certain daughter cells will inherit the expression cassette in the process of pollen grain formation. The daughter cells that inherit the expression cassette containing the male-fertility polynucleotide will not develop into mature pollen grains due to the male-tissue-preferred expression of the stacked encoded male-gamete-disruptive gene product. Those pollen grains that do not inherit the expression cassette will continue to develop into mature pollen grains and be functional, but will not contain the male-fertility polynucleotide of the expression cassette and therefore will not transmit the male-fertility polynucleotide to progeny through pollen.

V. Modulating the Concentration and/or Activity of Male-Fertility Polypeptides

A method for modulating the concentration and/or activity of the male-fertility polypeptides disclosed herein in a plant is provided. The term "influences" or "modulates," as used herein with reference to the concentration and/or activity of the male-fertility polypeptides, refers to any increase or decrease in the concentration and/or activity of the male-fertility polypeptides when compared to an appropriate control. In general, concentration and/or activity of a male-fertility polypeptide disclosed herein is increased or decreased by at least 1%, 5%, 10%, 20%, 30%, 40%, 50%, 60%, 70%, 80%, or 90% relative to a control plant, plant part, or cell. Modulation as disclosed herein may occur before, during and/or subsequent to growth of the plant to a particular stage of development. In specific embodiments, the male-fertility polypeptides disclosed herein are modulated in monocots, particularly wheat.

A variety of methods can be employed to assay for modulation in the concentration and/or activity of a male-fertility polypeptide. For instance, the expression level of the male-fertility polypeptide may be measured directly, for example, by assaying for the level of the male-fertility polypeptide or RNA in the plant (i.e., Western or Northern blot), or indirectly, for example, by assaying the male-fertility activity of the male-fertility polypeptide in the plant. Methods for measuring the male-fertility activity are described elsewhere herein or known in the art. In specific embodiments, modulation of male-fertility polypeptide concentration and/or activity comprises modulation (i.e., an increase or a decrease) in the level of male-fertility polypeptide in the plant. Methods to measure the level and/or activity of male-fertility polypeptides are known in the art and are discussed elsewhere herein. In still other embodiments, the level and/or activity of the male-fertility polypeptide is modulated in vegetative tissue, in reproductive tissue, or in both vegetative and reproductive tissue.

In one embodiment, the activity and/or concentration of the male-fertility polypeptide is increased by introducing the polypeptide or the corresponding male-fertility polynucleotide into the plant. Subsequently, a plant having the introduced male-fertility sequence is selected using methods known to those of skill in the art such as, but not limited to, Southern blot analysis, DNA sequencing, PCR analysis, or phenotypic analysis. In certain embodiments, marker polynucleotides are introduced with the male-fertility polynucleotide to aid in selection of a plant having or lacking the male-fertility polynucleotide disclosed herein. A plant or plant part altered or modified by the foregoing embodiments is grown under plant-forming conditions for a time sufficient to modulate the concentration and/or activity of the male-fertility polypeptide in the plant. Plant-forming conditions are well known in the art.

As discussed elsewhere herein, many methods are known in the art for providing a polypeptide to a plant including, but not limited to, direct introduction of the polypeptide into the plant, or introducing into the plant (transiently or stably) a polynucleotide construct encoding a male-fertility polypeptide. It is also recognized that the methods disclosed herein may employ a polynucleotide that is not capable of directing, in the transformed plant, the expression of a protein or an RNA. The level and/or activity of a male-fertility polypeptide may be increased, for example, by altering the gene encoding the male-fertility polypeptide or its promoter. See, e.g., Kmiec, U.S. Pat. No. 5,565,350; Zarling et al., PCT/US93/03868. Therefore mutagenized plants that carry mutations in male fertility genes, where the mutations modulate expression of the male fertility gene or modulate the activity of the encoded male-fertility polypeptide, are provided.

In certain embodiments, the concentration and/or activity of a male-fertility polypeptide is increased by introduction into a plant of an expression cassette comprising a male-fertility polynucleotide (e.g. SEQ ID NO: 1, 2, 4, 7, 42, 43, 44, or 45, or an active fragment or variant thereof), as disclosed elsewhere herein. The male-fertility polynucleotide may be operably linked to a promoter that is heterologous to the plant or native to the plant. By increasing the concentration and/or activity of a male-fertility polypeptide in a plant, the male fertility of the plant is likewise increased.

Thus, the male fertility of a plant can be increased by increasing the concentration and/or activity of a male-fertility polypeptide. For example, male fertility can be restored to a male-sterile plant by increasing the concentration and/or activity of a male-fertility polypeptide.

It is also recognized that the level and/or activity of the polypeptide may be modulated by employing a polynucleotide that is not capable of directing, in a transformed plant, the expression of a protein or an RNA. For example, the polynucleotides disclosed herein may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778, herein incorporated by reference. In some embodiments, virus-induced gene silencing may be employed; see, for example, Ratcliff et al. (2001) *Plant J.* 25:237-245; Dinesh-Kumar et al. (2003) *Methods Mol. Biol.* 236:287-294; Lu et al. (2003) *Methods* 30:296-303; Burch-Smith et al. (2006) *Plant Physiol.* 142:21-27. It is therefore recognized that methods disclosed herein do not depend on the incorporation of the entire polynucleotide into the genome, only that the plant or cell thereof is altered as a result of the introduction of the polynucleotide into a cell.

In other embodiments, the level and/or activity of the polypeptide may be modulated by methods which do not require introduction of a polynucleotide into the plant, such as by exogenous application of dsRNA to a plant surface; see, for example, WO 2013/025670.

In one embodiment, the genome may be altered following the introduction of the polynucleotide into a cell. For example, the polynucleotide, or any part thereof, may incorporate into the genome of the plant. Alterations to the genome disclosed herein include, but are not limited to, additions, deletions, and substitutions of nucleotides into the genome. While the methods disclosed herein do not depend on additions, deletions, and substitutions of any particular number of nucleotides, it is recognized that such additions, deletions, or substitutions comprise at least one nucleotide.

VI. Definitions

The term "allele" refers to one of two or more different nucleotide sequences that occur at a specific locus.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

A "BAC", or bacterial artificial chromosome, is a cloning vector derived from the naturally occurring F factor of *Escherichia coli*, which itself is a DNA element that can exist as a circular plasmid or can be integrated into the bacterial chromosome. BACs can accept large inserts of DNA sequence.

A "centimorgan" ("cM") is a unit of measure of recombination frequency. One cM is equal to a 1% chance that a marker at one genetic locus will be separated from a marker at a second locus due to crossing over in a single generation.

A "chromosome" is a single piece of coiled DNA containing many genes that act and move as a unit during cell division and therefore can be said to be linked. It can also be referred to as a "linkage group".

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (i.e., their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, HRM, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genome" refers to the total DNA, or the entire set of genes, carried by a chromosome or chromosome set.

The term "genotype" is the genetic constitution of an individual (or group of individuals) defined by the allele(s) of one or more known loci that the individual has inherited from its parents. More generally, the term genotype can be used to refer to an individual's genetic make-up for all the genes in its genome.

A "locus" is a position on a chromosome, e.g. where a nucleotide, gene, sequence, or marker is located.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus refers to the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected eg via DNA sequencing, PCR-based sequence specific amplification methods, detection of polynucleotide polymorphisms by allele specific hybridization (ASH), dynamic allele-specific hybridization (DASH), Competitive Allele-Specific Polymerase chain reaction (KASPar), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology have the advantage of being able to detect a series of linked SNP alleles that constitute a haplotype. Haplotypes tend to be more informative (detect a higher level of polymorphism) than SNPs.

A "marker allele", alternatively an "allele detected by a marker" or "an allele at a marker locus", can refer to one or a plurality of polymorphic nucleotide sequences found at a marker locus in a population.

A "marker locus" is a specific chromosome location in the genome of a species detected by a specific marker. A marker locus can be used to track the presence of a second linked locus, e.g., one that affects the expression of a phenotypic trait. For example, a marker locus can be used to monitor segregation of alleles at a genetically or physically linked locus, such as a QTL.

A "marker probe" is a nucleic acid sequence or molecule that can be used to identify the presence of an allele at a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus. Nucleic acids are "complementary" when they specifically "hybridize", or pair, in solution, e.g., according to Watson-Crick base pairing rules.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA between 2 or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "reference sequence" or a "consensus sequence" is a defined sequence used as a basis for sequence comparison.

TABLE 1

Summary of SEQ ID NOS

| SEQ ID: | Description |
|---|---|
| 1 | Barley Ms1 genomic region sequence including promoter region at positions 1-902 |
| 2 | Barley Ms1 coding sequence |
| 3 | Barley MS1 amino acid sequence |
| 4 | Wheat Ms1 coding sequence |
| 5 | Wheat MS1 amino acid sequence |
| 6 | Wheat Ms1 promoter sequence |
| 7 | Wheat Ms1 wildtype genomic sequence including 3'UTR at positions 3381-4335 |
| 8 | Wheat Ms1 variant promoter sequence |
| 9 | Wheat Ms1 variant genomic sequence |
| 10 | Syntenic *Hordeum vulgare* reference sequence for marker 11_21056 |
| 11 | *Triticum aestivum* reference sequence for marker 21056 |
| 12 | *Triticum aestivum* reference sequence of cultivar Gladius for marker 21056 |
| 13 | *Triticum aestivum* reference sequence of cultivar Chris for marker 21056 |
| 14 | *Aegilops speltoides* EST reference sequence for marker BF292015 |
| 15 | *Triticum aestivum* reference sequence for marker BF292015 |
| 16 | *Triticum aestivum* reference sequence of cultivar Gladius for marker BF292015 |
| 17 | *Triticum aestivum* reference sequence of cultivar Chris for marker BF292015 |
| 18 | *Triticum aestivum* reference sequence for marker wsnp_Ex_c18318_27140346 |
| 19 | *Triticum aestivum* reference sequence of cultivar Gladius for marker wsnp_Ex_c18318_27140346 |
| 20 | *Triticum aestivum* reference sequence of cultivar Chris for marker wsnp_Ex_c18318_27140346 |
| 21 | *Triticum aestivum* reference sequence for marker wsnp_Ku_c7153_12360198 |
| 22 | *Triticum aestivum* reference sequence of cultivar Gladius for marker wsnp_Ku_c7153_12360198 |
| 23 | *Triticum aestivum* reference sequence of cultivar Chris for marker wsnp_Ku_c7153_12360198 |
| 24 | ET0487 amplicon |
| 25 | ET0488 amplicon |
| 26 | ET0489 amplicon |
| 27 | ET0490 amplicon |
| 28 | ET0491 amplicon |
| 29 | ET0495 amplicon |
| 30 | *Zea mays* alpha-amylase polynucleotide |
| 31 | *Zea mays* alpha-amylase polypeptide |
| 32 | Flanking marker 007-0033.1 amplicon |
| 33 | Flanking marker 007-0046.1 amplicon |
| 34 | ET0292 amplicon; 007-0009.1 |
| 35 | ET0294 amplicon; 007-0011.1 |

TABLE 1-continued

Summary of SEQ ID NOS

| SEQ ID: | Description |
|---|---|
| 36 | 007-0042.1 (4BS 48995435030) |
| 37 | 007-0182.1 |
| 38 | TaLTPG1 3'UTR fragment for RNAi |
| 39 | *Brachypodium distachyon* MS1 amino acid sequence |
| 40 | *Oryza sativa* MS1 amino acid sequence |
| 41 | Barley Ms1 promoter |
| 42 | *Oryza* Ms1 genomic region |
| 43 | *Oryza* Ms1 coding sequence |
| 44 | *Brachypodium* Ms1 genomic region |
| 45 | *Brachypodium* Ms1 coding sequence |
| 46 | Wheat Ms1 terminator region (see also positions 3384-4335 of SEQ ID NO: 7) |
| 47 | Barley Ms1 terminator region (see also positions 2838-3838 of SEQ ID NO: 1) |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this disclosure pertains, and all such publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Genetic Mapping of Ms1

This example demonstrates that by using recombinant mapping populations of wild-type and male-sterile wheat, the causative locus for the male-sterile phenotype of wheat ms1 can be mapped to a 1 cM region on the short arm of chromosome 4 of the B genome. A male sterile (msms) alloplasmic wheat, var. Chris, carrying the FS2 mutant gene (also referred to as ms1d) was crossed to a plant of variety Gladius to create an $F_2$ mapping population. Sequences in the Ms1 region on chromosome 4B S were identified based either on synteny with wheat chromosome 4AL (Hernandez et al. 2011. *Plant Journal* 69(3):377-386), barley chromosome 4HS (Mayer et al. 2011. *Plant Cell* 23(4):1249-1263), *Brachypodium* chromosome 1 and rice chromosome 3, or bin mapped wheat ESTs (Sorrells et al., 2003 *Genome Research* 13:1818-1827; La Rota & Sorrells, 2004 *Funct Integr Genomics* 4: 34-46). Corresponding wheat sequence contigs from reference syntenic sequences (e.g. barley SNP marker 11_21056, for which SEQ ID NO:10 represents a reference sequence) or bin mapped ESTs (e.g. BF292015, for which SEQ ID NO:14 represents a reference sequence) were identified by BLAST to chromosome 4BS-derived IWGSC (International Wheat Genome Sequencing Consortium) survey sequence assemblies (Mayer, 2014 *Science* 345 (6194): 1251788). IWGSC contigs were targeted for High Resolution Melting (HRM) marker development or Insertion Site-Based Polymorphism (ISBP-HRM) marker development. ISBP-HRM primers were designed using the ISBP Finder tool (Paux et al., 2010 *Plant Biotechnology Journal* 8:196-210).

Polymerase chain reaction (PCR) amplification was performed using DNA from the following: the parents of the mapping population, 4B nullisomic lines, and the radiation-induced deletions Probus and Cornerstone. Because genetic and physical mapping studies indicate that Cornerstone and Probus are likely to differ in terminal deletion size and extent of telomere repairing, their comparative analysis was used to identify Ms1 flanking markers (Barlow & Driscoll (1981) *Genetics*. 98(4):791-799; Zhong-an & Darvey (1999) *Acta Agriculturae Boreali-Occidentalis Sinica*. cnki:ISSN:1004-1389.0.1999-04-006). Primers flanking Ms1 were experimentally determined by the absence of PCR products from DNA nullisomic for chromosome 4B and homozygous for the radiation—induced deletion mutant Cornerstone but present for the homozygous radiation—induced deletion mutant Probus. HRM markers that met the above criteria were used for mapping.

Phenotyping for genetic male sterility was performed by securely covering at least three spikes per plant with sealed white paper bags prior to anthesis, and a quantitative fertility score was then determined by counting the number of florets per spike and the number of seeds per spike and expressing the score as the number of seeds per floret formed.

509 $F_2$ individuals were initially screened with markers identified to be flanking the Ms1 region on chromosome 4BS and polymorphic between Chris and Gladius. $F_2$ individuals were assessed phenotypically for genetic male sterility using the procedure described previously. 21 recombinants were identified, and the Ms1 locus was found to be located between the HRM markers 21056 (SEQ ID NO: 11 is the reference sequence) and BF292015 (SEQ ID NO:15 is the reference sequence). HRM markers 21056 and BF292015 were designated to 4BS-derived IWGSC sequence contigs lcl|4BS_4947956 and lcl|4BS_4925422, respectively (Mayer, 2014 Science 345 (6194): 1251788). This region was determined to cover a genetic distance of 14 cM on the 90K consensus map.

Markers were then developed in the region between markers 21056 and BF292015 and tested for their association with the genetic male sterility phenotype. The 9K consensus wheat single-nucleotide polymorphism (SNP) map (Cavanagh et al. 2013 PNAS 110:8057-8062) was used to identify SNP-containing sequences and corresponding IWGSC contigs that were genetically positioned in the Ms1 region on the short arm of chromosome 4BS in wheat (Mayer 2014. *Science* 345(6194):1251788). Either SNP containing sequences or the chromosome 4BS-derived IWGSC contigs were targeted for HRM marker development or insertion site-based polymorphism (ISBP-HRM) marker development. A total of 3000 $F_2$ individuals were screened and 54 recombinants were identified, narrowing the Ms1-containing region to an area bounded by markers wsnp_Ex_c18318_27140346 (SEQ ID NO:18 is the reference sequence) and wsnp_Ku_c7153_12360198 (SEQ ID NO:21 is the reference sequence). Markers wsnp_Ex_c18318_27140346 and wsnp_Ku_c7153_12360198 correspond to 4BS-derived IWGSC sequence contigs lcl|4BS_4920499 and lcl|4BS_4954867 respectively (Mayer, 2014 *Science* 345 (6194): 1251788). This region spans a genetic interval of 0.5 cM based on the 9K consensus wheat SNP map.

Example 2

Identifying 4BS BACs for Sequencing of Ms1

Eighteen probes were designed within the 0.5 cM region bounded by markers wsnp_Ex_c18318_27140346 (SEQ ID NO:18) and wsnp_Ku_c7153_12360198 (SEQ ID NO:21), using synteny to Brachypodium and rice. Probes were designed to be non-repetitive based on BLAST analysis of target sequences. Probes were then PCR amplified and separated by agarose gel electrophoresis with fragments of desired size being eluted from the gel using Qiaquick Gel Extraction kit (Qiagen, Germantown, Md., USA). PCR fragments were pooled to an equimolar concentration then 32P-dATP radio-labeled by NEBlot kit (New England Biolabs) using manufacturer's protocol. The labeled probe was purified in a Sephadex G50 column (GE Healthcare) and denatured at 100° C. for 10 min. Twenty eight high-density BAC clone colony filters gridded onto Hybond N+nylon membranes (GE Healthcare, Piscataway, N.J., USA) were used for hybridization. This represents a coverage of 5.1-genome equivalents from the durum wheat variety Langdon (Cenci et al. 2003. *Theor Appl Genet* 107(5):931-9). For prehybridization, overnight incubation of colony filters in hybridization solution (2× SSPE, 0.5% SDS, 5×Denhardt's reagent (Sambrook & Russel (2001) *Molecular Cloning: A Laboratory Manual*, Cold Spring Harbor Laboratory Press, New York, N.Y., USA), 40 µg/ml salmon sperm DNA) was done in rotary glass tubes at 65° C. The labeled probe was mixed with 5 ml of hybridization solution and colony filters were incubated at 65° C. overnight. To remove the unbound probe, filters were washed twice in washing solution containing 2× SSPE and 0.5% SDS and rinsed with 1× SSC. The washed filters were exposed to X-ray film for one to three days based on the signal intensity to identify positive clones. Šimková (2011) Journal of Biomedicine and Biotechnology. http://dx.doi.org/10.1155/2011/302543. These probes identified public BACs spanning the Ms1 region.

BACs that gave a positive signal were isolated from the plates. Restriction mapping, PCR experiments with primers corresponding to the markers previously used, and sequences obtained from the ends of each BAC were used to determine the order of the BACs covering the region of interest. Three BACs from the Langdon library that spanned the Ms1 region, representing 251 kB, were selected for sequencing. In addition, a proprietary BAC was sequenced in order to cover the critical region. These BACs were sequenced using standard shotgun sequencing techniques and the sequences assembled using the Phred/Phrap/Consed software package (Ewing et al. (1998) *Genome Research*, 8:175-185). After assembly, the sequences thought to be in the region closest to the locus on the basis of the mapping data were annotated, meaning that possible gene-encoding regions and regions representing repetitive elements were deduced. Gene encoding (genic) regions were sought using the fGenesH software package (Softberry, Mount Kisco, N.Y., USA).

Example 3

Identification of Candidate Ms1 Gene

Ten potential coding regions were detected within the 251 kB sequence by mapping cDNAs derived from wheat root, leaf and anther tissues. Table 2 provides the physical position of the 10 likely coding sequences plus their putative peptide function.

TABLE 2

| gene | sequence similarity | coordinates | | orientation | functional annotation (*Brachypodium*) |
|---|---|---|---|---|---|
| 1 | Bradi1g12960.1 | 1 | 1658 | sense | partial gene; unknown |
| 2 | Bradi1g12970.1 | 3748 | 4252 | antisense | N-acetyltransferase |
| 3 | Bradi1g12980.1 | 21867 | 23596 | sense | parafibromin |
| 4 | Bradi1g12990.1 | 26424 | 26660 | antisense | LTPL71 |
| 5 | Bradi1g13000.1 | 28697 | 29260 | antisense | LTPL72 |
| 6 | Bradi4g44760.1 | 30649 | 32207 | antisense | ubiquitin-protein ligase |
| 7 | Bradi1g69240.1 | 30436 | 30612 | sense | Fbox/LRR domain |
| 8 | Bradi1g13030 | 181034 | 181291 | sense | LTPL94 |
| 9 | Bradi2g05445.1 | 210365 | 218154 | antisense | 60S ribosomal protein |
| 10 | Bradi1g13040 | 227961 | 230664 | antisense | globulin—Cupin |

Among the 10 open reading frames, three encoded polypeptides with similarity to non-specific lipid transfer proteins (nsLTPs) (Edstam et al., 2014 *Physiologia Plantarum* doi:10.1111/pp1.12156) were identified. Upon examination of anther transcripts from male sterile homozygous ms1 Cornerstone plants, the cDNA corresponding to SEQ ID NO:4 was not observed. The absence of transcripts from SEQ ID NO: 4 suggests a strong correlation of the ms1 sterility phenotype with this cDNA. This particular sequence is predicted to encode a glycosylphosphatidylinositol (GPI)-anchored nsLTP (LTPG) polypeptide (SEQ ID NO:5 is the amino acid sequence of the encoded protein) and has been named TaLTPG1, also known as Ms1.

Analysis of the Ms1 polypeptide (SEQ ID NO: 5) indicates a signal peptide located at positions 1-23; the LTP domain at positions 24-108; and a GPI anchor domain at positions 195-220. Structural modeling using the primary polypeptide sequence indicates that a hydrophobic pocket formed within the LTP domain by disulfide bridges (Cys-Cys) is likely to bind fatty acids, whereas the GPI anchor domain is predicted to tether TaLTPG1 to the cell surface.

The encoded primary polypeptide sequence directly C-terminal to the signal peptide through 12 amino acids past the LTP domain (i.e., position 24 through position 120) was used in a Protein Homology/analogY Recognition Engine V 2.0 (Phyre²; Kelley et al. (2015) Nature Protocols 10: 845-858) search of a suitable crystal structure template. This search identified dirt protein with 29% identity at 96.2% confidence (pdb: c2rknA). A 48-residue portion of the Ms1 polypeptide sequence used was modelled with 96.2% confidence to the template c2rknA.

A hydrophobic pocket formed within the LTP domain by disulfide bridges was detected by a combination of the fpocket2 program (Schmidtke et al., (2011) Bioinformatics 27(23):3276-3285) and 3DLigandSite (3DLigandSite: predicting ligand-binding sites using similar structures. (Wass et al. (2010) Nucleic Acids Res. 38:W469-73). Structural models for Ms1, ms1f and ms1h were visualized and annotated using a standard pdb viewer with surface hydrophobicity and rendering calculated using the Colony method. The structures of the LTP domain of ms1d, ms1e, ms1f and ms1h mutants were analyzed using the same techniques as for hydrophobic pocket determination and knowledge of the importance of disulfide bridges in tertiary conformation. (see, e.g., José-Estanyol et al. (2004) *Plant Physiology and Biochemistry* 42:355-365.

The GPI anchor domain and prediction of cell surface tethering was deduced based on BIG-PI Plant Predictor. (Eisenhaber et al. (2003) Plant Physiology 133(4):1691-701)

Example 4

Isolation and Sequences of Wheat Mutant ms1 Alleles

Full-length coding sequences of TaLTPG1 from chromosome 4BS were PCR amplified using a high-fidelity proofreading enzyme from genomic DNAs isolated from male sterile homozygous Ethyl methanesulfonate (EMS)—induced mutants ms1d, ms1e, and ms1f(Klindworth et al. 2002. *Crop Sci.* 42:1447-1450) as well as wild-type (Ms1) male fertile genotypes (cultivar Chris). Both strands of PCR amplicons were sequenced using standard Sanger sequencing techniques for GC-rich products. Comparison of ms1 with Ms1-derived Sanger sequencing chromatograms revealed SNPs between each of the ms1 mutant alleles, including ms1h derived from TILLING, and the wild-type sequence (FIG. 2, FIG. 3). Sequence analysis predicts that protein function is disrupted for each of these mutants.

ms1d exhibits a SNP at position 1856 (G1856A) when compared to wild-type Ms1 genomic DNA sequence (SEQ ID NO:7). This SNP is predicted to abolish the first exon/intron splice junction, resulting in the read-through to a premature stop codon within the first intron and therefore the abolition of a conserved C-terminal GPI-anchoring domain within the encoded polypeptide.

ms1e exhibits a SNP at position 2962 and a 1 bp deletion at position 2963 (G2962A, C2963del) when compared to wild-type Ms1 genomic DNA sequence (SEQ ID NO:7). The 1 bp deletion in ms1e is predicted to cause a frame-shift and the abolition of a conserved C-terminal GPI-anchoring domain within the encoded polypeptide.

ms1f exhibits a SNP at position 1682 (G1682A) when compared to wild-type Ms1 genomic DNA sequence (SEQ ID NO:7). This SNP is predicted to convert a conserved Cysteine to a Tyrosine (C52Y) within the encoded wild-type Ms1 polypeptide (SEQ ID NO:5). This amino acid change is predicted to disrupt the tertiary confirmation of the mature protein mediated by a di-sulfide bridge.

ms1h exhibits a SNP at position 1705 (G1705A) when compared to wild-type Ms1 genomic DNA sequence (SEQ ID NO: 7). This SNP is predicted to convert Aspartic Acid to Asparagine within the encoded wild-type Ms1 polypeptide (SEQ ID NO: 5). This amino acid change is predicted to disrupt the function or activity of the encoded Ms1 polypeptide.

Example 5

Cytological and Metabolite Analysis of Ms1 and ms1 Pollen

Cytological examination of ms1 anthers revealed disrupted tapetal cell surface localized orbicules and collapsed pollen with defective exine structure and ornamentation. Metabolite profiling of fertile versus sterile anthers revealed an accumulation of C16-C22 fatty acids, consistent with a role for Ms1 in sporopollenin biosynthesis and/or transport to the developing microspore.

Cytological Examination

Sterile (ms1d) and fertile (Ms1) mature anthers from late meiosis to bicellular pollen were fixed for either Transmission Electron Microscopy (TEM) or Scanning Electon Microscopy (SEM). TEM samples were infiltrated with 3% glutaraldehyde in phosphate-buffered saline (PBS) pH 7.4, for 16 h at 4° C. whilst SEM samples were infiltrated with paraformaldehyde 4%, glutaraldehyde 1.25%, and sucrose 4% in phosphate-buffered saline (PBS) pH 7.4, for 16 h at 4° C. TEM samples were slow infiltrated with LR White Resin and embedded in gelatin capsules. SEM Samples were rinsed twice with PBS pH 7.4 for 5 min, then dehydrated using a series of graded ethanol solutions (30, 50, 70, 85, 90 and 95%) each for 60 min. SEM samples were then infiltrated 3 times, each for 60 min, in 100% ethanol. Ultra-thin sections of 70 nm were prepared on an ultramicrotome (EM UC6, Leica, Germany), mounted on copper grids and stained with 4% uranyl acetate in water followed by lead citrate according to Bozzola & Russell 1999, (Specimen staining and contrast methods for transmission electron microscopy. Electron microscopy: Principles and techniques for biologists. The Jones and Bartlett Series in Biology, pp. 120-147. Jones and Bartlett Publishers, Boston, Mass.) The ultrathin sections were observed and images captured with TEM (Philips CM100, The University of Adelaide microscopy) at an accelerating voltage of 80 kV. SEM samples were dissected, then critical point dried and sputter coated with platinum (BalTec CPD030 Critical Point Dryer). SEM observation and image capture was performed at an accelerating voltage of 10 kV (Philips XL20 SEM w EDAX EDS, The University of Adelaide microscopy).

Glycosylphosphatidylinositol (GPI) anchored lipid transfer proteins are typically required for cuticular wax accumulation or export onto stem and silique surfaces. (Borner et al. (2003) *Plant Physiology* 132:568-577; Kim et al. (2012) *Plant and Cell Physiology* 53:1391-1403) Epicuticular wax has lipid precursors common to sporopollenin, the major constituent of pollen exine which is produced in the sporophytic tissues of anthers and transported to the developing microspore in structures called orbicules. Analysis of sterile ms1d anthers by both TEM and SEM revealed disrupted tapetal cell surface localized orbicules and collapsed pollen with defective exine structure and ornamentation when compared to fertile Ms1 anthers.

Metabolite Profiling

Anthers were isolated from 2 sterile (ms1d/ms1d) and 1 fertile (Ms1/Ms1) plant at 3 developmental stages (early meiosis to late uninucleate stage) with 3 biological replicates, and snap frozen on dry ice. Using gas chromatography mass spectrometry (GC-MS), the composition and quantity of chloroform-extractable waxes was analyzed. (Jung et al. (2006) Plant Cell 18:3015-3032) Fatty acids were derivatised by extract treatment with the transesterification reagent Meth-Prep II and compared to a sample spiked fatty acid standard.

Analysis of sterile ms1d anthers versus fertile Ms1 anthers across the three developmental stages revealed in excess of a 2-fold increase in palmitic (C16:0), palmitoleic (C16:1), oleic (C18:1n9c), elaidic (C18:1n9t), linoleic (C18:2n6c), gamma-linoleic (C18:3n6), alpha-linoleic (C18:3n6), arachidic (C20:0), paullinic (C20:1), eicosadienoic (C20:2) and behenic (C22:0) acids. The increase in long-chained (C16-C22) fatty acids in mutant anthers is typical of a disruption in sporopollenin biosysnthesis and/or its transport to the developing microspore.

Example 6

Markers in the Ms1 Region and their Use in Identifying and Selecting Wheat Plants Containing Ms1 Mutations The Ms1 gene was found to be tightly linked to markers ET0487, ET0488, ET0489, ET0490, ET0491, ET0495, 007-0033.1, and 007-0046.1 that are located in the Ms1 region. See SEQ ID NO: 24-29, 32 and 33. Because the male sterility trait is controlled by a single nuclear recessive gene, all crosses between male sterile mutants and wild type pollinators will result in 100% male fertile $F_1$ progenies (Ms1ms1), whereas $F_2$ and $BC_1$ progenies will segregate for this trait. It is desirable to determine the genotypes of the progenies, and as such, plants can be evaluated for the presence of the mutation itself, or alternatively, for one or more alleles that are linked to and associated with the mutation in the Ms1 gene (i.e. in linkage disequilibrium with the mutation). For example, one or more alleles at marker ET0487, ET0488, ET0489, ET0490, ET0491, ET0495, 007-0033.1, or 007-0046.1 may be detected to determine if a plant has an ms1 mutation in the homozygous or heterozygous state. For ms1d, ms1e, or ms1f, the mutations arose in the Chris variety; thus, alleles of Chris located in the vicinity of the Ms1 gene are in linkage disequilibrium with the causal mutation and hence can be evaluated for presence or absence in order to determine if ms1d, ms1e, or ms1f is present. Through marker assisted selection, a plant breeder will be able to follow the presence of the male sterility trait through controlled crosses to obtain, when desired, a new plant containing an ms1 mutation in either the homozygous or heterozygous state, thus maintaining the ms1 mutations. A plant breeder can also utilize markers in the Ms1 region to produce mutant male sterile seed parents that would be used as female, i.e. plants that need pollination by a pollen donor plant, to produce seeds of commercial interest or to produce $F_1$ hybrids that contain an ms1 mutation in the heterozygous state.

Example 7

Wheat Transformation

Wheat transformation protocols are available to one of skill in the art. See, for example, He, et al., (2010) J. Exp. Botany 61(6):1567-1581; Wu, et al., (2008) Transgenic Res. 17:425-436; Nehra, et al., (1994) Plant J. 5(2):285-297; Rasco-Gaunt, et al., (2001) J. Exp. Botany 52(357):865-874; Razzaq, et al., (2011) African J. Biotech. 10(5):740-750; Tamás-Nyitrai, et al., (2012) Plant Cell Culture Protocols, Methods in Molecular Biology 877:357-384; and U.S. patent publication 2014/0173781.

Example 8

Restoring Male Fertility to Wheat ms1 Homozygous Recessive Plants by Expressing a Transformed Copy of an Ms1 Gene or Ortholog In a previous example, nucleotide sequence differences were detected within regions of DNA that correspond to the Ms1 candidate gene from ms1d, ms1e and ms1f plants. In this example, various strategies are described for restoring male fertility to homozygous recessive ms1d plants. Male-sterile wheat plants containing an ms1 mutation are restored to male fertility when transformed with a DNA vector containing a functional copy of an Ms1 gene. This demonstrates that the candidate Ms1 gene is effective in complementing ms1 mutations which cause the male-sterile phenotype.

Although wheat is an allohexaploid containing three related genomes (ABD) with similar gene content, it behaves as a diploid during meiosis. Often the related wheat genomes contain homeologous genes that have similar gene structure and function, requiring triple mutants to result in a loss-of-function phenotype. However, the wheat male sterility phenotype observed in the ms1d mutant segregates at a 3:1 ratio of fertile to sterile plants. This indicates that in this mutant, a single recessive locus in the homozygous condition induces a male sterility phenotype and that this locus segregates according to the laws of Mendelian inheritance. The lack of functional redundancy with the other homeologues for Ms1 indicates that there has been divergence in the function of the A and D genome copies of this gene.

Marker development and assessment has shown that a heterozygous ms1 locus segregates at a 1:2:1 ratio of homozygous wild type to heterozygous to homozygous mutant. The correlation of phenotypic and genotypic data supports the Mendelian inheritance of the ms1 mutation.

The Mendelian nature of the ms1 mutation will facilitate introgression of a male sterility trait into different genetic backgrounds.

One strategy to restore male fertility to ms1 plants is to express a gene or genes that can overcome the loss of function or activity resulting from Ms1 mutation or deletion. A gene from wheat, or from another plant species, having identical or similar function to Ms1 is used to restore gene activity in transformed wheat plants. For example, as shown in FIG. 1, a gene from barley encodes a protein with high amino acid sequence similarity to the wheat Ms1 gene product, with approximately 79% sequence identity. The barley gene present within SEQ ID NO: 1 is introduced into wheat ms1 mutant plants to restore male fertility. This barley gene may be expressed using its native promoter (see SEQ ID NO: 1, nucleotides 1-902, SEQ ID NO:41) or a non-native promoter, such as a tissue-preferred, constitutive or conditional promoter, to restore male fertility. Other monocot or dicot plants, can also serve as sources of a complementing gene and promoter to restore male fertility to ms1 mutant male-sterile wheat plants. The gene and promoter may be from one source or from a combination of source species, for example, from one or more of wheat, barley, rice, and Brachypodium.

In another strategy, the wild-type wheat Ms1 gene or a variant (see, for example, SEQ ID NO: 1, 2, 4, 7, 9, 42, 43, 44, or 45) is used to restore male fertility to homozygous recessive ms1 plants. The variant Ms1 gene comprises alteration of one or more DNA restriction sites to allow compatibility with DNA vectors used for plant transformation. See, for example, SEQ ID NO: 9, which comprises nucleotide changes introduced at positions 2, 3, 1209, and 1301, to facilitate vector construction. The Ms1 gene is introduced into ms1 plants by known plant transformation methods to produce plants containing stably integrated versions of the Ms1 gene for fertility complementation. As an alternative to using the native Ms1 promoter (SEQ ID NO: 6), a promoter variant (for example see SEQ ID NO: 8, which comprises nucleotide changes introduced to facilitate vector construction), or other plant, such as SEQ ID NO:41, or non-plant constitutive, conditional or tissue-preferred promoter is used to express a wild-type or variant version of the Ms1 gene or cDNA for the purpose of restoring male fertility to homozygous recessive ms1 wheat plants. The gene and promoter may be from one source species or from a combination of source species. In some examples, the promoter is a Ms1 promoter from wheat, rice, barley or brachypodium. The genomic Ms1 sequence 3' to the translational stop codon comprises a functional terminator region; see SEQ ID NO: 7 UTR at positions 3384-4335 (SEQ ID NO:46). See also SEQ ID NO: 1 UTR at positions 2838-3838 (SEQ ID NO:47).

Constructs and Transformation

To restore the fertility of ms1d/ms1d homozygous mutants, the wheat Ms1 gene under control of the native wheat Ms1 promoter and terminator was linked to a DsRed2 gene under control of the barley LTP2 promoter (see, e.g., U.S. Pat. No. 5,525,716) and also carrying a PINII terminator sequence (TaMs1-DsRED). This construct was transformed directly into wheat embryos harvested from Ms1/ms1d heterozygote plants through *Agrobacterium*-mediated transformation methods as referenced elsewhere herein. Several independent T-DNA insertion events containing TaMs1-DsRED were obtained for construct evaluation in ms1d plants.

T0 Plant Generation and Analysis

T0 wheat plants containing a single-copy TaMs1-DsRED cassette were identified and genotyped as homozygous or heterozygous for ms1d mutation. Selfed seed from these individual plants was counted as a qualitative measure of male fertility. As shown in Table 4, no seed set was observed in ms1d/ms1d homozygous plants lacking the TaMs1-DsRED cassette. In contrast, seed set was observed when ms1d/ms1d homozygous plants contained a transformed copy of the TaMs1-DsRED cassette. These results demonstrate that the transformed copy of TaMs1 was functional and able to restore fertility to ms1d/ms1d homozygous male sterile plants.

TABLE 3

Seed set in T0 wheat plants containing a TaMs1 complementation T-DNA insertion.

| T-DNA Insertion Event | ms1d Genotype | T-DNA Copy Number | Male Fertility Phenotype |
| --- | --- | --- | --- |
| Event-1 | ms1d/ms1d | 1 | Fertile |
| Event-2 | ms1d/ms1d | 1 | Fertile |
| Event-3 | ms1d/ms1d | 2 | Fertile |
| Event-4 | ms1d/ms1d | 2 | Fertile |
| Event-5 | ms1d/ms1d | 3 | Fertile |
| Event-6 | ms1d/ms1d | 4 | Fertile |
| Event-7 | Ms1/ms1d | 1 | Fertile |
| Event-8 | Ms1/ms1d | 1 | Fertile |
| Event-9 | Ms1/ms1d | 1 | Fertile |
| Event-10 | Ms1/ms1d | 1 | Fertile |
| Event-11 | Ms1/ms1d | 1 | Fertile |
| No T-DNA | ms1d/ms1d | 0 | Sterile |
| No T-DNA | ms1d/ms1d | 0 | Sterile |

T1 Plant Analysis; Molecular and Phenotypic

Inheritance of complementation by TaMs1 T-DNA insertion was shown by analyzing the T1 plants derived from two separate T0 plants with independent T-DNA insertions (Event-1 and Event-7). One set of T1 progeny was derived from a T0 plant homozygous for ms1d mutation (ms1d/ms1d) with TaMs1-DsRED cassette (Event-1). The second set of T1 progeny was derived from a T0 plant heterozygous for ms1d mutation (Ms1/ms1d) with TaMs1-DsRED cassette (Event-7). Plants from both sets were genotyped for ms1d and the T-DNA insertion. In both sets of T1 progeny, all the plants with genotype ms1d/ms1 and T-DNA insertion (Event-1 or Event-7) were fertile as determined by production of seed (Table 5). All the progeny with genotype ms1d/ms1d without the T-DNA insertion were male sterile and did not produce seed. This clearly demonstrated that the TaMs1 complementation T-DNA insertion is able to restore fertility to the ms1d/ms1d mutant plants and this ability is passed on to the progeny.

TABLE 4

Fertility of T1 plants with or without a TaMs1 complementation T-DNA insertion.

| T0 Event | T1 Plant | ms1d genotype | T-DNA Copy Number | Male Fertility Phenotype |
| --- | --- | --- | --- | --- |
| Event-1 | Plant 1 | homozygous | 1 | Fertile |
| Event-1 | Plant 2 | homozygous | 1 | Fertile |
| Event-1 | Plant 3 | homozygous | 1 | Fertile |
| Event-1 | Plant 4 | homozygous | 1 | Fertile |
| Event-1 | Plant 5 | homozygous | 2 | Fertile |
| Event-1 | Plant 6 | homozygous | 2 | Fertile |
| Event-1 | Plant 7 | homozygous | 2 | Fertile |
| Event-1 | Plant 8 | homozygous | 0 | Sterile |
| Event-1 | Plant 9 | homozygous | 0 | Sterile |
| Event-7 | Plant 1 | homozygous | 1 | Fertile |
| Event-7 | Plant 2 | homozygous | 1 | Fertile |
| Event-7 | Plant 3 | homozygous | 1 | Fertile |
| Event-7 | Plant 4 | homozygous | 2 | Fertile |
| Event-7 | Plant 5 | homozygous | 2 | Fertile |
| Event-7 | Plant 6 | homozygous | 2 | Fertile |
| Event-7 | Plant 7 | homozygous | 0 | Sterile |
| Event-7 | Plant 8 | homozygous | 0 | Sterile |

In conclusion, analysis of the T0 and T1 plants with the T-DNA insertion containing the native wheat MS1 gene showed that this gene is able to restore fertility to the ms1d/ms1d homozygous recessive mutation. This example is a further proof that the ms1d mutation is in the wheat Ms1 gene.

Example 9

Inbred Maintenance and Increase of Wheat ms1 Male-Sterile Plants Using A Hemizygous Maintainer This example demonstrates that wheat plants homozygous recessive for ms1 can be maintained as male-sterile plants using a functional copy of Ms1 linked to a seed marker gene and pollen inhibition gene.

It would be advantageous to produce a pure line of male-sterile plants to allow for cross pollination with a different inbred wheat variety to produce hybrid seed. Generally, strategies that incorporate recessive male sterility result in plants that cannot self-pollinate. To accomplish self-pollination and the production of a pure line of male-sterile plants for cross pollination, an expression cassette (Ms1-AA-Red) is constructed which comprises a functional copy of Ms1 linked to the maize PG47 promoter expressing a functional alpha amylase gene (see, for example, SEQ ID NO: 30) and further linked to a color-marker gene (for example, encoding a red fluorescent protein) under control of the barley LTP2 promoter (see, e.g., U.S. Pat. No. 5,525,716) and also carrying a PINII terminator sequence. Using biolistic or Agrobacterium-mediated transformation, this construct is transformed directly into embryos derived from self-pollinated Ms1/ms1 wheat plants. Transformed embryos are regenerated into plants. Wheat plants (ms1/ms1) containing single-copy Ms1-AA-Red cassette, which can be identified using markers flanking the ms1 locus as described above, are male-fertile and are allowed to self-pollinate. Due to the action of PG47:AA to inhibit pollen function and thus prevent transmission of the Ms1-AA-Red expression cassette through pollen, seed from this generation of progeny will segregate at a frequency of 1:1 red-fluorescence and non-fluorescence. Progeny grown from red-fluorescing seed are hemizygous for Ms1-AA-Red, homozygous for ms1, and male fertile; these are used to propagate (i.e., "maintain") the male-sterile inbred. Progeny of the non-fluorescing seed do not contain a transformed copy of the Ms1 complementing gene, are homozygous for ms1 and male-sterile. These male-sterile inbreds are used as the female inbred for the production of hybrid seed when planted adjacent to male inbred wheat plants that are wild-type for the Ms1 gene.

Example 10

Targeted Regulation or Mutagenesis of Gene

For male fertility applications, it may be advantageous to mutate the endogenous Ms1 gene or change its expression, such as by methods described in this example.

Introducing an RNA into a living cell has been shown to inhibit expression of a target gene in that cell. (Bae et al. (2010) Plant Breeding 129 (6):647-651; Beetham et al. (1999) Proceedings of the National Academy of Sciences 96 (15):8774-8778, doi:10.1073/pnas.96.15.8774; Cigan et al. (2010) U.S. Pat. No. 7,696,405; Cigan et al. (2005) The Plant Journal 43 (6):929-940; Dalakouras et al. (2009) The Plant Journal 60 (5):840-851, doi:10.1111/j.1365-313X.2009.04003.x; Fire et al. (1998) Nature 391 (6669): 806-811; Fire et al. (1999) WO 1999032619 A1; Mette et al. (2000) EMBO J 19 (19):5194-5201; Okuzaki and Toriyama (2004) Plant Cell Reports 22 (7):509-512. doi:10.1007/s00299-003-0698-2; Tang (2013) WO 2013025670 A1; Timmons and Fire (1998) Nature 395:854; Yu et al. (2002) PNAS 99 (9):6047-6052. A skilled artisan will appreciate that the RNA could be expressed within the cell or applied exogenously (Tang WO 2013025670 A1)).

Interfering RNA may target transcription, translation or mRNA stability, thereby changing the expression of the targeted gene. In this example, expression of the Ms1 gene is reduced or silenced by expressing in planta either RNAs that target the promoter region, as has been shown previously in monocots (Cigan et al. 2010) including wheat (U.S. patent application Ser. No. 14/203,698), or RNAs that target the expressed mRNA, either individually or in combination. For the promoter inverted repeat approach, a portion of the Ms1 promoter region may be duplicated, juxtaposed and oriented in tandem in opposite directions and placed under the control of a constitutive, tissue-preferred or conditional promoter in a plant transformation vector, for the purpose of expressing the promoter inverted repeat RNA in plant cells to silence a gene operably linked to the target promoter.

The skilled artisan will further appreciate that changes can be introduced by mutation of the nucleic acid sequences, thereby leading to changes in either the expression of encoded mRNAs or the amino acid sequence of the encoded Ms1 polypeptide, resulting in alteration of the biological activity of the mRNA or protein, respectively, or both. See for example methods described in U.S. patent application Ser. No. 14/463,687 filed on Aug. 20, 2014, incorporated by reference in its entirety herein. Thus, variant nucleic acid molecules can be created by introducing one or more nucleotide substitutions, additions and/or deletions into the corresponding nucleic acid sequence or surrounding sequences disclosed herein. Such variant nucleic acid sequences are also encompassed by the present disclosure.

Variant nucleic acid sequences can be made by introducing sequence changes randomly along all or part of the Ms1 genic region, including, but not limited to, chemical or irradiation mutagenesis and oligonucleotide-mediated mutagenesis (OMM) (Beetham et al. 1999; Okuzaki and Toriyama 2004). Alternatively or additionally, sequence changes can be introduced at specific selected sites using double-strand-break technologies such as but not limited to ZNFs, custom designed homing endonucleases, TALENs, CRISPR/CAS (also referred to as guide RNA/Cas endonuclease systems (U.S. patent application Ser. No. 14/463,687 filed on Aug. 20, 2014)), or other protein-, or polynucleotide-, or coupled polynucleotide-protein-based mutagenesis technologies. The resultant variants can be screened for altered Ms1 activity. It will be appreciated that the techniques are often not mutually exclusive. Indeed, the various methods can be used singly or in combination, in parallel or in series, to create or access diverse sequence variants.

Example 11

Inducing Male-Sterility by Post-Transcriptional Gene Silencing of TaLTPG1

A polynucleotide fragment (SEQ ID NO: 38) was isolated from the 3'UTR of TaLTPG1 and sub-cloned within an RNAi cassette (ZmUbi::TaLTPG1-IR:SbActin term) into constitutive expression vector PHP1.

Plants for transformation donor material were sown at 5-6 plants per 6 L (8 inches diameter) pot containing soil mix. The soil mix consisted of 75% (v/v) Coco Peat, 25% (v/v) nursery cutting sand (sharp), 750 mg/L CaSO4.2H2O (gypsum) 750 mg/L Ca(H2PO4)2.H20 (superphosphate), 1.9 g/L FeSO4, 125 mg/L FeEDTA, 1.9 g/L Ca(NO3)2, 750 mg/L Scotts Micromax micronutrients, and 2.5 g/L Osmocote Plus slow release fertilizer (16:3:9) (Scotts Australia Pty. Ltd.). The pH was adjusted to between 6.0 and 6.5 using 2 parts agricultural lime to 1 part hydrated lime. Potted plants were grown in controlled environment growth rooms at 23° C. (day) and 16° C. (night) with a photoperiod extended using 400 W high pressure sodium lamps in combination with metal halide lamps to 12 hour over winter months.

Co-bombardment of the RNAi cassette with the constitutively expressed hpt selectable marker gene sequence was conducted according to published methods. Ismagul et al. in Crop Breeding Vol. 1145 Methods in Molecular Biology (eds D. Fleury & R. Whitford) Ch 14, 239-252 (Springer, 2014). T0 regenerants were recovered by selection on MS medium containing 100 mg/L of Hygromycin B.

Pollen grain viability tests were performed on mature anthers collected from different spikelets of individual plants immediately before dehiscence. Anthers were placed on moistened filter paper in petri dishes for transport to the laboratory, where they were crushed on a clean slide in a drop of 2% potassium iodide solution. Pollen grains lying between the slide and coverslip were protected from drying by surrounding the edge of the coverslip with clear nail varnish. Samples were examined and documented using an Axio Imager M2 microscope coupled to and AxioCam MRm3 S/N 5669 camera.

Individual plants were assessed for self-fertility by placing a glassine bag over each head before anthesis. Between 3 and 10 heads per plant were collected for seed counting. The two basal and two apical spikelets per head were eliminated from analysis due to their incomplete development. Total seed set and numbers of florets were counted on a per head basis. The percentage of fertility for each spike or plant was calculated as follows:

$$\% = \frac{\text{Total number of seed set per spike or plant}}{\text{Total number of florets per spike or plant}} \times 100$$

DNA extractions from all transgenic regenerants were performed using either a phenol chloroform or freeze-dried extraction protocol. (Kovalchuk, N. in *Crop Breeding* Vol. 1145 *Methods in Molecular Biology* (eds D. Fleury & R. Whitford) 239-252 (Springer, 2014). A 15 cm leaf piece from a 2 week old plant was frozen in liquid nitrogen, and the tissue was ground to a fine powder using 1 large (9 mm) and 3 small (3 mm) ball bearings and a vortex. 700 μL of extraction buffer (1% sarkosyl, 100 mM Tris-HCl pH 8.5, 100 mM NaCl, 10 mM EDTA, 2% PVPP) was added to each sample and the samples were mixed for 20 min on a rotary shaker. 700 μL of phenol/chloroform/iso-amylalcohol (25:24:1) was added and the extract was transferred to a silica matrix tube and spun at 4000 rpm for 10 min. DNA was precipitated by adding 60 μL 3M sodium acetate pH4.8 and 600 μL isopropanol and centrifuged at 13 000 rpm for 10 min. The DNA pellet was washed with 1 mL 70% ethanol, centrifuged for 2 min at 13 000 rpm and air dried for 20 min. The purified DNA was resuspended in 50 μL of R40 (1× TE, 40 μg/ml RNase A). The presence of the RNAi cassette in T0 regenerant plantlets was assessed by PCR with transgene specific primers.

Ninety-nine T0 regenerant plantlets were identified to be resistant to Hygromycin, of which 73 were deemed to contain the RNAi cassette. Of the 73 PCR positive T0 transgenics, 26 (approximately 36%) were observed to be either completely sterile or express partial sterility when assessed for self-fertility. These findings indicate that TaLTPG1-specific post-transcriptional gene silencing can induce sterility.

Example 12

Restoration of Fertility to ms1d Homozygotes Using Genomic TaLTPG1

A genomic fragment of TaLTPG1 in vector PHP2 was introduced into the genotype ms1d×Gladius (F2/F3 generation) via biolistic transformation.

Transformation was performed as per Example 11. Regenerant T0 plantlets were genotyped by KASPar analysis using Ms1 linked markers ET0292 (SEQ ID NO: 34), ET0294 (SEQ ID NO: 35), 007-0042.1 (SEQ ID NO: 36), 007-0046.1 (SEQ ID NO: 33) as well as 007-0182.1 (SEQ ID NO: 37) targeting Ms1 4BS variant promoter (artificial) from SEQ ID NO: 8. Plants identified to be ms1d homozygotes and containing the Ms1 4BS variant promoter were assessed for self-fertility as per the methodology of Example 11.

Eighty T0 regenerant plantlets were identified to be resistant to Hygromycin, of which 69 were deemed to contain the transgene-derived Ms1 4BS variant promoter by KASP analysis with 007-0182.1. Of these 69 T0 transgenics, 4 were identified by KASP analysis using 007-0009.1, 007-0011.1, 007-0042.1, and 007-0046.1 markers to be homozygous for the Chris haplotype (ms1d/ms1d). Spikes bagged pre-anthesis revealed three lines to be self-fertile. These findings indicate that a genomic fragment of TaLTPG1 can restore fertility to ms1d homozygotes.

Example 13

Ms1 Promoter-Inverted-Repeat Expression Affects Fertility in Wheat

This example demonstrates that the fertility of plants can be altered by expression of Ms1-promoter-specific inverted repeat (promoter-inverted-repeat, pIR) molecules. This provides further evidence that expression of the Ms1 gene is required for male fertility in wheat.

A pIR construct was generated by linking a ubiquitin promoter to inverted repeats which targeted a portion of the wheat Ms1 promoter (SEQ ID NO: 6), including a NOS spacer segment between the inverted repeat sequences. Nucleic acid molecules and methods for preparing the vector were as previously described (Cigan et al Plant Journal (2005) 43, 929-940). This construct was introduced into wheat Fielder variety by *Agrobacterium*-mediated transformation using methods known in the art and referenced elsewhere herein.

Plants were grown in the greenhouse. Transgene copynumber was determined by quantitative polymerase chain reaction (QPCR). Plants were grown to maturity and male fertility phenotype was recorded.

Suppression was sufficient to cause male-sterility in 100% of events. Both single-copy and multi-copy T-DNA insertion events were male-sterile, indicating that both single-copy and multi-copy insertion events are effective. This example further demonstrates that Ms1 gene is a male fertility gene in wheat and its suppression results in male sterility.

That which is claimed:

1. A method of restoring fertility to a male-sterile wheat plant, the method comprising:
   introducing into a wheat plant that is homozygous recessive for a disruption of endogenous MS1 polynucleotide, wherein the disruption results in male-sterility, wherein the endogenous MS1 polynucleotide is selected from the group consisting of:
   a. a polynucleotide that encodes the polypeptide of SEQ ID NO:5;
   b. a polynucleotide comprising the sequence set forth in SEQ ID NO:4, 7, or 9; and
   c. a polynucleotide having at least 90% sequence identity to SEQ ID NO: 4, 7, or 9;
   a polynucleotide that encodes a polypeptide having at least 90% sequence identity to SEQ ID NO: 3, 5, 39 or 40, wherein the expression of the polypeptide restores male fertility to the male-sterile wheat plant, wherein the polynucleotide that encodes the male fertility restoration polypeptide is operably linked to a polynucleotide of interest encoding a reporter or marker product.

2. The method of claim 1, wherein the polypeptide that restores the wheat plant's male fertility is from wheat or barley.

3. The method of claim 1, wherein the polynucleotide that encodes the polypeptide that restores male fertility to the male-sterile wheat plant is driven by a heterologous promoter active in a plant cell.

4. The method of claim 1, wherein the polynucleotide that encodes the polypeptide that restores male fertility to the male-sterile wheat plant is driven by a MS1 promoter.

5. The method of claim 4, wherein the MS1 promoter is from wheat or barley.

6. The method of claim 4, wherein the MS1 promoter is the nucleic acid sequence of SEQ ID NO: 6, SEQ ID NO:41, or the nucleotide sequence from 1-902 of SEQ ID NO:1.

7. The method of claim 1, wherein the polynucleotide that encodes the polypeptide that restores male fertility to the male-sterile wheat plant is driven by a male tissue-preferred promoter.

8. The method of claim 1, wherein the polynucleotide of interest encodes a reporter that confers antibiotic resistance or herbicide resistance.

9. The method of claim 1, wherein the polynucleotide of interest encodes a color marker.

10. The method of claim 1, wherein the polynucleotide of interest is expressed in seed.

\* \* \* \* \*

SEQUENCE LISTING

<160> NUMBER OF SEQ ID NOS: 47

<210> SEQ ID NO 1
<211> LENGTH: 3838
<212> TYPE: DNA
<213> ORGANISM: Hordeum vulgare
<220> FEATURE:
<221> NAME/KEY: promoter
<222> LOCATION: (1)..(902)

<400> SEQUENCE: 1

| | | | | | |
|---|---|---|---|---|---|
| cgcacatcaa | cataaactca | tcagatggga | ataatcggat | ctacgaagga | cataaaactc | 60 |
| tttaatctca | tgacaacgcc | agaagagcaa | gagtaaatat | attctcataa | aaaacaatga | 120 |
| acactagatg | atgacgaaga | acataagatt | cttcaaggag | aaattgcggc | agcggagatg | 180 |
| gcagccggag | gcgaggggc | caaaaactct | gttgcggcgg | cagcggtagc | cttggtgaaa | 240 |
| cccacacgtt | tgcacaccat | ataagttgtt | tgcaagggtt | acatgggcct | cgctctcgtg | 300 |
| aaaaagaagg | tcatacatgg | gtcttggtct | cgtgcaaaac | gaaaggtcag | cagtccatgg | 360 |
| gccggaggaa | aaaccgggca | acaacacgcc | atgtgtgttt | tcgcgggaac | ccaattccga | 420 |
| aatcactcac | cggcacctcg | tcccgatgcc | ttccagaacg | ttctacgtgc | ttccacaggg | 480 |
| ccagcccagc | cgtgggatca | gatcaggatc | agcacgaaca | ttgaagctag | cgcggcgata | 540 |
| tttttcccag | cctccgcctc | gctcgacgac | tgcatttcat | ttcgaaaaca | aaaaaagag | 600 |
| ctttctcctt | ctcatcccga | gcgccagagg | agcaccagaa | aggccaccca | cccaccctca | 660 |
| cgtaccgccc | tcgcacccgc | gcggccacat | ctgggccgtc | cacttgggca | gctggccgtt | 720 |
| ccattcccga | actgacgggc | aggatcgagc | gagcggcgcg | cccacggctc | ctccggctat | 780 |
| ataacccgcc | acccacacca | ctcccctccg | gcgttccacc | agagccttcc | tccctccacc | 840 |
| gcaccaccac | caccaccgcg | ccaaaaaccc | tagggagcga | gcgagctcac | ctcgccccgc | 900 |
| ccatggagag | atcccgccgc | ctgctgctcg | tggcggggct | cctcgccgcg | ctgctcccgg | 960 |
| cggcggccgc | caccttcggg | ctgcagcagg | gggcgcagtg | cgaccccacg | ttcctggcga | 1020 |
| cgcaggccgc | gctcttctgc | gccccgaca | tgcccacggc | ccagtgctgc | gagcccgtcg | 1080 |
| tcgccgcctt | cgacctcggg | ggcggcgtcc | cctgcctctg | ccgcgtcgcc | gccgagccgc | 1140 |
| agctggtcat | ggcggggctc | aacgccaccc | acctcttcgc | gctgtacacc | tcctgcggcg | 1200 |
| gcatccgtcc | cggtggcgcc | cacctcgccg | ccgcctgcca | aggtacgttc | acgttcaccg | 1260 |
| cctccctccc | tctccttctc | tctttgcacc | tgtaccagcc | gattcggcgt | tcgctttcgc | 1320 |
| gtttcccggt | agttttgatg | gtttctcgag | tcgccagtgc | tccgatttgg | gttcggtttc | 1380 |
| cttgcgttgt | accggatctg | cctgtacggc | gcgcggcgtc | ggggttctcg | ttgtttcccg | 1440 |
| tggcgagcat | ccccgcgcgc | ccacggccta | gctagcttac | cttcagatac | gcggagcgat | 1500 |
| ttaggatcag | tatgaggagt | tcgtcgtaga | agaatgcatg | cggaacgcgc | gattgtttgt | 1560 |
| ttcatcgatt | ttggatctgt | gataggcctg | cttgttcccg | agttttttgca | cgtagaagaa | 1620 |
| tcatgtgcag | aaccctggt | ccattatttg | ttatgtatat | acacgattac | ttgtgcatat | 1680 |
| gcagaagtct | tagttatctg | ctaccttcc | agaattattc | gtggtgtttt | tgttcctcta | 1740 |
| gttaaacttc | agatgatctt | tcgttcgagt | ttattttcct | gcctgtaact | gagatcgata | 1800 |
| tacctatcac | cgtgactgtg | agagagacag | agagttgttg | ccgtttaact | gctatatata | 1860 |
| tgtacgtttt | ctgctactgt | ttaatcgact | gctccatccc | gttcgcgata | ggacttgttt | 1920 |
| caaaccgtca | cgcagctctg | cttcctgcag | tgtctttgt | cttcgtttgg | tcaaaactga | 1980 |

-continued

| | |
|---|---|
| aaacgcttgc tatcgaggcc agaggcaggg caaaagctcc ccgtactttt cgctttgcag | 2040 |
| tggcatctct ttctttttt ttgccgaaaa ttgtttccac gttcatcccc gggtgtcgta | 2100 |
| ctacttaatt atctgcatgc agttttcgtg tccttcctcc gtcgtgaaaa aaaggttggg | 2160 |
| tcaaatgaat caaccgtgta tgcagggcag cagcaacaga gatagagtag ctggctgtcg | 2220 |
| cagctttaac aaaagcagtc tgtggcctgc cacagttttc ctgattttg tttaatctgg | 2280 |
| cctgggcttc ttttcttgtt gcgcacgtcg tcgcctcctt ctttttcc aattttttga | 2340 |
| tttcttttga gataaggaca cgaacggctg gtaactgact tttcttgttg ttttttactg | 2400 |
| tgggttttgg acgcaggacc ggctcccccg gccgccgtcg tcagcagccc ccgccacca | 2460 |
| tcgccagcac ctcgccgcaa acaggcagcg cgtacgaacc tctcgctctc tctctctccc | 2520 |
| tctcgcctgc atctcgctct gtacataacc tattgggttc atatgctgat cagcgttgac | 2580 |
| atactaactt gttcatttga ttctcagacg acgcgcctcc accgccgccg tccagcgaga | 2640 |
| agccatcccc gccgcccag gagcatgacg gcgccgcaca cgccaagagc gcccccgccc | 2700 |
| tcgcggctcc taccccgctc gcgcccgctg ccgctactgc cccgccgccc gaggcgccac | 2760 |
| actccgccgc gtcgtcgtcc gattcggcct tcatcttcat cgccgcggcc atgctcgcca | 2820 |
| tttacatcgt cctctgaatg gccgacccc aaggcagcag agtacttgtc atctgattcc | 2880 |
| gtttcatgct tgtcgccgtt tgttgaggtt cgtttctgca gtccgaacaa gacggtgggg | 2940 |
| ttttgatcgg gtacccagat ttctatgtcg atcgcgcgta ctagtactag tagttgctta | 3000 |
| gcagatgaac gaacattggg ttttgggatt cctctagctg atgaaccact gctatttcc | 3060 |
| atgtgatcga tggatatgat ctgaatggat ggatgaagtt ttggtttctg atgctgatga | 3120 |
| tgtgctgctt cttcatttgc atgctcgatc tattccttca attttgtgga gcaacagttt | 3180 |
| gtttagcttc tgttctgcta tgaataatgc cgcttgcatc ttgtcattgc tgataatctg | 3240 |
| cttaatgcag acattgcttc cgtcccaaac aatctgttgc ttaccaggta atgcatataa | 3300 |
| tctgtacctc accttcgcac aacaacagaa gctaccctgc taaaaaaaca cacacacaca | 3360 |
| cacaaaaaaa acagaagctg gtctcacacg gaagccgctt cggggactgt tgcagctttt | 3420 |
| ttattgccat tttgttttc atgcaggtac aaatcgaggg tgttgcttga tttgatcatg | 3480 |
| gatgatcact tagagcaaca tgtgtgtttt gtctgtgttt tattcgttgc tcgtccatcc | 3540 |
| aatttaaact tgaaatggat cgtgtgtgga taaaagaaga cgtgcgtcag tttgaatcga | 3600 |
| cgcgttgggt tatattttgt gtctgtgacg accgaaacga agacaaaata tatcgtccgg | 3660 |
| ttagaattgc tctaatgcta gctttctctc ctaccatcgc attccgtggt aggaaaaagt | 3720 |
| actagaacca caggaaactg gaacgcaaga aaagcatatc taccgttggc cgttgatctt | 3780 |
| gtttcacatt cggtatggct ccggtcatat tgttggagat tcacattcat gcacgcaa | 3838 |

<210> SEQ ID NO 2
<211> LENGTH: 642
<212> TYPE: DNA
<213> ORGANISM: Hordeum vulgare

<400> SEQUENCE: 2

| | |
|---|---|
| atggagagat cccgccgcct gctgctcgtg gcggggctcc tcgccgcgct gctcccggcg | 60 |
| gcggccgcca ccttcgggct gcagcagggg gcgcagtgcg accccacgtt cctggcgacg | 120 |
| caggccgcgc tcttctgcgc ccccgacatg cccacggccc agtgctgcga gcccgtcgtc | 180 |
| gccgccttcg acctcggggg cggcgtcccc tgcctctgcc gcgtcgccgc cgagccgcag | 240 |
| ctggtcatgg cggggctcaa cgccacccac ctcttcgcgc tgtacacctc ctgcggcggc | 300 |

```
atccgtcccg gtggcgccca cctcgccgcc gcctgccaag gaccggctcc cccggccgcc    360
gtcgtcagca gcccccgcc accatcgcca gcacctcgcc gcaaacaggc agcgcacgac     420
gcgcctccac cgccgccgtc cagcgagaag ccatccccgc cgccccagga gcatgacggc    480
gccgcacacg ccaagagcgc ccccgccctc gcggctccta ccccgctcgc gcccgctgcc    540
gctactgccc cgccgcccga ggcgccacac tccgccgcgt cgtcgtccga ttcggccttc    600
atcttcatcg ccgcggccat gctcgccatt tacatcgtcc tc                      642
```

<210> SEQ ID NO 3
<211> LENGTH: 214
<212> TYPE: PRT
<213> ORGANISM: Hordeum vulgare

<400> SEQUENCE: 3

```
Met Glu Arg Ser Arg Arg Leu Leu Leu Val Ala Gly Leu Leu Ala Ala
1               5                   10                  15

Leu Leu Pro Ala Ala Ala Ala Thr Phe Gly Leu Gln Gln Gly Ala Gln
            20                  25                  30

Cys Asp Pro Thr Phe Leu Ala Thr Gln Ala Ala Leu Phe Cys Ala Pro
        35                  40                  45

Asp Met Pro Thr Ala Gln Cys Cys Glu Pro Val Val Ala Ala Phe Asp
    50                  55                  60

Leu Gly Gly Gly Val Pro Cys Leu Cys Arg Val Ala Ala Glu Pro Gln
65                  70                  75                  80

Leu Val Met Ala Gly Leu Asn Ala Thr His Leu Phe Ala Leu Tyr Thr
                85                  90                  95

Ser Cys Gly Gly Ile Arg Pro Gly Ala His Leu Ala Ala Ala Cys
            100                 105                 110

Gln Gly Pro Ala Pro Ala Ala Val Val Ser Ser Pro Pro Pro
        115                 120                 125

Ser Pro Ala Pro Arg Arg Lys Gln Ala Ala His Asp Ala Pro Pro
    130                 135                 140

Pro Pro Ser Ser Glu Lys Pro Ser Pro Pro Gln Glu His Asp Gly
145                 150                 155                 160

Ala Ala His Ala Lys Ser Ala Pro Ala Leu Ala Ala Pro Thr Pro Leu
                165                 170                 175

Ala Pro Ala Ala Ala Thr Ala Pro Pro Glu Ala Pro His Ser Ala
            180                 185                 190

Ala Ser Ser Asp Ser Ala Phe Ile Phe Ile Ala Ala Ala Met Leu
        195                 200                 205

Ala Ile Tyr Ile Val Leu
    210
```

<210> SEQ ID NO 4
<211> LENGTH: 660
<212> TYPE: DNA
<213> ORGANISM: Triticum aestivum

<400> SEQUENCE: 4

```
atggagagat cccgcgggct gctgctggtg gcggggctgc tggcggcgct gctgccggcg    60
gcggcggcgc agccgggggc gccgtgcgag cccgcgctgc tggcgacgca ggtggcgctc    120
ttctgcgcgc ccgacatgcc gacggcccag tgctgcgagc ccgtcgtcgc cgccgtcgac    180
ctcggcggcg gggtgcccctg cctctgccgc gtcgccgccg agccgcagct cgtcatggcg    240
```

-continued

```
ggcctcaacg ccacccacct cctcacgctc tacagctcct gcggcggcct ccgccccggc       300 ggcgccacc tcgccgccgc ctgcgaagga cccgctcccc cggccgccgt cgtcagcagc        360 ccccgcccc cgcctccacc gtccgccgca cctcgccgca agcagccagc gcacgacgca        420
ccaccgccgc caccgccgtc gagcgagaag ccgtcgtccc cgccgccgtc ccaggaccac       480
gacggcgccg cccccgcgc caaggccgcg cccgcccagg cggccacctc cacgctcgcg        540
cccgccgccg ccgccaccgc cccgccgccc caggcgccgc actccgccgc gcccacggcg       600
ccgtccaagg cggccttctt cttcgtcgcc acggccatgc tcggcctcta catcatcctc       660
```

<210> SEQ ID NO 5
<211> LENGTH: 220
<212> TYPE: PRT
<213> ORGANISM: Triticum aestivum

<400> SEQUENCE: 5

Met Glu Arg Ser Arg Gly Leu Leu Leu Val Ala Gly Leu Leu Ala Ala
1               5                   10                  15

Leu Leu Pro Ala Ala Ala Ala Gln Pro Gly Ala Pro Cys Glu Pro Ala
                20                  25                  30

Leu Leu Ala Thr Gln Val Ala Leu Phe Cys Ala Pro Asp Met Pro Thr
            35                  40                  45

Ala Gln Cys Cys Glu Pro Val Val Ala Val Asp Leu Gly Gly Gly
        50                  55                  60

Val Pro Cys Leu Cys Arg Val Ala Ala Glu Pro Gln Leu Val Met Ala
65                  70                  75                  80

Gly Leu Asn Ala Thr His Leu Leu Thr Leu Tyr Ser Ser Cys Gly Gly
                85                  90                  95

Leu Arg Pro Gly Gly Ala His Leu Ala Ala Ala Cys Glu Gly Pro Ala
                100                 105                 110

Pro Pro Ala Ala Val Val Ser Ser Pro Pro Pro Pro Pro Pro Ser
            115                 120                 125

Ala Ala Pro Arg Arg Lys Gln Pro Ala His Asp Ala Pro Pro Pro
        130                 135                 140

Pro Pro Ser Ser Glu Lys Pro Ser Pro Pro Ser Gln Asp His
145                 150                 155                 160

Asp Gly Ala Ala Pro Arg Ala Lys Ala Ala Pro Ala Gln Ala Ala Thr
                165                 170                 175

Ser Thr Leu Ala Pro Ala Ala Ala Thr Ala Pro Pro Gln Ala
            180                 185                 190

Pro His Ser Ala Ala Pro Thr Ala Pro Ser Lys Ala Ala Phe Phe Phe
        195                 200                 205

Val Ala Thr Ala Met Leu Gly Leu Tyr Ile Ile Leu
    210                 215                 220

<210> SEQ ID NO 6
<211> LENGTH: 1527
<212> TYPE: DNA
<213> ORGANISM: Triticum aestivum

<400> SEQUENCE: 6

```
agacttaaac catttagtta caaatatcga tgcacacctt cggtgggggcg ttgtgaaaaa       60 gcatgttttt tgggtcgaca agcccctttt gcaacgtatc ctcttctaat cctattcaga      120
tcattaacat cataagctgc aattgacatg ctcttctgag gatcaggttc atgcaattaa      180
acatcataaa ctgcatcttt gatgtcatcc ttttcctata ttttttccag attattggct      240
```

```
tgcttcgttt tcaatatcag gttctatgat tcgacttctg ttgttgccag taataatttg    300
tagttgctgc ggaatatgaa ctcaaggaga gctgatggtg ctatgaagtt gatttgatgg    360
gaggttgttc tacacctgca cttgctgctc gacttaaata catgccttgg atttcttccc    420
agctctagta cataatattt ttcaaattaa tgttccacga cataaaattt aaatccacaa    480 acatatttttt agtacatgaa caattttcta atatagggca aacatttttc atatacaaac   540
cgatcatttt aatatatggt gaaaatcagt gtaatatatg ctgaaatgtt ttcaaataca    600
tattgaacat atttataata aatggtgaac attttttta ataattgatg accatttta     660 aaatgcatat tgaacatttt ataatataca ctgtacagtt ttataataat cgacgaacat    720
cttttggagt tctgaacatt ttttcaaaa acacaagcca ttttccagga agaatacaaa    780
tgcaaaagaa atgagatatc caaaaagcaa aaagaaaaa caaaacaaaa cagagaaacc    840
tacaggaaaa tccaaacaga aaaggcaaag aaagaacccg aactgggcca ggcaatgttt   900
ccaacggcct cgctcttcct gaacaagaag gccagtcagc ccatgggctg ctcccagtac    960
tcgggccccg ctgtggcagc acgccatgta atagttttcg cgggaatcca acgccgaaat   1020
cgcccgcagc gggaacccga cgtcggtctg gtgcgttctg gcgccttcca gaactctcca   1080
caggctcccg cagccgtccg atcagatcag cacgaagcac gaacattggc gcgcggcgat   1140
attttctttc ctcgcccgac gacggccgca ctgcatttca ttttgaattt caaaattcgg    1200
aaacggaaaa gctttctcgc atcccgaggc gaggcggtta cgggcgccag aggggccacc   1260
ccacccaccc accccccgccc tcacgtgccc cgcgcggccg catccgggcc gtccgcgcgg    1320
acagctggcc gcgcccagcc cgaaccgacg cccaggatcg agcgagggcg gcgcgcccgg    1380
ggcttggctt agcgtccacg ccacctccgg ctatataagc cgcccacac ccgctccccc    1440 tccggcattc cattccgcca ccgcaccacc accaccacca aaccctagcg agcgagcgag   1500
ggagagagag accgccccgc cgcgacg                                      1527
```

<210> SEQ ID NO 7
<211> LENGTH: 4335
<212> TYPE: DNA
<213> ORGANISM: Triticum aestivum
<220> FEATURE:
<221> NAME/KEY: exon
<222> LOCATION: (1528)..(1855)
<220> FEATURE:
<221> NAME/KEY: exon
<222> LOCATION: (2925)..(3008)
<220> FEATURE:
<221> NAME/KEY: exon
<222> LOCATION: (3133)..(3380)

<400> SEQUENCE: 7

```
agacttaaac catttagtta caaatatcga tgcacaccct cggtggggcg ttgtgaaaaa     60
gcatgttttt tgggtcgaca agcccctttt gcaacgtatc ctcttctaat cctattcaga   120
tcattaacat cataagctgc aattgacatg ctcttctgag gatcaggttc atgcaattaa   180
acatcataaa ctgcatcttt gatgtcatcc ttttcctata ttttttccag attattggct   240
tgcttcgttt tcaatatcag gttctatgat tcgacttctg ttgttgccag taataatttg   300
tagttgctgc ggaatatgaa ctcaaggaga gctgatggtg ctatgaagtt gatttgatgg   360
gaggttgttc tacacctgca cttgctgctc gacttaaata catgccttgg atttcttccc   420
agctctagta cataatattt ttcaaattaa tgttccacga cataaaattt aaatccacaa   480 acatatttttt agtacatgaa caattttcta atatagggca aacatttttc atatacaaac  540
```

```
cgatcatttt aatatatggt gaaaatcagt gtaatatatg ctgaaatgtt ttcaaataca    600
tattgaacat atttataata aatggtgaac atttttttta ataattgatg accattttta    660
aaatgcatat tgaacatttt ataatataca ctgtacagtt ttataataat cgacgaacat    720
cttttggagt tctgaacatt tttttcaaaa acacaagcca ttttccagga agaatacaaa    780
tgcaaaagaa atgagatatc caaaaagcaa aaagaaaaa caaaacaaaa cagagaaacc     840
tacaggaaaa tccaaacaga aaaggcaaag aagaacccg aactgggcca ggcaatgttt     900
ccaacggcct cgtcttcct gaacaagaag gccagtcagc ccatgggctg ctcccagtac     960
tcgggccccg ctgtggcagc acgccatgta atagttttcg cgggaatcca acgccgaaat   1020
cgcccgcagc gggaacccga cgtcggtctg gtgcgttctg gcgccttcca gaactctcca   1080
caggctcccg cagccgtccg atcagatcag cacgaagcac gaacattggc gcgcggcgat   1140
attttctttc ctcgcccgac gacggccgca ctgcatttca ttttgaattt caaaattcgg   1200
aaacggaaaa gctttctcgc atcccgaggc gaggcggtta cgggcgccag aggggccacc   1260
ccacccaccc accccgccc tcacgtgccc cgcgcggccg catccgggcc gtccgcgcgg    1320
acagctggcc gcgcccagcc cgaaccgacg cccaggatcg agcgagggcg gcgcgcccgg   1380
ggcttggctt agcgtccacg ccacctccgg ctatataagc cgccccacac ccgctccccc   1440
tccggcattc cattccgcca ccgcaccacc accaccacca aacctagcg agcgagcgag   1500
ggagagagag accgccccgc cgcgacg atg gag aga tcc cgc ggg ctg ctg ctg  1554
                                Met Glu Arg Ser Arg Gly Leu Leu Leu
                                 1               5
gtg gcg ggg ctg ctg gcg gcg ctg ctg ccg gcg gcg gcg cag ccg         1602
Val Ala Gly Leu Leu Ala Ala Leu Leu Pro Ala Ala Ala Gln Pro
 10              15                  20                  25
ggg gcg ccg tgc gag ccc gcg ctg ctg gcg acg cag gtg gcg ctc ttc     1650
Gly Ala Pro Cys Glu Pro Ala Leu Leu Ala Thr Gln Val Ala Leu Phe
                 30                  35                  40
tgc gcg ccc gac atg ccg acg gcc cag tgc tgc gag ccc gtc gtc gcc     1698
Cys Ala Pro Asp Met Pro Thr Ala Gln Cys Cys Glu Pro Val Val Ala
             45                  50                  55
gcc gtc gac ctc ggc ggg ggg gtg ccc tgc ctc tgc cgc gtc gcc gcc     1746
Ala Val Asp Leu Gly Gly Gly Val Pro Cys Leu Cys Arg Val Ala Ala
             60                  65                  70
gag ccg cag ctc gtc atg gcg ggc ctc aac gcc acc cac ctc ctc acg     1794
Glu Pro Gln Leu Val Met Ala Gly Leu Asn Ala Thr His Leu Leu Thr
 75                  80                  85
ctc tac agc tcc tgc ggc ggc ctc cgc ccc ggc ggc gcc cac ctc gcc     1842
Leu Tyr Ser Ser Cys Gly Gly Leu Arg Pro Gly Gly Ala His Leu Ala
 90                  95                 100                 105
gcc gcc tgc gaa g gtacgttgtc cgcctcctcc cctccctccc tccctccctc      1895
Ala Ala Cys Glu
tctctctacg tgctcgcttt cctgcttacc tagtagtacg tagtttccca tgccttcttg   1955
actcgctaga agtgctccgg tttgggtctg ttaatttcct cgctgtacta ccggatctgt   2015
cgtcggcacg gcgcgcggcg tcgggtcctc gccttctccc gtggcgaccg acctgcgcag   2075
cgcgcgcgcg gcctagctag cttcataccg ctgtacctcg acatacacgg agcgatctat   2135
ggtctactct gagtatttcc tcatcgtaga acgcatgcgc cgctcgcgat tgtttcgtcg   2195
attctagatc cgtgcttgtt cccgcgagtt agtatgcatc tgcgtgcata tgccgtacgc   2255
acgcagatgc agagtctgtt gctcgagtta tctactgtga ttcgctcgac catatttgcc   2315
tgttaatttc ctgttcatcg tgcatgcagt agtagtagcc atgtccacgc cttcttgttt   2375
```

```
tgaggcgatc atcgtcgaga tccatggctt tgctttctgc actatcttct gccttgtttt    2435
gttctccgca gtacgtacgt cttgcttggt caaaactgaa aaacgctttg ctgtttgttt    2495
gatcggcaag agctggccgt gcttttggca ccgcagtgcg tcgcctctgc cgcttttgcg    2555
aaacatttcc atgttgatcc tctggcggaa ctactttttc gcgtgcggtt tgcgtggcct    2615
tcctctctcg tgaaaagagg tcgggtcaaa ccaaatggat cgcctcttgg cagagcagcg    2675
gcagcagata gctggccgtc tcgcagcttt ggcagaaccg gtctgtggcc atctgtcgcc    2735
gcctgccacc gtttccctga tgtttgtttc tctctcgcct gccactgttt cttttcttgt    2795
tgcgcacgta cgtcgtcacc tcctcctact ttttgccag ttttgtttac ttttgatgaa     2855
atatacggat gaatcggctg tgattaact ttggctgctg ctgttaatta ctgtggattt     2915 tggatgcag ga  ccc gct ccc ccg gcc gcc gtc gtc agc agc ccc ccg ccc    2965
           Gly Pro Ala Pro Pro Ala Ala Val Val Ser Ser Pro Pro Pro
           110              115                 120 ccg cct cca ccg tcc gcc gca cct cgc cgc aag cag cca gcg c            3008
Pro Pro Pro Pro Ser Ala Ala Pro Arg Arg Lys Gln Pro Ala
   125                 130                 135 gtaagaacct ctccctctcc ctctctctct ccctctcgcc tgcatctcgc tatgtttatc    3068
catgtccata tgttgatcag ccttgtttag ttactaacat gtgcaccgga tcgggttctc    3128 gcag ac  gac gca cca ccg ccg cca ccg ccg tcg agc gag aag ccg tcg     3176
     His Asp Ala Pro Pro Pro Pro Pro Pro Ser Ser Glu Lys Pro Ser
          140                 145                 150 tcc ccg ccg ccg tcc cag gac cac gac ggc gcc gcc ccc cgc gcc aag     3224
Ser Pro Pro Pro Ser Gln Asp His Asp Gly Ala Ala Pro Arg Ala Lys
    155                 160                 165 gcc gcg ccc gcc cag gcg gcc acc tcc acg ctc gcg ccc gcc gcc gcc     3272
Ala Ala Pro Ala Gln Ala Ala Thr Ser Thr Leu Ala Pro Ala Ala Ala
170                 175                 180 gcc acc gcc ccg ccg ccc cag gcg ccg cac tcc gcc gcg ccc acg gcg     3320
Ala Thr Ala Pro Pro Pro Gln Ala Pro His Ser Ala Ala Pro Thr Ala
185                 190                 195                 200 ccg tcc aag gcg gcc ttc ttc ttc gtc gcc acg gcc atg ctc ggc ctc     3368
Pro Ser Lys Ala Ala Phe Phe Phe Val Ala Thr Ala Met Leu Gly Leu
                205                 210                 215 tac atc atc ctc tgagtcgcgc gccgaccccg cgagagaccg tggtccgtcc         3420
Tyr Ile Ile Leu
            220 agtcgcagta gagtagagcg ctcgtcgtct cgttccgttt cgtgcctgtc gccgttcgag    3480 gttcgttttct gcgtgcagtc cggtcgaaga agccggtggg ttttgagtac tagtggtagt   3540 agtagcagca gctatcgttt ctgtccgctc gtacgtgttt gcgtggtcgc ggagaacaat    3600 taattgggtg tttgcgagtc ctctggttaa gatgaaccac tgatgctatg tgatcgatcg    3660 atcggtatga tctgaatgga aatggatcaa gttttgcgtt ctgctgatga tgtgatccat    3720 ttggatctgt gtgggcaac agtttcgctt gcttttgctc tgcgatgaac gaatgcttct    3780 tgcatgcatc ttgtctttgc ttaatttgaa ctgtagaacg gatgcagtac tgatttctgc    3840 ttatgatgtg acgattcgtc gtacgcatat catctcttca aatttgtgta gcagctgttt    3900 gtagcttcca ttctgctatg gacgaatgcc tgttttcac ggagaaccgc gcgcggggac     3960 cgatgcggct ttgtgttgcc atgttgtttt ccacgccagg acaaaataga tggtgcggtt    4020 ttgatcccca atcccaccat caccatgttc cggagagcca catggaactc acgtcaagcg    4080 gtcactttt gcagaatcac tcttaccatt ttacccttt gttgaaacct ctctcctcat      4140
```

| | |
|---|---|
| cccaaaagt tgatgcaaca gtgctatgcg cgcccaccca tgcttttca tatgattgta | 4200 |
| aaatttggat cgattttatc ttttgaaccc taagtccggt ttacaatctg tttgcatgtt | 4260 |
| tatgttcctt gcggcgagga ccattaaaca agactactat tggatatatt tcgacaggct | 4320 |
| ttgaaatccg aattc | 4335 |

<210> SEQ ID NO 8
<211> LENGTH: 1527
<212> TYPE: DNA
<213> ORGANISM: Artificial Sequence
<220> FEATURE:
<223> OTHER INFORMATION: synthesized

<400> SEQUENCE: 8

| | |
|---|---|
| aagcttaaac catttagtta caaatatcga tgcacacctt cggtggggcg ttgtgaaaaa | 60 |
| gcatgttttt tgggtcgaca agccccttt gcaacgtatc ctcttctaat cctattcaga | 120 |
| tcattaacat cataagctgc aattgacatg ctcttctgag gatcaggttc atgcaattaa | 180 |
| acatcataaa ctgcatcttt gatgtcatcc ttttcctata ttttttccag attattggct | 240 |
| tgcttcgttt tcaatatcag gttctatgat tcgacttctg ttgttgccag taataatttg | 300 |
| tagttgctgc ggaatatgaa ctcaaggaga gctgatggtg ctatgaagtt gatttgatgg | 360 |
| gaggttgttc tacacctgca cttgctgctc gacttaaata catgccttgg atttcttccc | 420 |
| agctctagta cataatattt ttcaaattaa tgttccacga cataaaattt aaatccacaa | 480 |
| acatatttt agtacatgaa caatttctta atatagggca acatttttc atatacaaac | 540 |
| cgatcatttt aatatatggt gaaaatcagt gtaatatatg ctgaaatgtt ttcaaataca | 600 |
| tattgaacat atttataata aatggtgaac atttttttta ataattgatg accattttta | 660 |
| aaatgcatat tgaacatttt ataatataca ctgtacagtt ttataataat cgacgaacat | 720 |
| cttttggagt tctgaacatt ttttttcaaaa acacaagcca ttttccagga agaatacaaa | 780 |
| tgcaaaagaa atgagatatc caaaaagcaa aaagaaaaaa caaaacaaaa cagagaaacc | 840 |
| tacaggaaaa tccaaacaga aaaggcaaag aaagaacccg aactgggcca ggcaatgttt | 900 |
| ccaacggcct cgctcttcct gaacaagaag gccagtcagc ccatgggctg ctcccagtac | 960 |
| tcgggccccg ctgtggcagc acgccatgta atagttttcg cgggaatcca acgccgaaat | 1020 |
| cgcccgcagc gggaacccga cgtcggtctg gtgcgttctg gcgccttcca gaactctcca | 1080 |
| caggctcccg cagccgtccg atcagatcag cacgaagcac gaacattggc gcgcggcgat | 1140 |
| atttctttc ctcgcccgac gacggccgca ctgcatttca ttttgaattt caaaattcgg | 1200 |
| aaacggaata gctttctcgc atcccgaggc gaggcggtta cgggcgccag aggggccacc | 1260 |
| ccacccaccc accccgccc tcacgtgccc cgcgcggccg aatccgggcc gtccgcgcgg | 1320 |
| acagctggcc gcgcccagcc cgaaccgacg cccaggatcg agcgagggcg cgcgcccgg | 1380 |
| ggcttggctt agcgtccacg ccacctccgg ctatataagc cgccccacac ccgctccccc | 1440 |
| tccggcattc cattccgcca ccgcaccacc accaccacca aaccctagcg agcgagcgag | 1500 |
| ggagagagag accgccccgc cgcgacg | 1527 |

<210> SEQ ID NO 9
<211> LENGTH: 4335
<212> TYPE: DNA
<213> ORGANISM: Artificial Sequence
<220> FEATURE:
<223> OTHER INFORMATION: synthesized

<400> SEQUENCE: 9

| | |
|---|---|
| aagcttaaac catttagtta caaatatcga tgcacacctt cggtggggcg ttgtgaaaaa | 60 |
| gcatgttttt tgggtcgaca agccccttt gcaacgtatc ctcttctaat cctattcaga | 120 |
| tcattaacat cataagctgc aattgacatg ctcttctgag gatcaggttc atgcaattaa | 180 |
| acatcataaa ctgcatcttt gatgtcatcc ttttcctata ttttttccag attattggct | 240 |
| tgcttcgttt tcaatatcag gttctatgat tcgacttctg ttgttgccag taataatttg | 300 |
| tagttgctgc ggaatatgaa ctcaaggaga gctgatggtg ctatgaagtt gatttgatgg | 360 |
| gaggttgttc tacacctgca cttgctgctc gacttaaata catgccttgg atttcttccc | 420 |
| agctctagta cataatattt ttcaaattaa tgttccacga cataaaattt aaatccacaa | 480 |
| acatattttt agtacatgaa caattttcta atatagggca acatttttc atatacaaac | 540 |
| cgatcatttt aatatatggt gaaaatcagt gtaatatatg ctgaaatgtt ttcaaataca | 600 |
| tattgaacat atttataata aatggtgaac attttttta ataattgatg accatttta | 660 |
| aaatgcatat tgaacatttt ataatataca ctgtacagtt ttataataat cgacgaacat | 720 |
| cttttggagt tctgaacatt tttttcaaaa acacaagcca ttttccagga agaatacaaa | 780 |
| tgcaaaagaa atgagatatc caaaaagcaa aaagaaaaa caaaacaaaa cagagaaacc | 840 |
| tacaggaaaa tccaaacaga aaaggcaaag aaagaacccg aactgggcca ggcaatgttt | 900 |
| ccaacggcct cgctcttcct gaacaagaag gccagtcagc ccatgggctg ctcccagtac | 960 |
| tcgggccccg ctgtggcagc acgccatgta atagttttcg cgggaatcca acgccgaaat | 1020 |
| cgcccgcagc gggaacccga cgtcggtctg gtgcgttctg gcgccttcca gaactctcca | 1080 |
| caggctcccg cagccgtccg atcagatcag cacgaagcac gaacattggc gcgcggcgat | 1140 |
| attttctttc ctcgcccgac gacgccgca ctgcatttca ttttgaattt caaaattcgg | 1200 |
| aaacggaata gctttctcgc atcccgaggc gaggcggtta cgggcgccag aggggccacc | 1260 |
| ccacccaccc accccccgccc tcacgtgccc cgcgcggccg aatccgggcc gtccgcgcgg | 1320 |
| acagctggcc gcgcccagcc cgaaccgacg cccaggatca gcgagggcg gcgcgcccgg | 1380 |
| ggcttggctt agcgtccacg ccacctccgg ctatataagc cgccccacac ccgctccccc | 1440 |
| tccggcattc cattccgcca ccgcaccacc accaccacca aaccctagcg agcgagcgag | 1500 |
| ggagagagag accgcccgc cgcgacgatg gagagatccc gcgggctgct gctggtggcg | 1560 |
| gggctgctgg cggcgctgct gccggcggcg gcggcgcagc cggggggcgcc gtgcgagccc | 1620 |
| gcgctgctgg cgacgcaggt ggcgctcttc tgcgcgcccg acatgccgac ggcccagtgc | 1680 |
| tgcgagcccg tcgtcgccgc cgtcgacctc ggcggcgggg tgccctgcct ctgccgcgtc | 1740 |
| gccgccgagc cgcagctcgt catggcgggc ctcaacgcca cccacctcct cacgctctac | 1800 |
| agctcctgcg gcggcctccg ccccggcggc gcccacctcg ccgccgcctg cgaaggtacg | 1860 |
| ttgtccgcct cctcccctcc ctccctccct ccctctctct ctacgtgctc gctttcctgc | 1920 |
| ttacctagta gtacgtagtt tcccatgcct tcttgactcg ctagaagtgc tccggtttgg | 1980 |
| gtctgttaat ttcctcgctg tactaccgga tctgtcgtcg gcacggcgcg cggcgtcggg | 2040 |
| tcctcgcctt ctcccgtggc gaccgacctg cgcagcgcgc gcgcggccta gctagcttca | 2100 |
| taccgctgta cctcgacata cacggagcga tctatggtct actctgagta tttcctcatc | 2160 |
| gtagaacgca tgcgccgctc gcgattgttt cgtcgattct agatccgtgc ttgttcccgc | 2220 |
| gagttagtat gcatctgcgt gcatatgccg tacgcacgca gatgcagagt ctgttgctcg | 2280 |
| agttatctac tgtcgttcgc tcgaccatat ttgcctgtta atttcctgtt catcgtgcat | 2340 |

-continued

```
gcagtagtag tagccatgtc cacgccttct tgttttgagg cgatcatcgt cgagatccat    2400
ggctttgctt tctgcactat cttctgcctt gttttgttct ccgcagtacg tacgtcttgc    2460
ttggtcaaaa ctgaaaaacg ctttgctgtt tgtttgatcg gcaagagctg gccgtgcttt    2520
tggcaccgca gtgcgtcgcc tctgccgctt tgcgaaaca tttccatgtt gatcctctgg    2580
cggaactact ttttcgcgtg cggtttgcgt ggccttcctc tctcgtgaaa agaggtcggg    2640
tcaaaccaaa tggatcgcct cttggcagag cagcggcagc agatagctgg ccgtctcgca    2700
gctttggcag aaccggtctg tggccatctg tcgccgcctg ccaccgtttc cctgatgttt    2760
gtttctctct cgcctgccac tgtttctttt cttgttgcgc acgtacgtcg tcacctcctc    2820
ctactttttt gccagttttg tttacttttg atgaaatata cggatgaatc ggctggtgat    2880
taactttggc tgctgctgtt aattactgtg gattttggat gcaggacccg ctcccccggc    2940
cgccgtcgtc agcagccccc cgccccgcc tccaccgtcc gccgcacctc gccgcaagca    3000
gccagcgcgt aagaacctct ccctctccct ctctctctcc ctctcgcctg catctcgcta    3060
tgtttatcca tgtccatatg ttgatcagcc ttgtttagtt actaacatgt gcaccggatc    3120
gggttctcgc agacgacgca ccaccgccgc caccgccgtc gagcgagaag ccgtcgtccc    3180
cgccgccgtc ccaggaccac gacggcgccg cccccccgcgc caaggccgcg cccgcccagg    3240
cggccacctc cacgctcgcg cccgccgccg ccgccaccgc cccgccgccc caggcgccgc    3300
actccgccgc gcccacggcg ccgtccaagg cggccttctt cttcgtcgcc acggccatgc    3360
tcggcctcta catcatcctc tgagtcgcgc gccgaccccg cgagagaccg tggtccgtcc    3420
agtcgcagta gagtagagcg ctcgtcgtct cgttccgttt cgtgcctgtc gccgttcgag    3480
gttcgtttct gcgtgcagtc cggtcgaaga agccggtggg ttttgagtac tagtggtagt    3540
agtagcagca gctatcgttt ctgtccgctc gtacgtgttt gcgtggtcgc ggagaacaat    3600
taattgggtg tttgcgagtc ctctggttaa gatgaaccac tgatgctatg tgatcgatcg    3660
atcggtatga tctgaatgga aatggatcaa gttttgcgtt ctgctgatga tgtgatccat    3720
ttggatctgt gtggggcaac agtttcgctt gcttttgctc tgcgatgaac gaatgcttct    3780
tgcatgcatc ttgtctttgc ttaatttgaa ctgtagaacg gatgcagtac tgatttctgc    3840
ttatgatgtg acgattcgtc gtacgcatat catctcttca aatttgtgta gcagctgttt    3900
gtagcttcca ttctgctatg gacgaatgcc tgttttttcac ggagaaccgc gcgcggggac    3960
cgatgcggct ttgtgttgcc atgttgtttt ccacgccagg acaaaataga tggtgcggtt    4020
ttgatcccca atcccaccat caccatgttc cggagagcca catggaactc acgtcaagcg    4080 gtcactttt gcagaatcac tcttaccatt ttacccttt gttgaaacct ctctcctcat    4140
ccccaaaagt tgatgcaaca gtgctatgcg cgcccaccca tgcttttca tatgattgta    4200 aaatttggat cgattttatc ttttgaaccc taagtccggt ttacaatctg tttgcatgtt    4260
tatgttcctt gcggcgagga ccattaaaca agactactat tggatatatt tcgacaggct    4320
ttgaaatccg aattc                                                   4335
```

<210> SEQ ID NO 10
<211> LENGTH: 241
<212> TYPE: DNA
<213> ORGANISM: Hordeum vulgare
<220> FEATURE:
<221> NAME/KEY: variation
<222> LOCATION: (121)..(121)
<223> OTHER INFORMATION: a or c

<400> SEQUENCE: 10

| | | |
|---|---|---|
| ttttacagca gcaacaacaa caacaaaacc caagtcacca gtaagagctt acacgcagcc | 60 | |
| tgagggcggg cacgacacaa acgggtataa ggttgacacg tacatccaac acagggcaaa | 120 | |
| maagttccgt ttcaaggggt cgcgagcccg gagttccacc gctggaatcg gtcaatccgg | 180 | |
| ttctgcacac acacagccgt tacactgcct acaaacaagt ttaagggata catacacact | 240 | |
| g | 241 | |

```
<210> SEQ ID NO 11
<211> LENGTH: 274
<212> TYPE: DNA
<213> ORGANISM: Triticum aestivum
<220> FEATURE:
<221> NAME/KEY: variation
<222> LOCATION: (34)..(34)
<223> OTHER INFORMATION: c (Chris) or t (Gladius)
<220> FEATURE:
<221> NAME/KEY: variation
<222> LOCATION: (54)..(54)
<223> OTHER INFORMATION: g (Chris) or t (Gladius)
<220> FEATURE:
<221> NAME/KEY: variation
<222> LOCATION: (83)..(83)
<223> OTHER INFORMATION: t (Chris) or c (Gladius)
<220> FEATURE:
<221> NAME/KEY: variation
<222> LOCATION: (130)..(130)
<223> OTHER INFORMATION: g (Chris) or a (Gladius)
<220> FEATURE:
<221> NAME/KEY: variation
<222> LOCATION: (165)..(165)
<223> OTHER INFORMATION: a (Chris) or gap (Gladius)
<220> FEATURE:
<221> NAME/KEY: variation
<222> LOCATION: (174)..(174)
<223> OTHER INFORMATION: a (Chris) or t (Gladius at 173)
<220> FEATURE:
<221> NAME/KEY: variation
<222> LOCATION: (186)..(186)
<223> OTHER INFORMATION: t (Chris) or g (Gladius at 185)
<220> FEATURE:
<221> NAME/KEY: variation
<222> LOCATION: (253)..(253)
<223> OTHER INFORMATION: t (Chris) or c (Gladius at 252)
```

<400> SEQUENCE: 11

| | | |
|---|---|---|
| atgatggatg gacggatgat gctctgtggt gccytgtatt tatatttgtt gagktctttg | 60 | |
| atacaggatg atatgtctcc aaygtatcta taatttttg ttgttccatg ttgttatatt | 120 | |
| atcattttgr atgttttaca atcatttat aatcattcta tatcattttt tgtwactaac | 180 | |
| ctattkacat agtgccaagt gctagttgtt gttttctgct tgtttttac atcgcaggaa | 240 | |
| atcaatacca aayggagtcc aaacgcagca aaac | 274 | |

```
<210> SEQ ID NO 12
<211> LENGTH: 273
<212> TYPE: DNA
<213> ORGANISM: Triticum aestivum
```

<400> SEQUENCE: 12

| | | |
|---|---|---|
| atgatggatg gacggatgat gctctgtggt gccttgtatt tatatttgtt gagttctttg | 60 | |
| atacaggatg atatgtctcc aacgtatcta taatttttg ttgttccatg ttgttatatt | 120 | |
| atcattttga atgttttaca atcatttat aatcattcta tatctttttt gttactaacc | 180 | |
| tattgacata gtgccaagtg ctagttgttg ttttctgctt gttttttaca tcgcaggaaa | 240 | |
| tcaataccaa acggagtcca aacgcagcaa aac | 273 | |

<210> SEQ ID NO 13
<211> LENGTH: 274
<212> TYPE: DNA
<213> ORGANISM: Triticum aestivum

<400> SEQUENCE: 13

```
atgatggatg gacggatgat gctctgtggt gccctgtatt tatatttgtt gaggtctttg      60
atacaggatg atatgtctcc aatgtatcta taattttttg ttgttccatg ttgttatatt     120
atcattttgg atgttttaca atcattttat aatcattcta tatcattttt tgtaactaac     180
ctatttacat agtgccaagt gctagttgtt gttttctgct tgttttttac atcgcaggaa     240
atcaatacca aatggagtcc aaacgcagca aaac                                 274
```

<210> SEQ ID NO 14
<211> LENGTH: 415
<212> TYPE: DNA
<213> ORGANISM: Aegilops speltoides

<400> SEQUENCE: 14

```
accaggcctc ccgacCCCac cgtgagcatg cgcttcgcgt gcacggcggc accactccgc      60
tacggcctcg gccttcttc ttccttctcc gacaacgccg cctcctcgtg ttgttcttct     120
tcgtctcgga ttctatctac aaggagctag ctagctagcg cgattcactg atctctagct     180
ggggaggggt acaaccgtac aagcatggag cccggagctt tagcgacgtg cggggcggtg     240
gccttctcct gggagcagga gccggggggtg tccaaggaga gcccggcggc cgaggcgagg     300
aagccctccg gtgaaggac gccggacagc accaggaagg tggaggtgca gacggacagg     360
ctgctcgtgc ccctccacc gggagggccc ggagcgccgt ctctgtcgcc ggtga          415
```

<210> SEQ ID NO 15
<211> LENGTH: 281
<212> TYPE: DNA
<213> ORGANISM: Triticum aestivum
<220> FEATURE:
<221> NAME/KEY: variation
<222> LOCATION: (224)..(224)
<223> OTHER INFORMATION: t (Chris) or a (Gladius)
<220> FEATURE:
<221> NAME/KEY: variation
<222> LOCATION: (229)..(229)
<223> OTHER INFORMATION: c (Chris) or a (Gladius)
<220> FEATURE:
<221> NAME/KEY: variation
<222> LOCATION: (253)..(253)
<223> OTHER INFORMATION: a (Chris) or c (Gladius)

<400> SEQUENCE: 15

```
ttaatagtgt tccgccctgc gtggcacaga ccgtaacgaa tgattgtacg aacgtttttc      60
actaatcatt acataggtgt ggtttaagaa aaaatcaacc accttaacgc cgtaatcccc     120
tctacagaat aaccacacaa gtcatgaaaa ggaactatta acaaaaatag atgataaaat     180
aaatctcaaa tccaaattca taagcacct ctagtctata aacwcgacma atctagctat     240
gtttagtact tcmtccgttc caaaatactt gtcgtggttt t                         281
```

<210> SEQ ID NO 16
<211> LENGTH: 281
<212> TYPE: DNA
<213> ORGANISM: Triticum aestivum

<400> SEQUENCE: 16

```
ttaatagtgt tccgccctgc gtggcacaga ccgtaacgaa tgattgtacg aacgtttttc      60
```

```
actaatcatt acataggtgt ggtttaagaa aaaatcaacc accttaacgc cgtaatcccc    120
tctacagaat aaccacacaa gtcatgaaaa ggaactatta acaaaaatag atgataaaat    180
aaatctcaaa tccaaattca taaagcacct ctagtctata aacacgacaa atctagctat    240
gtttagtact tcctccgttc caaaatactt gtcgtggttt t                       281
```

<210> SEQ ID NO 17
<211> LENGTH: 281
<212> TYPE: DNA
<213> ORGANISM: Triticum aestivum

<400> SEQUENCE: 17

```
ttaatagtgt tccgccctgc gtggcacaga ccgtaacgaa tgattgtacg aacgttttc     60 actaatcatt acataggtgt ggtttaagaa aaaatcaacc accttaacgc cgtaatcccc    120
tctacagaat aaccacacaa gtcatgaaaa ggaactatta acaaaaatag atgataaaat    180
aaatctcaaa tccaaattca taaagcacct ctagtctata aactcgacca atctagctat    240
gtttagtact tcatccgttc caaaatactt gtcgtggttt t                       281
```

<210> SEQ ID NO 18
<211> LENGTH: 199
<212> TYPE: DNA
<213> ORGANISM: Triticum aestivum
<220> FEATURE:
<221> NAME/KEY: variation
<222> LOCATION: (101)..(101)
<223> OTHER INFORMATION: t (Gladius) or c (Chris)

<400> SEQUENCE: 18

```
atgctcatgg tgcacgcgac gagaagtggc cagagacaat ccttgaccat gatcgaataa     60
tatggctcgg ggatttgaat taccggatag cgctttccta ycgctctgtg aaggctttgg    120
ttgagatgca caattggaaa caattgttgg aaaaagatca gcttcgtata gagcaaaggt    180
ttggtcgggt attcgcggg                                                 199
```

<210> SEQ ID NO 19
<211> LENGTH: 199
<212> TYPE: DNA
<213> ORGANISM: Triticum aestivum

<400> SEQUENCE: 19

```
atgctcatgg tgcacgcgac gagaagtggc cagagacaat ccttgaccat gatcgaataa     60
tatggctcgg ggatttgaat taccggatag cgctttccta tcgctctgtg aaggctttgg    120
ttgagatgca caattggaaa caattgttgg aaaaagatca gcttcgtata gagcaaaggt    180
ttggtcgggt attcgcggg                                                 199
```

<210> SEQ ID NO 20
<211> LENGTH: 199
<212> TYPE: DNA
<213> ORGANISM: Triticum aestivum

<400> SEQUENCE: 20

```
atgctcatgg tgcacgcgac gagaagtggc cagagacaat ccttgaccat gatcgaataa     60
tatggctcgg ggatttgaat taccggatag cgctttccta ccgctctgtg aaggctttgg    120
ttgagatgca caattggaaa caattgttgg aaaaagatca gcttcgtata gagcaaaggt    180
ttggtcgggt attcgcggg                                                 199
```

<210> SEQ ID NO 21
<211> LENGTH: 198
<212> TYPE: DNA
<213> ORGANISM: Triticum aestivum
<220> FEATURE:
<221> NAME/KEY: variation
<222> LOCATION: (101)..(101)
<223> OTHER INFORMATION: a (Gladius) or g (Chris)
<220> FEATURE:
<221> NAME/KEY: variation
<222> LOCATION: (165)..(165)
<223> OTHER INFORMATION: c (Gladius) or t (Chris)

<400> SEQUENCE: 21
tatatgaatt aggctttgcg gaccggaagt acaacgccaa cttgcttggt gttcctgcac      60
tgctgcttga gaccttgatg tgcaaagtta tgaacatatc rgcgtaacta gggaaagtga    120
atatgtataa tactagcaaa caagttagat taggctaaat cgcgytatttt tccggtgagc   180 tgggatttcc tggccagt                                                  198

<210> SEQ ID NO 22
<211> LENGTH: 198
<212> TYPE: DNA
<213> ORGANISM: Triticum aestivum

<400> SEQUENCE: 22
tatatgaatt aggctttgcg gaccggaagt acaacgccaa cttgcttggt gttcctgcac      60
tgctgcttga gaccttgatg tgcaaagtta tgaacatatc agcgtaacta gggaaagtga    120
atatgtataa tactagcaaa caagttagat taggctaaat cgcgctattt tccggtgagc    180
tgggatttcc tggccagt                                                  198

<210> SEQ ID NO 23
<211> LENGTH: 198
<212> TYPE: DNA
<213> ORGANISM: Triticum aestivum

<400> SEQUENCE: 23
tatatgaatt aggctttgcg gaccggaagt acaacgccaa cttgcttggt gttcctgcac      60
tgctgcttga gaccttgatg tgcaaagtta tgaacatatc ggcgtaacta gggaaagtga    120
atatgtataa tactagcaaa caagttagat taggctaaat cgcgttattt tccggtgagc    180
tgggatttcc tggccagt                                                  198

<210> SEQ ID NO 24
<211> LENGTH: 58
<212> TYPE: DNA
<213> ORGANISM: Triticum aestivum
<220> FEATURE:
<221> NAME/KEY: variation
<222> LOCATION: (22)..(22)
<223> OTHER INFORMATION: t (Chris) or c (Gladius)

<400> SEQUENCE: 24
atgtggacct tggcaagatt tyatatgcat tttgagagaa atagaagtaa tgtgattg       58

<210> SEQ ID NO 25
<211> LENGTH: 56
<212> TYPE: DNA
<213> ORGANISM: Triticum aestivum
<220> FEATURE:
<221> NAME/KEY: variation
<222> LOCATION: (27)..(27)
<223> OTHER INFORMATION: g (Chris) or a (Gladius)

<400> SEQUENCE: 25
ggttttgggt ttactttgag tcatagraga agccatacta taaagagggg gttgct   56

<210> SEQ ID NO 26
<211> LENGTH: 53
<212> TYPE: DNA
<213> ORGANISM: Triticum aestivum
<220> FEATURE:
<221> NAME/KEY: variation
<222> LOCATION: (31)..(31)
<223> OTHER INFORMATION: t (Chris) or g (Gladius)

<400> SEQUENCE: 26
acttgattgt acttttggt tagcaacaat kgcaatgact tgacaaggga aag   53

<210> SEQ ID NO 27
<211> LENGTH: 50
<212> TYPE: DNA
<213> ORGANISM: Triticum aestivum
<220> FEATURE:
<221> NAME/KEY: variation
<222> LOCATION: (30)..(30)
<223> OTHER INFORMATION: g (Chris) or c (Gladius)

<400> SEQUENCE: 27
ctcgccttgg ctatagggtc ctctgtgags aaggaaaagg tcgaggaggc   50

<210> SEQ ID NO 28
<211> LENGTH: 59
<212> TYPE: DNA
<213> ORGANISM: Triticum aestivum
<220> FEATURE:
<221> NAME/KEY: variation
<222> LOCATION: (38)..(38)
<223> OTHER INFORMATION: a (Chris) or g (Gladius)

<400> SEQUENCE: 28
caacgctatc ccttaaaacg gatacactat ccatccgrga agcatgttcg gatgtgttg   59

<210> SEQ ID NO 29
<211> LENGTH: 39
<212> TYPE: DNA
<213> ORGANISM: Triticum aestivum
<220> FEATURE:
<221> NAME/KEY: variation
<222> LOCATION: (20)..(20)
<223> OTHER INFORMATION: a (Chris) or G (Gladius)

<400> SEQUENCE: 29
ctcgccgccg cctgcgaagr tacgttgtcc gcctcctcc   39

<210> SEQ ID NO 30
<211> LENGTH: 1618
<212> TYPE: DNA
<213> ORGANISM: Zea mays
<220> FEATURE:
<221> NAME/KEY: CDS
<222> LOCATION: (108)..(1430)

<400> SEQUENCE: 30
ggcacgagcc ggcgagccca ctcggcagtc ggcacaacca cacacacctc cacccactct   60
ctgagataag tgaagcatct cgcgcactgt cgcagtcgca gacggag atg atg aag   116
                                                  Met Met Lys
                                                   1 cac tcg agc agc ttg tgc ttg ctc ttc ctc ttg gcg ctc tgc acc acc   164

|   |   |   |   |   |   |   |   |   |   |   |   |   |   |   |   |
|---|---|---|---|---|---|---|---|---|---|---|---|---|---|---|---|
| His | Ser | Ser | Ser | Leu | Cys | Leu | Leu | Phe | Leu | Leu | Ala | Leu | Cys | Thr | Thr |
|   | 5 |   |   |   | 10 |   |   |   |   | 15 |   |   |   |   |   |

```
ctg ctg gcc tgc ggc ctg gtc cag gca caa gtc ctc ttc cag ggg ttt      212
Leu Leu Ala Cys Gly Leu Val Gln Ala Gln Val Leu Phe Gln Gly Phe
 20          25              30              35 aac tgg gag tcg tgc aag cag cag gga ggc tgg tac aac agg ctc aag      260
Asn Trp Glu Ser Cys Lys Gln Gln Gly Gly Trp Tyr Asn Arg Leu Lys
             40              45              50 gcc cag gtc gac gac atc gcc aag gcc ggc gtc acg cac gtc tgg ctg      308
Ala Gln Val Asp Asp Ile Ala Lys Ala Gly Val Thr His Val Trp Leu
                 55              60              65 cct cca ccc tcg cac tcc gtc tcg cca caa ggc tac atg cca ggc cgc      356
Pro Pro Pro Ser His Ser Val Ser Pro Gln Gly Tyr Met Pro Gly Arg
         70              75              80 cta tac gac ctg gac gcg tcc aag tac ggc acg gcg gcg gag ctc aag      404
Leu Tyr Asp Leu Asp Ala Ser Lys Tyr Gly Thr Ala Ala Glu Leu Lys
     85              90              95 tcc ctg ata gcg gcg ttc cac ggc agg ggc gtg cag tgc gtg gcg gac      452
Ser Leu Ile Ala Ala Phe His Gly Arg Gly Val Gln Cys Val Ala Asp
100             105             110             115 atc gtc atc aac cac cgg tgc gcg gaa aag aag gac gcg cgc ggc gtg      500
Ile Val Ile Asn His Arg Cys Ala Glu Lys Lys Asp Ala Arg Gly Val
             120             125             130 tac tgc atc ttc gag ggc ggg act ccc gac gac cgc ctg gac tgg ggc      548
Tyr Cys Ile Phe Glu Gly Gly Thr Pro Asp Asp Arg Leu Asp Trp Gly
                 135             140             145 ccc ggg atg atc tgc agc gac gac acg cag tac tcg gac ggg acg ggg      596
Pro Gly Met Ile Cys Ser Asp Asp Thr Gln Tyr Ser Asp Gly Thr Gly
         150             155             160 cac cgc gac acg ggc gag ggg ttc gcg gcg gcg ccc gac atc gac cac      644
His Arg Asp Thr Gly Glu Gly Phe Ala Ala Ala Pro Asp Ile Asp His
     165             170             175 ctc aac ccg cgc gtg cag cgg gag ctc tcc gcc tgg ctc aac tgg ctc      692
Leu Asn Pro Arg Val Gln Arg Glu Leu Ser Ala Trp Leu Asn Trp Leu
180             185             190             195 agg tcc gac gcc gtg ggg ttc gac ggc tgg cgc ctc gac ttc gcc aag      740
Arg Ser Asp Ala Val Gly Phe Asp Gly Trp Arg Leu Asp Phe Ala Lys
             200             205             210 ggc tac tcg ccg gcc gtc gcc aga atg tac gtg gag agc acg ggg ccg      788
Gly Tyr Ser Pro Ala Val Ala Arg Met Tyr Val Glu Ser Thr Gly Pro
                 215             220             225 ccg agc ttc gtc gtc gcg gag ata tgg aac tcg ctg agc tac agc ggg      836
Pro Ser Phe Val Val Ala Glu Ile Trp Asn Ser Leu Ser Tyr Ser Gly
         230             235             240 gac ggc aag ccg gcg ccc aac cag gac cag tgc cgg cag gag ctg ctg      884
Asp Gly Lys Pro Ala Pro Asn Gln Asp Gln Cys Arg Gln Glu Leu Leu
     245             250             255 gac tgg acg cgg gcc gtc ggc ggg ccc gcc atg gcg ttc gac ttc ccc      932
Asp Trp Thr Arg Ala Val Gly Gly Pro Ala Met Ala Phe Asp Phe Pro
260             265             270             275 acc aag ggc ctg ctg cag gcg ggc gtg cag ggg gag ctg tgg cgg ctg      980
Thr Lys Gly Leu Leu Gln Ala Gly Val Gln Gly Glu Leu Trp Arg Leu
             280             285             290 cgc gac agc tcc ggc aac gcg gcc ggc ctg atc ggg tgg gcg ccc gag     1028
Arg Asp Ser Ser Gly Asn Ala Ala Gly Leu Ile Gly Trp Ala Pro Glu
                 295             300             305 aag gcc gtc acc ttc gtc gac aac cat gac acc ggg tcg acg cag aag     1076
Lys Ala Val Thr Phe Val Asp Asn His Asp Thr Gly Ser Thr Gln Lys
         310             315             320
```

```
ctc tgg ccg ttc cca tcc gac aag gtc atg cag ggc tac gcc tac atc    1124
Leu Trp Pro Phe Pro Ser Asp Lys Val Met Gln Gly Tyr Ala Tyr Ile
    325                 330                 335 ctc acc cat cca gga gtc ccc tgc att ttc tac gac cac atg ttc gac    1172
Leu Thr His Pro Gly Val Pro Cys Ile Phe Tyr Asp His Met Phe Asp
340                 345                 350                 355 tgg aac ctg aag cag gag ata tcc acg ctg tct gcc atc agg gcg cgg    1220
Trp Asn Leu Lys Gln Glu Ile Ser Thr Leu Ser Ala Ile Arg Ala Arg
                360                 365                 370 aac ggc atc cgc gcc ggg agc aag ctg cgg atc ctc gtg gcg gac gcg    1268
Asn Gly Ile Arg Ala Gly Ser Lys Leu Arg Ile Leu Val Ala Asp Ala
            375                 380                 385 gac gcg tac gtg gcc gtc gtc gac gag aag gtc atg gtg aag atc ggg    1316
Asp Ala Tyr Val Ala Val Val Asp Glu Lys Val Met Val Lys Ile Gly
        390                 395                 400 aca agg tac ggc gtg agc agc gtg gtc ccg tcg gat ttc cac ccg gcg    1364
Thr Arg Tyr Gly Val Ser Ser Val Val Pro Ser Asp Phe His Pro Ala
    405                 410                 415 gcg cac ggc aag gac tac tgc gtc tgg gag aaa gcg agc ctc cgc gtc    1412
Ala His Gly Lys Asp Tyr Cys Val Trp Glu Lys Ala Ser Leu Arg Val
420                 425                 430                 435 ccg gcg ggg cgc cac ctc tagcagctca gattgctcag tcttgtgctg           1460
Pro Ala Gly Arg His Leu
                440 cattgcaaac acagcagcac gacactgcat aacgtctttt ccttaatttc ctgaatttta   1520 ccttttccta gttcaatttc atatatgtat ttctacatgt acacactatc acaatcagat   1580 aaataaacaa gcttggtcaa aaaaaaaaaa aaaaaaaa                           1618

<210> SEQ ID NO 31
<211> LENGTH: 441
<212> TYPE: PRT
<213> ORGANISM: Zea mays

<400> SEQUENCE: 31

Met Met Lys His Ser Ser Ser Leu Cys Leu Leu Phe Leu Leu Ala Leu
1               5                   10                  15

Cys Thr Thr Leu Leu Ala Cys Gly Leu Val Gln Ala Gln Val Leu Phe
            20                  25                  30

Gln Gly Phe Asn Trp Glu Ser Cys Lys Gln Gln Gly Gly Trp Tyr Asn
        35                  40                  45

Arg Leu Lys Ala Gln Val Asp Asp Ile Ala Lys Ala Gly Val Thr His
    50                  55                  60

Val Trp Leu Pro Pro Ser His Ser Val Ser Pro Gln Gly Tyr Met
65                  70                  75                  80

Pro Gly Arg Leu Tyr Asp Leu Asp Ala Ser Lys Tyr Gly Thr Ala Ala
                85                  90                  95

Glu Leu Lys Ser Leu Ile Ala Ala Phe His Gly Arg Gly Val Gln Cys
            100                 105                 110

Val Ala Asp Ile Val Ile Asn His Arg Cys Ala Glu Lys Lys Asp Ala
        115                 120                 125

Arg Gly Val Tyr Cys Ile Phe Glu Gly Gly Thr Pro Asp Asp Arg Leu
    130                 135                 140

Asp Trp Gly Pro Gly Met Ile Cys Ser Asp Asp Thr Gln Tyr Ser Asp
145                 150                 155                 160

Gly Thr Gly His Arg Asp Thr Gly Glu Gly Phe Ala Ala Ala Pro Asp
                165                 170                 175
```

Ile Asp His Leu Asn Pro Arg Val Gln Arg Glu Leu Ser Ala Trp Leu
            180                 185                 190

Asn Trp Leu Arg Ser Asp Ala Val Gly Phe Asp Gly Trp Arg Leu Asp
        195                 200                 205

Phe Ala Lys Gly Tyr Ser Pro Ala Val Ala Arg Met Tyr Val Glu Ser
    210                 215                 220

Thr Gly Pro Pro Ser Phe Val Val Ala Glu Ile Trp Asn Ser Leu Ser
225                 230                 235                 240

Tyr Ser Gly Asp Gly Lys Pro Ala Pro Asn Gln Asp Gln Cys Arg Gln
                245                 250                 255

Glu Leu Leu Asp Trp Thr Arg Ala Val Gly Gly Pro Ala Met Ala Phe
            260                 265                 270

Asp Phe Pro Thr Lys Gly Leu Leu Gln Ala Gly Val Gln Gly Glu Leu
        275                 280                 285

Trp Arg Leu Arg Asp Ser Ser Gly Asn Ala Ala Gly Leu Ile Gly Trp
    290                 295                 300

Ala Pro Glu Lys Ala Val Thr Phe Val Asp Asn His Asp Thr Gly Ser
305                 310                 315                 320

Thr Gln Lys Leu Trp Pro Phe Pro Ser Asp Lys Val Met Gln Gly Tyr
                325                 330                 335

Ala Tyr Ile Leu Thr His Pro Gly Val Pro Cys Ile Phe Tyr Asp His
            340                 345                 350

Met Phe Asp Trp Asn Leu Lys Gln Glu Ile Ser Thr Leu Ser Ala Ile
        355                 360                 365

Arg Ala Arg Asn Gly Ile Arg Ala Gly Ser Lys Leu Arg Ile Leu Val
    370                 375                 380

Ala Asp Ala Asp Ala Tyr Val Ala Val Asp Glu Lys Val Met Val
385                 390                 395                 400

Lys Ile Gly Thr Arg Tyr Gly Val Ser Ser Val Pro Ser Asp Phe
                405                 410                 415

His Pro Ala Ala His Gly Lys Asp Tyr Cys Val Trp Glu Lys Ala Ser
            420                 425                 430

Leu Arg Val Pro Ala Gly Arg His Leu
        435                 440

<210> SEQ ID NO 32
<211> LENGTH: 55
<212> TYPE: DNA
<213> ORGANISM: Triticum aestivum
<220> FEATURE:
<221> NAME/KEY: variation
<222> LOCATION: (30)..(30)
<223> OTHER INFORMATION: c (Gladius) or a (Chris)

<400> SEQUENCE: 32
atcacattgc acaagttaat agtccggtam tgggtaatta cctttggact ttcca                55

<210> SEQ ID NO 33
<211> LENGTH: 61
<212> TYPE: DNA
<213> ORGANISM: Triticum aestivum
<220> FEATURE:
<221> NAME/KEY: variation
<222> LOCATION: (27)..(27)
<223> OTHER INFORMATION: a (Gladius) or t (Chris)

<400> SEQUENCE: 33
tgtttctgct gcttgctctg cttatawaat gataatgata tgtgcgaatg gtctgttcat        60
g    61

<210> SEQ ID NO 34
<211> LENGTH: 45
<212> TYPE: DNA
<213> ORGANISM: Artificial Sequence
<220> FEATURE:
<223> OTHER INFORMATION: Flanking marker amplicon

<400> SEQUENCE: 34
ggttttccct agtagtgtga ggrgaacgcc tcatcccact cgctc    45

<210> SEQ ID NO 35
<211> LENGTH: 61
<212> TYPE: DNA
<213> ORGANISM: Artificial Sequence
<220> FEATURE:
<223> OTHER INFORMATION: Flanking marker 007-0011.1 amplicon

<400> SEQUENCE: 35
gtatatacta gtaaatcaat aaggtcgatr ctaaagatag aaaaatacct gaagtggtgc    60
c    61

<210> SEQ ID NO 36
<211> LENGTH: 44
<212> TYPE: DNA
<213> ORGANISM: Artificial Sequence
<220> FEATURE:
<223> OTHER INFORMATION: amplicon

<400> SEQUENCE: 36
ggcctaaaat ttgagcccga aggttgrgcc gggcttgggc ttga    44

<210> SEQ ID NO 37
<211> LENGTH: 79
<212> TYPE: DNA
<213> ORGANISM: Artificial Sequence
<220> FEATURE:
<223> OTHER INFORMATION: amplicon

<400> SEQUENCE: 37
tcattttgaa tttcaaaatt cggaaacgga awagctttct cgcatcccga ggcgaggcgg    60
ttacgggcgc cagaggggc    79

<210> SEQ ID NO 38
<211> LENGTH: 196
<212> TYPE: DNA
<213> ORGANISM: Triticum aestivum

<400> SEQUENCE: 38
tgtcgccgtt cgaggttcgt ttctgcgtgc agtccggtcg aagaagccgg tgggttttga    60
gtactagtgg tagtagtagc agcagctatc gtttctgtcc gctcgtacgt gtttgcgtgg    120
tcgcggagaa caattaattg ggtgtttgcg agtcctctgg ttaagatgaa ccactgatgc    180
tatgtgatcg atcgat    196

<210> SEQ ID NO 39
<211> LENGTH: 228
<212> TYPE: PRT
<213> ORGANISM: Brachypodium distachyon

<400> SEQUENCE: 39

Met Glu Arg Ser His His Leu Leu Leu Val Leu Gly Leu Leu Ala Ala

```
           1               5                  10                 15
         Leu Leu Pro Ala Ala Ala Thr Phe Gly Thr Thr Gln Pro Glu Pro
                         20                  25                 30

Gly Ala Pro Cys Glu Pro Thr Leu Leu Ala Thr Gln Val Ser Leu Phe
                     35                  40                 45

Cys Ala Pro Asp Met Pro Thr Ala Gln Cys Cys Glu Pro Val Val Ala
          50                  55                  60

Ser Val Asp Leu Gly Gly Gly Val Pro Cys Leu Cys Arg Val Ala Ala
          65                  70                  75                  80

Glu Pro Gln Leu Val Met Ala Gly Leu Asn Ala Thr His Leu Leu Thr
                             85                  90                  95

Leu Tyr Thr Ser Cys Gly Gly Leu Arg Pro Gly Gly Ala His Leu Ala
                         100                 105                110

Ala Ala Cys Glu Gly Pro Ala Pro Ala Ala Val Val Ser Ala Pro
                     115                 120                 125

Pro Pro Ser Ala Ala Pro Arg Arg Lys Gln Pro Ala His Glu Ala Pro
          130                 135                 140

Pro Pro Pro Pro Ser Thr Glu Lys Pro Ser Pro Pro Gln Gln Asp
         145                 150                 155                 160

Asn Val Thr Ala His Gly Lys Ala Ile Pro Thr His Ala Ala Thr Ser
                         165                 170                 175

Pro Leu Ala Pro Ala Ala Ser Met Ile His Met Ser Pro Pro Pro Ala
                     180                 185                 190

Cys Asn Pro Cys Ser Gly Ser Ala Ala Ser Ala Glu Gly Pro Leu
                     195                 200                 205

Leu Ile Ala Ala Leu Leu Leu Val Ile Thr Ala Ile Ile Val Gly Thr
          210                 215                 220

Leu Asp Asp Lys
         225

<210> SEQ ID NO 40
         <211> LENGTH: 228
         <212> TYPE: PRT
         <213> ORGANISM: Oryza sativa

<400> SEQUENCE: 40

Met Glu Arg Ser His Leu Ala Val Leu Leu Gly Leu Leu Ala Phe Ala
         1               5                   10                  15

Ala Gly Val Pro Ala Ala Ala Ala Thr Ala Val Glu Gly Ala Gln
                     20                  25                  30

Ala Ala Thr Ala Glu Ala Ser Cys Glu Pro Ser Ile Leu Ala Thr Gln
                     35                  40                  45

Val Ser Leu Phe Cys Ala Pro Asp Met Pro Thr Ala Gln Cys Cys Glu
          50                  55                  60

Pro Val Val Ala Ser Val Asp Leu Gly Gly Gly Val Pro Cys Leu Cys
          65                  70                  75                  80

Arg Val Ala Ala Glu Pro Gln Leu Ile Ile Ser Gly Leu Asn Ala Thr
                         85                  90                  95

His Leu Leu Thr Leu Tyr Ala Ala Cys Gly Gly Leu Arg Pro Gly Gly
                     100                 105                 110

Ala Arg Leu Ala Ala Ala Cys Glu Gly Pro Ala Pro Pro Ala Ser Ile
                     115                 120                 125

Val Thr Ala Pro Pro Pro Val Ala Phe Arg Arg Lys Pro Pro Ala
                     130                 135                 140
```

Arg Glu Ala Pro Pro Pro Pro Ala Ala Glu Lys Leu Ser Pro Pro
145                 150                 155                 160

Pro Gln Gln His Asp Asp Ser Asp His Asn Lys Arg Val Gly Pro Leu
            165                 170                 175

Pro Arg Gly Ser Pro Pro Tyr Ala Gln Ser Val Pro Val Gly Pro
        180                 185                 190

Ala Ala Ala Pro Pro Pro Arg Ser Gly Ala Ser Ser Ser Leu Gln
        195                 200                 205

Ala Pro Leu Ala Ala Thr Thr Thr Ile Val Ala Ile Thr Leu Ile Ala
    210                 215                 220

Ala Ala Gln Tyr
225

<210> SEQ ID NO 41
<211> LENGTH: 902
<212> TYPE: DNA
<213> ORGANISM: Hordeum vulgare

<400> SEQUENCE: 41
cgcacatcaa cataaactca tcagatggga ataatcggat ctacgaagga cataaaactc      60
tttaatctca tgacaacgcc agaagagcaa gagtaaatat attctcataa aaacaatga     120
acactagatg atgacgaaga acataagatt cttcaaggag aaattgcggc agcggagatg     180
gcagccggag gcgaggggc caaaaactct gttgcggcgg cagcggtagc cttggtgaaa     240
cccacacgtt tgcacaccat ataagttgtt tgcaagggtt acatgggcct cgctctcgtg     300
aaaaagaagg tcatacatgg gtcttggtct cgtgcaaaac gaaaggtcag cagtccatgg     360
gccggaggaa aaaccgggca acaacacgcc atgtgtgttt tcgcgggaac ccaattccga     420
aatcactcac cggcacctcg tcccgatgcc ttccagaacg ttctacgtgc ttccacaggg     480
ccagcccagc cgtgggatca gatcaggatc agcacgaaca ttgaagctag cgcggcgata     540
tttttcccag cctccgcctc gctcgacgac tgcatttcat ttcgaaaaca aaaaaaagag     600
cttctcctt ctcatcccga gcgccagagg agcaccagaa aggccaccca cccaccctca     660
cgtaccgccc tcgcacccgc gcggccacat ctgggccgtc cacttgggca gctggccgtt     720
ccattcccga actgacgggc aggatcgagc gagcggcgcg cccacggctc ctccggctat     780
ataacccgcc acccacacca ctcccctccg gcgttccacc agagccttcc tccctccacc     840
gcaccaccac caccaccgcg ccaaaaaccc tagggagcga gcgagctcac ctcgccccgc     900
cc                                                                    902

<210> SEQ ID NO 42
<211> LENGTH: 4504
<212> TYPE: DNA
<213> ORGANISM: Oryza sativa
<220> FEATURE:
<221> NAME/KEY: exon
<222> LOCATION: (1001)..(1363)
<220> FEATURE:
<221> NAME/KEY: exon
<222> LOCATION: (3093)..(3164)
<220> FEATURE:
<221> NAME/KEY: exon
<222> LOCATION: (3253)..(3505)

<400> SEQUENCE: 42
gaacagtgca ctggttggga taacaagaag ttagaaattg gcatatata tagaagggta       60
agacacctct aatggatagg gtggacaatc catcaaagat gactattttg gcacctctga     120

-continued

```
ggccgtgaca agttgcctat cttcgcaccc ttcacaagtg actccctact tgtgatgggt      180
cgtgagatgt gagccggtga tctttctcag atgtaaattt cggcctctca caagtgactc      240
cttatctgtg ataggtcttg ccctcacagc ctcatctgta acggcctcta attcaatccg      300
ttacagatta aatcattcat gacaagacac tttgacccat cataggtggg ttgttaatgt      360
tgaaccgagg tagcgtggtg gtggcttctt tgattgttga gcgggttgtg ttcttcatca      420
cttggtagga agtaggaacc caagaaggtt agaagcccac aactattata tcgtcggcct      480
cattggtaaa tgggctagaa gcctagaggc aatctgattc aatagtgtcg gaaatttgtg      540
gatgggccag agacgttgcg tcgtcttcga ctcttcgagt gcctggccta cggatctgca      600
cgaatcttag agcaagtaga aaatcgcata tcgtcgtgta gagcgcagca caaattcgag      660
ttgcttttcc cttttcgca gccaaatctt acctgctcac gtgccgtgct gcccggtgtg       720
cagagcccac gcgccacggc gccagtgtac tacaccgaat cggcaccatc catcgccaca      780
gctggccggt ccccctaag acggacgctc cggatcaatc cacgttggca tggcttcccc       840
gcatcgcctt ctccgcgccc ccgcctatat aatggcgctc tcgcttctct tccccatttc      900
gtcttcccct tctctagagc cttcctctca cagagcacac acaaaaccct agagtaggaa      960
gcgagcgaga gagagagaga gagagagaga gaccacaccc atg gag cgc tcc cac       1015
                                                Met Glu Arg Ser His
                                                  1               5 ctc gcc gtc ctg ctc ggc ctc ctc gcc ttc gcc gcc ggg gtc ccg gcc       1063
Leu Ala Val Leu Leu Gly Leu Leu Ala Phe Ala Ala Gly Val Pro Ala
             10                  15                  20 gca gcg gcg gcc acc gcc gtg gag gga gcg cag gcg gcc acg gcg gag       1111
Ala Ala Ala Ala Thr Ala Val Glu Gly Ala Gln Ala Ala Thr Ala Glu
         25                  30                  35 gcg tcg tgc gag ccc tcc atc ctc gcc acc cag gtc tcg ctc ttc tgc       1159
Ala Ser Cys Glu Pro Ser Ile Leu Ala Thr Gln Val Ser Leu Phe Cys
     40                  45                  50 gcg ccc gac atg ccc acc gcg cag tgc tgc gag ccg gtg gtg gcc tcc       1207
Ala Pro Asp Met Pro Thr Ala Gln Cys Cys Glu Pro Val Val Ala Ser
 55                  60                  65 gtc gac ctc ggc ggc ggt gta ccc tgc ctc tgc cgc gtc gcc gcc gag       1255
Val Asp Leu Gly Gly Gly Val Pro Cys Leu Cys Arg Val Ala Ala Glu
 70                  75                  80                  85 ccg cag ctc atc atc tcc ggc ctc aac gcc acc cac ctc ctc acg ctg       1303
Pro Gln Leu Ile Ile Ser Gly Leu Asn Ala Thr His Leu Leu Thr Leu
             90                  95                 100 tac gcc gcc tgc gga ggc ctc cgc cct gga ggc gct cgc ctc gcc gcc       1351
Tyr Ala Ala Cys Gly Gly Leu Arg Pro Gly Gly Ala Arg Leu Ala Ala
            105                 110                 115 gcc tgt gaa ggt acgtacatgc ataacctcct cctcctcctc ctcctctctc          1403
Ala Cys Glu Gly
        120 tctctctctc tctctctctc tctctctctc tctctctctc tctctctctc                1463 tctctctctc tctctctctc tctctctctc tctctctctc tctcggttgg ggttgctgcc     1523 ttgcgttttt ggttggtttt tcgtgggttg ggcgagatcc ttcgagttgc ttgtgttttg     1583 tggtatgcta ggcttcgaac gagttgccgg cgttgctgtg tcgaccaact ctcgtatgct     1643 tatctttcag cacatgagtt ttggcctcgt ttttactcgg ttgttgtatg ctacttctga    1703 gatttgagtt catccactgc taaactgaca tcatagatga agaatagcag cggcgtttgg    1763 tcgattttga ttccttttctc tggatgttcg agctgatctt gtggttattg ctcgaagcct    1823 cgaaacgctt gcgcacatgc aagatccagc aacgtataga tctatagtgg tgttgtgctt    1883
```

```
ttattcggat tgtggttca gtgtttacgt gcgaagtcac gcgttcgatg tttccgcttg    1943
agctccatat ctatagcaca aatcaatcat gtgcgttgcg cgagttcaag ctcgagagaa    2003
aagaaaagca tcaaggccac gggggtttt tgggccaggt cgtgattctc ccttgaactc    2063
cgaatatacc gagtttatta tcttttgagc ggatttggtg ttgaactggc aggactcaaa    2123
acccacccgt gggacgatcg ttttcttttc ctttcgcttt gtgttctctg tctcctttcc    2183
gtgaaatctc tgcgtttccc ttctggtgct tgttatagat gattctggat cgagccgtgt    2243
atgctcgtgc agtggtacga cttggcgatg aacgtgcttg cggagctagt cgcagttcat    2303
cttttctttt ttttcccctc gtttcttttc tcggcgtttc attctctaca cctcttctac    2363
tcgccatgca tgttcatctc tctccgtgtt ggtcctcatt tggagccgat tcgaaccggg    2423
cagcacagtg cttttttct gtttcgtttt ggaggtttcc actttcgtga aaaggaaagg    2483
gtcaaatcga atcgccccct gaaccatcct ttgcagagct tttttggacg tttccgcctt    2543
tcgtcagaga ccatctgcac tgcgcgtttc tccccaactc gatcgatttt gcagctttta    2603 atcactttt agaaaaagtt tttaatcact cgtcatcgat gtgatctctt gctctaattg    2663
catcttctcc gtaggattag cacttccatg cttcttgttt tgtctgttca attagccaag    2723
aaacgagtca gtataccttc aagatgcatg cagatttaaa atcggcactg ctctttatct    2783
tgttcttgtt tttgcaagtt ttggttggtt caaaacttat ctcttctgca gcattgcctg    2843
ctgtgtacag aaagttggca ggggcatcgt gcagcttttt tgcctgctgt gtgtaacgtt    2903
ttctttccgt acgttgcgtt ccgtttcacg tcgcttacct ctgtttcttg gggcgcaagt    2963
tatggcagta cagccgttgt ttccacgttg gaaggacggt tttgcccctt cgcttccaga    3023
agcttccaga gattttcga gtttttctaa tgtgtttgtt attgctgtaa ctcgttctaa    3083 cgtgcaggt ccc gcc cca ccg gcc tcc atc gtc act gcc ccg ccg ccc ccg    3134
         Pro Ala Pro Pro Ala Ser Ile Val Thr Ala Pro Pro Pro Pro
                 125             130                 135 gtt gct ttt cgc cgc aag ccg ccg gca cgt aaggctgatt gattcccctt        3184
Val Ala Phe Arg Arg Lys Pro Pro Ala Arg
         140                 145 catccactga ttgttaatgc gcgtgtaatc tttgtgatta ctaacttgct gctggatgct    3244 ttgcaggc gag gca cct ccc cca ccg ccg gcg gcc gag aag ctc tcc ccg    3294
         Glu Ala Pro Pro Pro Pro Ala Ala Glu Lys Leu Ser Pro
                 150                 155 ccg cct cag cag cac gac gac tcc gac cac aac aag cgc gtc ggc cca    3342
Pro Pro Gln Gln His Asp Asp Ser Asp His Asn Lys Arg Val Gly Pro
160             165                 170                 175 ctc ccg aga ggc tct cct ccc ccg tat gcc cag tcc gtc ccg gtc ggc    3390
Leu Pro Arg Gly Ser Pro Pro Pro Tyr Ala Gln Ser Val Pro Val Gly
                180                 185                 190 ccc gcc gcc gct ccc ccg cca cca cgc tcc ggc gcc tcc tcg tcg ctc    3438
Pro Ala Ala Ala Pro Pro Pro Arg Ser Gly Ala Ser Ser Ser Leu
                195                 200                 205 cag gcg ccc ctc gcc gcc acc acc acc atc gtt gcc atc acc ctc atc    3486
Gln Ala Pro Leu Ala Ala Thr Thr Thr Ile Val Ala Ile Thr Leu Ile
                210                 215                 220 gcc gcc gcc cag tac tga g gacacgccgc cgccggcgcc cgctccccag        3535
Ala Ala Ala Gln Tyr
        225 agccatgatt cgttcgcagt attttcatc ctgttctttt gcttctctct ctggctaccc    3595 atgtatatga gtttggaaga cgatgatttg atctagtagc gcgttaccaa gtttgcctag    3655
```

| | | | | |
|---|---|---|---|---|
| attcgagtag | tagctgtggt | actatgctga | tgtctctttg | atcgcgtcgt ctctagagcg | 3715 |
| tccgccgttt | ttgatcgatc | actagcatgg | ccgatgtgag | tccagcatga aaagtggtcg | 3775 |
| aggagaacat | tgttgctaag | tttttttttt | gctttctatc | tccagtagct gaacaagtat | 3835 |
| gtcaactgaa | tgctgcaatg | aagtgaatgg | atgcagtctt | aaatttagcc tttctgttgc | 3895 |
| caacttcttc | ctctgttctg | tacggttcag | atgctgcttg | ttctgtttat gcgatggtgt | 3955 |
| tgcattgttg | tgatgtgtga | agtgcgccca | attctgggtg | aactctgcag tattggcaag | 4015 |
| ctctgatcga | tacataaaga | actgaaatgt | gccggcttct | ccgcctcccg ttgcatgctc | 4075 |
| ttgtgcgcga | gctgcacagc | gcaaccgcgc | cctcctctgc | acatccatcg acacaaagtc | 4135 |
| tcaagttgtt | gcgcgtgtgc | tctaccaggc | accgtggctc | ctgcgggcgt gcacgggtca | 4195 |
| cattcacatc | gcacccaagt | tgcggacgtt | tcagctgagc | acctaccatc cgcaatgttt | 4255 |
| gcccacagct | tgctcgatga | aatgactggt | tcatgtcaaa | aggtaaaaac tgacattctc | 4315 |
| acgcggtaaa | ttcccctaag | cttcatagac | caccgcactg | tcatccactc gacctgccac | 4375 |
| gacacccgcc | accgcagaac | gcgacaccct | gtgcccacgg | ccacctaccc tggcacgcac | 4435 |
| cgagccgaag | ccggataagc | acccgagttg | atccccatga | gacgtggcga ctcggctgcc | 4495 |
| ctctgccac | | | | | 4504 |

<210> SEQ ID NO 43
<211> LENGTH: 684
<212> TYPE: DNA
<213> ORGANISM: Oryza sativa

<400> SEQUENCE: 43

| | | | | |
|---|---|---|---|---|
| atggagcgct | cccacctcgc | cgtcctgctc | ggcctcctcg | ccttcgccgc cggggtcccg | 60 |
| gccgcagcgg | cggccaccgc | cgtggaggga | gcgcaggcgg | ccacggcgga ggcgtcgtgc | 120 |
| gagccctcca | tcctcgccac | ccaggtctcg | ctcttctgcg | cgcccgacat gcccaccgcg | 180 |
| cagtgctgcg | agccggtggt | ggcctccgtc | gacctcggcg | gcggcgtacc ctgcctctgc | 240 |
| cgcgtcgccg | ccgagccgca | gctcatcatc | tccggcctca | acgccaccca cctcctcacg | 300 |
| ctgtacgccg | cctgcggagg | cctccgcccct | ggaggcgctc | gcctcgccgc cgcctgtgaa | 360 |
| ggtcccgccc | caccggcctc | catcgtcact | gccccgccgc | ccccggttgc ttttcgccgc | 420 |
| aagccgccgg | cacgcgaggc | acctccccca | ccgccggcgg | ccgagaagct ctccccgccg | 480 |
| cctcagcagc | acgacgactc | cgaccacaac | aagcgcgtcg | gcccactccc gagaggctct | 540 |
| cctcccccgt | atgcccagtc | cgtcccggtc | ggccccgccg | ccgctccccc gccaccacgc | 600 |
| tccggcgcct | cctcgtcgct | ccaggcgccc | ctcgccgcca | ccaccaccat cgttgccatc | 660 |
| accctcatcg | ccgccgccca | gtac | | | 684 |

<210> SEQ ID NO 44
<211> LENGTH: 5291
<212> TYPE: DNA
<213> ORGANISM: Brachypodium distachyon
<220> FEATURE:
<221> NAME/KEY: exon
<222> LOCATION: (2069)..(2419)
<220> FEATURE:
<221> NAME/KEY: exon
<222> LOCATION: (3818)..(3886)
<220> FEATURE:
<221> NAME/KEY: exon
<222> LOCATION: (4025)..(4288)

<400> SEQUENCE: 44

```
cccttaaaag ggggtaatga tggctcatat tgaggaattg acatgcaccc cttaaaggag      60
gtaatgatgg ctcatattga tttgaggaaa ctccttccat aaggacatct ccaacaagac     120
acagtcagcg gtactataaa gcacggcacc tggatcagtt ctcgtcgagg gtgcagacga     180
cgattgcagt gaatatgatg actatcgcgg cgacgaggag ggggggcagt ggggacggct     240
gaggtgcatc ctctgccaaa ttaaagcacg cgcgcgtgcc acgcgagtca gatcaaggac     300
acgcaaaaca gataacatat taacaggaag caacgcatag attttttagaa tcgagtaaaa     360
gaatagcagc agcattttttt ttagcgaaat agtagcagca attagatcaa gcgaaatgta     420
aaggttgttc acataccaac aagggcgcg gtgtggggcg ggacattgac ctccggggcc      480
tcctccaggg cctgcggcgc ctgctgggcc tcgacaaatg cagtcaggct gcaagatatg     540
agggtaaaaa aacagatgta cagtccggtc aagaaaaaca acaaacatgc agactactta     600
gatctgccaa gactaaatta cctaacgatt ccaagtccag tgatggttgc atcgcgatga     660
atttcagcca tgctgcgtgc ccgcctggtt accggacgcg cgggaagggg agcaagccca     720
atcagagcgg gtgcagccgg gcggcgtgtg ttattgcgat aatactcgac ggtatgcttc     780
caccgcaggt acagtctcag gaaggcatcc gattgaccca ccagatcatc tatcaccaag     840
gtagccattc tgccacccat ctaaacacaa actgagagta agaaagcagt ttgaccgcga     900
ttgtttatca caaaggcaa cacaaaaaaa ctgctagctt cgtgtcagaa atcaacatg      960
catggtgcgc gacagtacaa cagaaacatg gggagacata gcagaaacgt ccaaaccaaa    1020
aatccaaaaa aagaaggaga tgcactgcgt aagaaaacag cacgggaagc gctcttcacc    1080
gtgtgagact gcacaagtcc aagagacgac aatagcagaa aagaactgca gaaaggagag    1140
ctgctttcgg gggtcaaagt actagcacgg cttcgatcaa tcggtcgatt aaatccctcg    1200
tgccaccgag atcctcacag tgctcgaggg acactctaa gtcggctttg tcacatccaa     1260
cccaaacaac acgctcttgt ctaaggtgct caacaaaggt gatgtgttcg cacgcaggca    1320
cagtggaaca caaactagc gtcgatcgac cacgtccctc ccccagaaaa gtgctcccaa     1380
catgatcgca tcgaagtaat cgtagagata gatcttacag aataaaaaat aaacccaaac    1440
caaaggagga gttctgcact actagatccg aaccaaagcc aggaaatagc aaactaaaca    1500
caaaagatat cgatgaaatc atacatcgtc caaacgtttc ggattacacc ttctggtcgc    1560
aactctcgtg ctcaccgcgc agacagatct tctgtacgta ccttggctcc agcccgagga    1620
gagcgagcac tccaggaaac ggcggtctcg agcgagcagt ctaggaaatg gcggtcgcga    1680
tggaaaagcc ttcaagagat atcgggtgat gcccccatat tctagagctc tggccttttac   1740
agttcaccac ttcacctgc gccatcccga ttcccagtac ctatgacgag cgacgaccct    1800
cacgtgcctg gccagcatca cgggagagaa tcttgctcag catctcaacc gcccaaacag    1860
acagctgtcc ggtcccaccc aaatggacgc acaggatcga tcgggccgcc ggtggcctgt    1920
ccttggctaa cccttcacgc ctcttcgtcc cctccgccta taatcccca cccgctccg     1980
cttcttcccc caccgcgctc tcttcctctg gactcacacc aactcgccta gcctagcgg   2040
taggaagcga aagcgagaga tcccacccc atg gag aga tcc cac cac ctc ctc    2092
                                 Met Glu Arg Ser His His Leu Leu
                                  1               5 ctc gtg ctc ggc ctc ctc gcc gcg ctg ctc ccg gcg gcc gcg gct acc             2140
Leu Val Leu Gly Leu Leu Ala Ala Leu Leu Pro Ala Ala Ala Ala Thr
     10                  15                  20 ttc ggg acg acg cag ccg gag cct ggg gcc cca tgc gag ccc acc ctc            2188
Phe Gly Thr Thr Gln Pro Glu Pro Gly Ala Pro Cys Glu Pro Thr Leu
 25                 30                  35                  40
```

```
ctc gcc acc cag gtc tcg ctc ttc tgc gcg ccg gac atg ccg acc gcg    2236
Leu Ala Thr Gln Val Ser Leu Phe Cys Ala Pro Asp Met Pro Thr Ala
                45                  50                  55 cag tgc tgc gag cct gtg gtg gcc tcc gtc gac ctc ggg ggt ggc gtc    2284
Gln Cys Cys Glu Pro Val Val Ala Ser Val Asp Leu Gly Gly Gly Val
        60                  65                  70 ccc tgc ctc tgc cgt gtc gcc gcc gag ccg cag ctc gtc atg gcc ggc    2332
Pro Cys Leu Cys Arg Val Ala Ala Glu Pro Gln Leu Val Met Ala Gly
    75                  80                  85 ctc aac gcc acc cac ctc ctc acg ctc tac acc tcc tgc ggt gga ctc    2380
Leu Asn Ala Thr His Leu Leu Thr Leu Tyr Thr Ser Cys Gly Gly Leu
    90                  95                  100 cgc ccc gga ggc gcc cac ctc gcc gcc gcc tgt gaa ggt acgcgacgcc     2429
Arg Pro Gly Gly Ala His Leu Ala Ala Ala Cys Glu Gly
105             110                 115 tgcgtctctc tctctctctg cgtctctctc tgcgtctctc ccatgacgag caactcgcga   2489
tacgccttac tgccttattt tttttgaaga tatgtgtctg cttggtccac tgtatttggg   2549
ttcttctttc gagaagttca tccgtaggca tctataatcc gacgagttcg gatgagatca   2609
aacagtgaca cgcgcgacac caacgttttc aacgatctct tgctgtttgg tttgatattt   2669
cctgcttccc atgatctatt ttcaacctttt tttgtatggc tttcgctcca atctcgtgca  2729
gaaccatatt tcatcttggg tttatgctgt tctgtaagat ctagcgccat gcagaggtca   2789
tttctgctgt tccagacccc ctacgtgaca tttgctgttt ttcctctttg ttgccatggc   2849
cacgggttgg tttttacgaa agatactttg atatgtcaag atctgcgagc actttgaaac   2909
cccaacgcat tttctatgtg ttttgtgctg tttgatcgac cgattgatcg aggccgtgct   2969
agtactttga cacccgaaag catctctcct ttctgcagta tcttttctgt tcttgtcgtc   3029
tcttgggctt gtgcagttta ccatggtgaa gagcgcttca tacacgatct gccgcgaggc   3089
cagagcaaaa gcttcccgtg ctttttcttg cacagtgcat ctccttcttt tttgccttttt  3149 tcgtttggac gtttctgctt cgtctcccca tgtttctgtt gtactgtcgc gcaccatgca   3209
tgttgatttt ctgatacgaa gctagtactg ctctgcagtt tttgtgtagc cttcctcttt   3269
cgtgataaag aacgtggtca aactgctctc tgactctgtt cgtctaaatc ttttttctcgc  3329 aggaaaattt tcgttgcaga tctcctttac cctcgtcctc cgcatctgtt gctttaccct   3389
gctgtagttc gttcttcgt ttgaatcaaa ttcttgtttc cttctttat cccatcgctc     3449 gtttagttac ctttttcttt tattgaactt tagttcattg gtgtagtagg cagtagtatg   3509
ctttgcgttg tttgcggagt agcaattgaa ttgctctccg gtctctgcag agcggccccgc  3569 tgaacagata gctggctgca gcagctttac cagaatcggt cggttacgaa cttacgatta   3629
tacccttcgt cttgctttca tttactggta gcctgctagt ctttttcttgt tgcgcacgta   3689 atcgtaccca gtactgtacg cttagataaa atagacgggt ctggccttaa attatttcgt   3749
tgcgttttcg aattttgaat tccggaagtt aactttattt tgtgctctgt ttggacgcat   3809 gtgcaggt cca gct cct ccc gcc gcc gtc gtc agt gcc cct ccc ccc tcc   3859
        Pro Ala Pro Pro Ala Ala Val Val Ser Ala Pro Pro Pro Ser
                    120                 125                 130 gcc gca cct cgc cgc aag cag cca gca cgtacgaaca accttttaca           3906
Ala Ala Pro Arg Arg Lys Gln Pro Ala
                135             140 cttcgcttga tctaattgct gctgctatac tctcttactc gattctaaat ctatgttttg   3966
ctcattatta atatgttgat ctgactcgtg tggcacgcgc gcgtgctttg atttcgca     4024
```

```
gac gag gca cct ccg cct ccg ccg tcg act gag aag ccg tcc ccg ccg    4072
Asp Glu Ala Pro Pro Pro Pro Pro Ser Thr Glu Lys Pro Ser Pro Pro
            145                 150                 155 cct cag cag gac aac gtc acc gcc cac ggc aag gca atc ccc acc cat    4120
Pro Gln Gln Asp Asn Val Thr Ala His Gly Lys Ala Ile Pro Thr His
            160                 165                 170 gcg gcc aca tcc ccg ctc gcg ccg gct gct tcc atg atc cac atg tcc    4168
Ala Ala Thr Ser Pro Leu Ala Pro Ala Ala Ser Met Ile His Met Ser
            175                 180                 185 cca ccg ccc gca tgc aat cca tgc tcc ggc tcc gcc gct tcc tca gcc    4216
Pro Pro Pro Ala Cys Asn Pro Cys Ser Gly Ser Ala Ala Ser Ser Ala
            190                 195                 200 gag ggg ccc ctc ctc atc gcc gcg ctc ctc ctc gtc atc acc gcc atc    4264
Glu Gly Pro Leu Leu Ile Ala Ala Leu Leu Leu Val Ile Thr Ala Ile
205             210                 215                 220 atc gtc ggc acc ctc gac gat aag tgatccagga gccgtccgcc ccctccgact    4318
Ile Val Gly Thr Leu Asp Asp Lys
            225 caccaacgtc cgactatgat ccagttgcag tagtggtctt gttctgtttc atgtttctcg    4378 ccatttggtt ccgagatttc tatatcgtgc ctagtcgtag ctgtagcagt cagtatgttc    4438 atgtgtccac aagatgtggt cgagtataac attgggtttc atgattcctc tagcagatga    4498 aacactatgt gatgtgatct gaatggatgc agttttgcta ccttttctgc tgctatgata    4558 tgcttatcca tatgtttatc tttcattccc ttaatttgtg cggtttagcg ttgtgttgcc    4618 atgaatgcct cttgctctgc tttgcgggtt gcattttgtc ttcgttctgc tgtatatttg    4678 attctgaatt tgcatgctgt gagtactaag tactgactac aatctctgga tggttttgaa    4738 atttgaatga tgttataaag gagagctagc tggggaattg cctcacctct aaactccaaa    4798 acacagagca gaagttggcc tcaagatcca acttggtcac tttgcatgtc ggagcattgt    4858 agcaattctg caataaacgg agtagttctg ttagcatgtt gttttacac tgtcagtaca    4918 agtagaggtc gatgattaat tatattccgg ttgtttgctg ctggcttccc agttccctcc    4978 aggtaggaag gaaccgtatc cgggtagtag ccagtagtag ccaggaagct actagcagaa    5038 cagtcttctg gtgctctttt tttggagtaa cgtcttctcg cgatcttttt cgagtaattc    5098 aaatccgggt ataccgagcc ttgtatcagt gagagccgat agtcttaatt atctccagca    5158 caggcacagg aacaaccacg tttgtttttc agaatgcaca gcaacatttt ttttaagagc    5218 atggcacagc tactttttt ttttttaagg aaacatggca cagctacatt ttttttaga    5278 ggaacatggc aca    5291
```

<210> SEQ ID NO 45
<211> LENGTH: 684
<212> TYPE: DNA
<213> ORGANISM: Brachypodium distachyon

<400> SEQUENCE: 45

```
atggagagat cccaccacct cctcctcgtg ctcggcctcc tcgccgcgct gctcccggcg     60
gccgcggcta ccttcgggac gacgcagccg gagcctgggg ccccatgcga gcccacccct    120
ctcgccaccc aggtctcgct cttctgcgcg ccggacatgc cgaccgcgca gtgctgcgag    180
cctgtggtgg cctccgtcga cctcgggggt ggcgtcccct gcctctgccg tgtcgccgcc    240
gagccgcagc tcgtcatggc cggcctcaac gccacccacc tcctcacgct ctacacctcc    300
tgcggtggac tccgccccgg aggcgcccac ctcgccgccg cctgtgaagg tccagctcct    360
cccgccgccg tcgtcagtgc ccctcccccc tccgccgcac ctcgccgcaa gcagccagca    420
```

```
cacgaggcac ctccgcctcc gccgtcgact gagaagccgt ccccgccgcc tcagcaggac    480
aacgtcaccg cccacggcaa ggcaatcccc acccatgcgg ccacatcccc gctcgcgccg    540
gctgcttcca tgatccacat gtccccaccg cccgcatgca atccatgctc cggctccgcc    600
gcttcctcag ccgaggggcc cctcctcatc gccgcgctcc tcctcgtcat caccgccatc    660
atcgtcggca ccctcgacga taag                                           684
```

<210> SEQ ID NO 46
<211> LENGTH: 951
<212> TYPE: DNA
<213> ORGANISM: Triticum aestivum

<400> SEQUENCE: 46

```
tcgcgcgccg accccgcgag agaccgtggt ccgtccagtc gcagtagagt agagcgctcg     60
tcgtctcgtt ccgtttcgtg cctgtcgccg ttcgaggttc gtttctgcgt gcagtccggt    120
cgaagaagcc ggtgggtttt gagtactagt ggtagtagta gcagcagcta tcgtttctgt    180
ccgctcgtac gtgtttgcgt ggtcgcggag aacaattaat tgggtgtttg cgagtcctct    240
ggttaagatg aaccactgat gctatgtgat cgatcgatcg gtatgatctg aatggaaatg    300
gatcaagttt tgcgttctgc tgatgatgtg atccatttgg atctgtgtgg ggcaacagtt    360
tcgcttgctt ttgctctgcg atgaacgaat gcttcttgca tgcatcttgt ctttgcttaa    420
tttgaactgt agaacggatg cagtactgat ttctgcttat gatgtgacga ttcgtcgtac    480
gcatatcatc tcttcaaatt tgtgtagcag ctgtttgtag cttccattct gctatggacg    540
aatgcctgtt tttcacggag aaccgcgcgc ggggaccgat gcggctttgt gttgccatgt    600
tgttttccac gccaggacaa aatagatggt gcggttttga tccccaatcc caccatcacc    660
atgttccgga gagccacatg gaactcacgt caagcggtca cttttttgcag aatcactctt    720 accattttac ccttttgttg aaacctctct cctcatcccc aaaagttgat gcaacagtgc    780
tatgcgcgcc cacccatgct ttttcatatg attgtaaaat ttggatcgat tttatcttt     840 gaaccctaag tccggtttac aatctgtttg catgtttatg ttccttgcgg cgaggaccat    900
taaacaagac tactattgga tatatttcga caggctttga aatccgaatt c             951
```

<210> SEQ ID NO 47
<211> LENGTH: 1000
<212> TYPE: DNA
<213> ORGANISM: Hordeum vulgare

<400> SEQUENCE: 47

```
tggccgaccc ccaaggcagc agagtacttg tcatctgatt ccgtttcatg cttgtcgccg     60
tttgttgagg ttcgtttctg cagtccgaac aagacggtgg ggttttgatc gggtacccag    120
atttctatgt cgatcgcgcg tactagtact agtagttgct tagcagatga acgaacattg    180
ggttttggga ttcctctagc tgatgaacca ctgctatttt ccatgtgatc gatggatatg    240
atctgaatgg atggatgaag ttttggtttc tgatgctgat gatgtgctgc ttcttcattt    300
gcatgctcga tctattcctt caattttgtg gagcaacagt tgtttagct tctgttctgc     360 tatgaataat gccgcttgca tcttgtcatt gctgataatc tgcttaatgc agacattgct    420
tccgtcccaa acaatctgtt gcttaccagg taatgcatat aatctgtacc tcaccttcgc    480
acaacaacag aagctaccct gctaaaaaaa cacacacaca cacacaaaaa aaacagaagc    540
tggtctcaca cggaagccgc ttcggggact gtttgcagct ttttattgcc attttgtttt    600
```

```
tcatgcaggt acaaatcgag ggtgttgctt gatttgatca tggatgatca cttagagcaa        660
catgtgtgtt ttgtctgtgt tttattcgtt gctcgtccat ccaatttaaa cttgaaatgg        720
atcgtgtgtg gataaaagaa gacgtgcgtc agtttgaatc gacgcgttgg gttatatttt        780
gtgtctgtga cgaccgaaac gaagacaaaa tatatcgtcc ggttagaatt gctctaatgc        840
tagctttctc tcctaccatc gcattccgtg gtaggaaaaa gtactagaac cacaggaaac        900
tggaacgcaa gaaaagcata tctaccgttg gccgttgatc ttgtttcaca ttcggtatgg        960
ctccggtcat attgttggag attcacattc atgcacgcaa                             1000
```